(12) United States Patent
Østergaard

(10) Patent No.: US 7,069,068 B1
(45) Date of Patent: Jun. 27, 2006

(54) METHOD FOR DETERMINING HAEMODYNAMIC INDICES BY USE OF TOMOGRAPHIC DATA

(76) Inventor: Leif Østergaard, Jacob Knudsens Vej 5, DK-8230 Aabyhøj (DK)

( * ) Notice: Subject to any disclaimer, the term of this patent is extended or adjusted under 35 U.S.C. 154(b) by 0 days.

(21) Appl. No.: 09/937,146

(22) PCT Filed: Mar. 23, 2000

(86) PCT No.: PCT/DK00/00140

§ 371 (c)(1),
(2), (4) Date: Nov. 15, 2001

(87) PCT Pub. No.: WO00/57777

PCT Pub. Date: Oct. 5, 2000

Related U.S. Application Data

(60) Provisional application No. 60/126,322, filed on Mar. 26, 1999.

(30) Foreign Application Priority Data

May 27, 1999 (DK) ............................... 1999 00749

(51) Int. Cl.
*A61B 5/00* (2006.01)

(52) U.S. Cl. ...................... 600/420; 600/407; 600/410; 600/415; 600/419; 600/425; 600/431; 600/432; 600/436; 600/476; 324/307; 324/308; 324/309

(58) Field of Classification Search ................ 600/420, 600/473, 410, 419, 431, 425, 323, 328, 476, 600/415, 432, 436; 324/307–309
See application file for complete search history.

(56) References Cited

U.S. PATENT DOCUMENTS

| 5,287,273 | A | * | 2/1994 | Kupfer et al. | 600/431 |
| 5,377,681 | A | * | 1/1995 | Drane | 600/419 |
| 5,590,654 | A | * | 1/1997 | Prince | 600/420 |
| 5,783,606 | A | * | 7/1998 | Tatton | 514/649 |
| 5,799,649 | A | * | 9/1998 | Prince | 600/420 |
| 5,853,370 | A | * | 12/1998 | Chance et al. | 600/473 |
| 5,924,987 | A | * | 7/1999 | Meaney et al. | 600/420 |
| 5,928,148 | A | * | 7/1999 | Wang et al. | 600/420 |

(Continued)

OTHER PUBLICATIONS

Bock J C et al.: "Magentic Resonance Perfusion Imaging with Gadolinium-DTPA. A Quantitative Approach for the Kinetic Analysis of First-Pass Residue Curves" Investigative Radiology, vol. 30, No. 12, 1995, pp. 693-699 XP002901064.

(Continued)

*Primary Examiner*—Eleni Mantis-Mercader
*Assistant Examiner*—Baisakhi Roy
(74) *Attorney, Agent, or Firm*—Birch Stewart Kolasch & Birch LLP

(57) ABSTRACT

Haemodynamic indices of an organ or a part of tissue are determined from a time series of tomographic data obtained by means of Magnetic Resonance Imaging. Maps of indices are produced, being significant of the dynamics of the capillary tissue flow acquired during rapid bolus injection of a tracer that stays mainly intravascular. The method may be used for evaluating the efficacy of a drug on an organ, or for obtaining information of the likelihood of recovery of an organ or part of tissue upon or during a period of insufficient vascular supply or during the progression of a chronic disease. The method may be used for discriminating between relevant therapy of an organ.

31 Claims, 35 Drawing Sheets

U.S. PATENT DOCUMENTS

| | | | |
|---|---|---|---|
| 6,230,041 B1 * | 5/2001 | Prince | 600/420 |
| 6,397,097 B1 * | 5/2002 | Requardt | 600/431 |
| 6,760,611 B1 * | 7/2004 | Watanabe | 600/410 |

OTHER PUBLICATIONS

Ostergaard L et al.: "High Resolution Measurement of Cerebral Blood Flow using Intravascular Tracer Bolus Passages. Part I: Mathematical Approach and Statistical Analysis" Magnetic Resonance in Medicine, vol. 36, 1996, pp. 715-725, XP002901065.

Ostergaard L et al.: "High Resolution Measurement of Cerebral Blood Flow Using Intravascular Tracer Bolus Passages. Part II: Experimental Comparison and Preliminary Results" Magnetic Resonance in Medicine, vol. 36, 1996, pp. 726-736, XP002901066.

King R B et al.: "Modeling Blood Flow Heterogeneity" Annals of Biomedical Engineering, vol. 24, 1996, pp. 352-372, XP002901067.

Ostergaard L et al.: Cerebral Blood Flow Measurements by Magnetic Resonance Imaging Bolus Tracking: Comparison With [150] H2O Journal of Celebral Blood Flow and Metabolism, vol. 18, 1998, pp. 935-940, XP002901068 p. 727.

Schreiber W G et al.: "Cerebral Blood Flow and Cerebrovascular Reserve Capacity: Estimation by Dynamic Magnetic Resonance Imaging" Journal of Cerebral Blood Flow and Metabolism, vol. 18, 1998, pp. 1143-1156, XP002901069.

Ostergaard L et al.: "Absolute Cerebral Blood Flow and Blood Volume Measured by Magnetic Resonance Imaging Bolus Tracking: Comparison With Positron Emission Tomography Values" Journal of Cerebral Blood Flow and Metabolism, vol. 18, 1998, pp. 425-432, XP002901070.

Abounader et al., "Patterns of Capillary Plasma Perfusion in Brains of Conscious Rats During Normocapnia and Hypercapnia," Circulation Research, vol. 76, No. 1, Jan. 1995, pp. 120-126.

Aronen et al., "Cerebral Blood Volume Maps of Gliomas: Comparison with Tumor Grade and Histologic Findings," Radiology, vol. 191, No. 1, Apr. 1994, pp. 41-51.

Baron et al., "Reversal of Focal 'Misery-Perfusion Syndrome' By Extra-Intracranial Arterial Bypass in Hemodynamic Cerebral Ischemia," Stroke, vol. 12, No. 4, Jul.-Aug. 1981, pp. 454-459.

Bock, "Pathogenesis of Acute Renal Failure: New Aspects," Contrib. Nephrol., vol. 124, 1998, pp. 43-63.

Boxerman et al., "MR Contrast due to Intravascular Magnetic Susceptibility Perturbations," Magn. Reson. Med., vol. 34, 1995, pp. 555-566.

Buell et al., "Combined SPECT Imaging of Regional Cerebral Blood Flow ($^{99m}$Tc-Hexamethyl-Propyleneamine Oxime, HMPAO) and Blood Volume ($^{99m}$Tc-RBC) to Assess Regional Cerebral Perfusion Reserve in Patients with Cerebrovascular Disease," NuklearMedizin, vol. 27, 1988, pp. 51-56.

Chan et al., "SENSOP: A Derivative-Free Solver for Nonlinear Least Squares with Sensitivity Scaling," Annals of Biomedical Engineering, vol. 21, 1993, pp. 621-631.

Claudon et al., "Renal Blood Flow in Pigs: Changes Depicted with Contrast-enhanced Harmonic US Imaging during Acute Urinary Obstruction," Radiology, vol. 212, 1999, pp. 725-731.

Crone, "The Permeability of Capillaries in Various Organs as Determined by Use of the 'Indicator Diffusion' Method," Acta physiol. scand., vol. 58, 1963, pp. 292-305.

Endrich et al., "The Role of the Microcirculation in the Treatment of Malignant Tumors: Facts and Fiction," Blood Perfusion and microenvironment of human tumors, 1998, pp. 20-39.

Ferrara et al., "Clinical applications of angiogenic growth factors and their inhibitors," Nature Medicine, vol. 5, No. 12, Dec. 1999, pp. 1359-1364.

Fisel et al., "MR Contrast Due to Microscopically Heterogeneous Magnetic Susceptibility: Numerical Simulations and Applications to Cerebral Physiology," Magnetic Resonance in Medicine, vol. 17, 1991, pp. 336-347.

Frokiaer et al., "Renal hemodynamic response to ureteral obstruction during converting enzyme inhibition," Urol Res, vol. 24, 1996, pp. 217-227.

Gibbs et al., "Evaluation of Cerebral Perfusion Reserve in Patients with Carotid-Artery Occlusion," The Lancet, Feb. 11, 1984, pp. 310-314.

Grubb et al., "The Effects of Changes in $PaCO_2$ on Cerebral Blood Volume, Blood Flow, and Vascular Mean Transit Time," Stroke, vol. 5, Sep.-Oct. 1974, pp. 630-639.

Heiss et al., "Dynamic Penumbra Demonstrated by Sequential Multitracer PET after Middle Cerebral Artery Occlusion in Cats," Journal of Cerebral Blood Flow and Metabolism, vol. 14, 1994, pp. 892-902.

Hudetz et al., "Effects of Hypoxia and Hypercapnia on Capillary Flow Velocity in the Rat Cerebral Cortex," Microvascular Research, vol. 54, 1997, pp. 35-42.

Hudetz et al., "Heterogeneous Autoregulation of Cerebrocortical Capillary Flow: Evidence for Functional Thoroughfare Channels?", Microvascular Research, vol. 51, 1996, pp. 131-136.

Hvistendahl et al., "Renal Hemodynamic Response to Gradated Ureter Obstruction in the Pig," Nephron, vol. 74, 1996, pp. 168-174.

Iversen et al., "Increased glomerular capillary pressure and size mediate glomerulosclerosis in SHR juxtamedullary cortex," Am. J. Physiol., vol. 274 (Renal. Physiol., vol. 43), 1998, pp. F365-F373.

Johnson, "Peripheral Circulation," New York, Wiley, 1973, pp. 1-4.

Kent et al., "Quantitative Cerebral Blood Flow Changes Using Contrast Enhanced MRI: Modulation by Nitric Oxide," Journal of Cerebral Blood Flow, vol. 17, Suppl. 1, 1997, pp. S14.

King et al., "A vascular transport operator," Am. J. Physiol., vol. 256, pp. H2196-H2208.

Kroll et al., "Modeling regional myocardial flows from residue functions of an intravascular indicator," Am. J. Physiol., vol. 271, 1996, pp. H1643-H1655.

Kuschinsky et al., "Capillary Circulation in the Brain," Cerebrovascular and Brain Metabolism Reviews, vol. 4, 1992, pp. 261-286.

Kwong et al., "Dynamic magnetic resonance imaging of human brain activity during primary sensory stimulation," Proc. Natl. Acad. Sci. USA, vol. 89, Jun. 1992, pp. 5675-5679.

Lammertsma et al., "*In Vivo* Measurement of Regional Cerebral Haematocrit Using Positron Emission Tomography," Journal of Cerebral Blood Flow and Metabolism, vol. 4, 1984, pp. 317-322.

Lassen, "Cerebral Transit of an Intravascular Tracer May Allow Measurement of Regional Blood Volume But Not Regional Blood Flow," Journal of Cerebral Blood Flow and Metabolism, vol. 4, 1984, pp. 633-634.

Leenders et al., "Cerebral Blood Flow, Blood Volume and Oxygen Utilization," Brain, vol. 113, 1990, pp. 27-47.

Li et al., "Nonlinear Model for Capillary-Tissue Oxygen Transport and Metabolism," Annals of Biomedical Engineering, vol. 25, 1997, pp. 604-619.

Moseley et al., "Early Detection of Regional Cerebral Ischemia in Cats: Comparison of Diffusion- and T2-Weighted MRI and Spectroscopy," Magnetic Resonance in Medicine, vol. 14, 1990, pp. 330-346.

Nagata et al., "Glomerular damage after uninephrectomy in young rats. I. Hypertrophy and distortion of capillary architecture," Kidney International, vol. 42, 1992, pp. 136-147.

Ohta et al., "Cerebral [$^{15}$O] Water Clearance in Humans Determined by PET: I. Theory and Normal Values," Journal of Cerebral Blood Flow and Metabolism, vol. 16, 1996, pp. 765-780.

Ostergaard et al., "Early changes measured by magnetic resonance imaging in cerebral blood flow, blood volume, and blood-brain barrier permeability following dexamethazone treatment in patients with brain tumors," J. Neurosurg. vol. 90, 1999, pp. 300-305.

Ostergaard et al., "Modeling Cerebral Blood Flow and Flow Heterogeneity From Magnetic Resonance Residue Data," Journal of Cerebral Blood Flow and Metabolism, vol. 19, 1999, pp. 690-699.

Ostergaard et al., "Magnetic Resonance Imaging Measurements of Flow Heterogeneity Demonstrate High Risk of Infarction in Acute Stroke," Denmark, 2000, pp. 1-21.

Porkka et al., "Arterial-input function measurement with MRI," Proceedings of the Society of Magnetic Resonance in Medicine's 10$^{th}$ annual Meeting, San Francisco, California, 1991, pp. 120.

Powers, "Cerebral Hemodynamics in Ischemic Cerebrovascular Disease," Ann Neurol, vol. 29, 1991, pp. 231-240.

Press et al., "Numerical Recipes in C, The Art of Scientific Computing, Second Edition," Oxford: Cambridge University Press, 1992, pp. 676-679.

Renkin, "Exchangeability of tissue potassium in skeletal muscle," Am. J. Physiol., vol. 197, 1959, pp. 1211-1215.

Rosen et al., "Susceptibility Contrast Imaging of Cerebral Blood Volume: Human Experience," Magnetic Resonance in Medicine, vol. 22, 1991, pp. 293-299.

Rosen et al., "Perfusion Imaging with NMR Contrast Agents," Magnetic Resonance in Medicine, vol. 14, 1990, pp. 249-265.

Rosen et al., "Contrast Agents and Cerebral Hemodynamics," Magnetic Resonance in Medicine, vol. 19, 1991, pp. 285-292.

Schumann et al., "Evaluation of the ratio of cerebral blood flow to cerebral blood volume as an index of local cerebral perfusion pressure," Brain, vol. 121, 1998, p. 1369-1379.

Shea et al., "Glomerular Hemodynamics and Vascular Structure in Uremia: A Network Analysis of Glomerular Path Lengths and Maximal Blood Transit Times Computed for a Microvascular Model Reconstructed from Subserial Ultrathin Sections," Microvascular Research, vol. 28, 1984, pp. 37-50.

Sorensen et al., "Hyperacute Stroke: Evaluation with Combined Multisection Diffusion-weighted and Hemodynamically Weighted Echo-planar MR Imaging," Radiology, vol. 199, 1996, pp. 391-401.

Sorensen et al., "Hyperacute Stroke: Simultaneous Measurement of Relative Cerebral Blood Volume, Relative Cerebral Blood Flow, and Mean Tissue Transit Time," Radiology, vol. 210, 1999, pp. 519-527.

Stewart, "Researches on the Circulation Time in Organs and on the Influences Which Affect It," Proc. Physiol. Soc., vol. 15, Nov. 8, 1890, pp. 1-89.

Villringer et al., "Dynamic Imaging with Lanthanide Chelates in Normal Brain: Contrast Due to Magnetic Susceptibility Effects," Magnetic Resonance in Medicine, vol. 6, 1988, pp. 164-174.

Vogel et al., "Decreased Heterogeneity of Capillary Plasma Flow in the Rat Whisker-Barrel Cortex During Functional Hyperemia," Journal of Cerebral Blood Flow and Metabolism, vol. 16, 1996, pp. 1300-1306.

Weisskoff et al., "Pitfalls in MR Measurement of Tissue Blood Flow with Intravascular Tracers: Which Mean Transit Time?", Magnetic Resonance in Medicine, vol. 29, 1993, pp. 553-558.

Weisskoff et al., "Microscopic Susceptibility Variation and Transverse Relaxation: Theory and Experiment," Magnetic Resonance in Medicine, vol. 31, 1994, pp. 601-610.

Wise et al., "Serial Observations on the Pathophysiology of Acute Stroke," Brain, vol. 106, 1983, pp. 197-222.

Wong et al., "Implementation of Quantitative Perfusion Imaging Techniques for Functional Brain Mapping Using Pulsed Arterial Spin Labeling," NMR in Biomedicine, vol. 10, 1997, pp. 237-249.

Yamakawa et al., "White Blood Cell Plugging and Blood Flow Maldistribution in the Capillary Network of Cat Cerebral Cortex in Acute Hemorrhagic Hypotension," Circulatory Shock, vol. 22, 1987, pp. 323-332.

* cited by examiner

Acute p on CBF map

METHOD FOR DETERMINING HAEMODYNAMIC INDICES BY USE OF TOMOGRAPHIC DATA

This application claims the benefit of Provisional Application No. 60/126,322 filed Mar. 26, 1999

This application is the national phase under 35 U.S.C. § 371 of PCT International Application No. PCT/DK00/00140 which has an International filing date of Mar. 23, 2000, which designated the United States of America and was published in English.

The present invention relates to a method for determining haemodynamic indices of an organ or a part of tissue of a mammal, such as a human being, from a time series of tomographic data, especially data obtained by means of Magnetic Resonance Imaging (MRI). The method produces maps of distribution of blood transit time as well as other indices being significant of the dynamics of the capillary tissue flow from tomographic images acquired during rapid bolus injection of a contrast agent or tracer that stays mainly intravascular in the organ. The haemodynamic indices may by use of the present method be obtained with a spatial resolution equal to the spatial resolution of the tomographic data.

The method comprises the steps of conversion of tomographic images into data representing concentrations of contrast agent as a function of time, and the method determines the distribution of flow and mean transit time, either in absolute values or relative to the mean value, whereby the methods facilitates the (i) comparison of relative flow or transit time distributions to that of other tissue (in particular cerebral tissue), such as normal tissue, or (ii) quantification of absolute flow distributions in terms of the associated extraction of a substance with known capillary permeability.

The use of the methods for examination and monitoring of cerebral conditions of humans are of particular interest, but the method may also be applied to other organs, such as the heart, the liver, kidneys, tumors etc., or to other part of tissue or part of organs.

BACKGROUND

Flow and microscopic heterogeneity of flow are believed to be a main determinants of how efficient the delivery of nutrients and pharmaceuticals to tissue takes place. Especially in diseases where delivery of nutrients such as e.g. oxygen is compromised by flow reduction, determination of flow heterogeneity is therefore crucial to assess the severity of the disease. Such diseases include acute cerebral ischemia, a frequent cause of death and the major cause of adult neurological disability in the Western world.

So far, the measurement of flow heterogeneity has been limited to the study to superficial vessels in the cortex of anaesthetised animals by high-speed intravital microscopy. There are no pre-existing tools that allow determination flow heterogeneity in deeper structures, or on humans as part of non-invasive, routine diagnostic procedures.

The study of the delivery of nutrients to the tissue is currently done by Positron Emission Tomography (PET). Due to the costs and lack of general availability of this technique, these studies can, however, not be performed in general patient management.

A major limiting factor in the development of new drugs in many diseases is the cost of preclinical and clinical trials to determine beneficial effects of new agents. In acute stroke, this is typically done by comparing long-term neurological scores of hundreds of treated and untreated patients. The costs of this work, as well as the total number of patients available, therefore limits the rate at which novel drugs become available for common use. There exists therefore an urgent need for techniques that in individual patients predict the progression of a disease or condition and may be used for monitoring of said progression, so that the progression for the individual patient can be assessed whereby e.g. the efficacy of a drug or a substance can be evaluated in details from a much more limited number of patients. Such techniques are not currently available.

With regards to determining tissue flow, most quantitative techniques utilise tomographic images of the distribution of radionucleides combined with invasive blood sampling. With the spatial resolution of some tomographic imaging techniques, the dimensions of vessels are too small to accurately determine arterial tracer concentration levels non-invasively. Instead, image elements containing partly tissue, partly blood vessels must be used in order to characterise the mere shape of the arterial input curve to the tissue. In such cases, absolute values of flow and volume cannot be found, and therefore a normalisation routine allowing (i) comparison of serial measurements in a single subject, (ii) comparison among subjects and (iii) absolute quantification the case of susceptibility MRI of the brain is necessary as described below.

The present invention describes and validates a new, non-invasive method that allows assessment of flow heterogeneity on generally available tomographic equipment (Magnetic Resonance (MR), Computed Tomography (CT), PET). Furthermore, the technique allows indirect assessment of metabolic parameters.

Finally, the technique has high predictive power in terms of disease progression in cerebral diseases such as ischemia, thereby providing the means for rapid assessment of the efficacy of novel therapies.

DESCRIPTION OF THE INVENTION

It is an object of the present invention to provide a method for determining haemodynamic indices of an organ or part of tissue of a mammal, such as a human being from tomographic data.

By haemodynamic indices is understood such indices as distribution of transit times and parameter characterising said distribution, quantitative haemodynamic parameters obtained from said distribution such as parameters characterising the deviation of said distribution from a reference distribution, as well as other indices being significant of the dynamics of the capillary tissue flow.

It is a further object of the present invention to facilitate the comparison of relative flow distributions to a predetermined distribution found for a normal organ (e.g. the brain) or for an organ having a recognised disease or condition, such as having a tumour of an identified tumour type.

It is a still further object of the invention to facilitate the above mentioned comparison for voxels of an organ.

It is a yet still further object of the present invention to provide quantification of absolute flow distributions in terms of the associated extraction of a substance with known capillary permeability.

It is an even yet still further object of the present invention to provide the above methods so that they are applicable to human cerebral tissue.

Thus, the present invention relates to a method for determining haemodynamic indices of an organ or part of tissue of a mammal including a) determining a time series of tomographic data pertaining to the organ or part of tissue during and after a bolus injection of a tracer dose to said mammal, the tracer being substantially intravascular in said tissue, b) determining a time series of concentration data being indicative of the concentration of the tracer in arteries of the organ or tissue from the time series of tomographic data, c) determining a residue function of the organ or of the part of tissue by deconvolution of the time series of tomographic data with the time series of concentration data, and d) determining a distribution of transit times from the slope of the residue function.

The residue function may also be understood as a normalised impulse response function characterising the fraction of the tracer present in the vascular tissue at time t after a perfect, infinitely sharp input of a tracer in the feeding vessel. For the deconvolution a number of known methods may be applied, such as a Fourier transform, Box transform, but preferably the Singular Value Decomposition is used.

The term "tomographic data" is herein understood as data representing the concentration of the tracer, i.e. being a direct measure of the concentration or being directly proportional to the concentration of the tracer. Thus, the "tomographic data" and the "concentration data" typically have the same physical dimension.

The distribution of transit times obtained from this method may be used to determine a probability density function (PDF) of a normalised haemodynamic index, where the index is normalised by the value of the integral of this index.

One of the haemodynamic indices obtained from the PDF may be a quantitative haemodynamic parameter, such as a parameter obtained from comparison of the determined PDF and a previously determined reference PDF, e.g. obtained by use of the Kolmogorov Smirnov test. The comparison between the determined PDF and a reference may also include identification of plateau's of the curve of the PDF, distribution of area under the curve, area under the curve at one or the other side of a cut-off value, etc.

The predetermined reference PDF used for comparison may have been found for a normal organ (e.g. the brain) or tissue or for an organ having a recognised disease or condition, such as having a tumour of an identified tumour type.

Furthermore, the present invention relates to a method in which the quantitative parameter may be obtained by performing the steps of determining the impulse response function of the organ or of the part of tissue by deconvolution of the time series of tomographic data with the time series of concentration data, determining the relative tissue flow from the impulse response function of the organ or of the part of tissue, normalising said time series of concentration data with the integral of said time series of concentration data with respect to time, determining the normalised relative tissue flow, respectively the normalised blood volume, of the organ or part of tissue by use of the relative tissue flow and the time series of normalised concentration data, and converting said normalised relative tissue flow, respectively normalised blood volume, to an absolute value for the tissue flow, respectively the blood volume, by means of a previously determined conversion factor, the quantitative haemodynamic parameter being of metabolic significance and determined from the PDF and the absolute tissue flow, respectively the absolute blood volume.

The normalised relative tissue flow obtained from this method may be used to compare tissue flow determined from successive tomographic scanning of the same mammal in order to monitor the development of a condition of an organ or part of tissue and/or to compare tissue flow of different individuals. The comparison may be performed because the data have been normalised which means that they are readily comparable.

The blood volume is obtained by dividing the blood flow by the mean transit time (MTT) or as the area under the tissue concentration curve (or the impulse response function) of the first pass of the bolus tracer passage.

It is understood that the tomographic data may be obtained from a variety of methods, of which MRI and Computed Tomography (CT) are preferred. However, for some applications it may be preferred to use other methods, such as Positron Emission Tomography (PET) or Single Photon Emission Computed Tomography (SPECT).

The above method may further comprise a step, wherein the normalised relative tissue flow, respectively the blood volume, is also normalised with the ratio between body weight of the individual mammal and the injected tracer dose. By adding this step, the determined relative tissue flow is furthermore made comparable to determined relative tissue flow from tomography time series of the same individual mammal in which the amount of the injected tracer dose have been changed. The relative tissue flow determined for one individual mammal may furthermore be compared to relative tissue flows determined for other individuals.

The conversion factor may be a factor that is generally applicable for the present method to members of a mammalian specie.

In particular, the conversion factor may be a factor that is generally applicable for the present method to an organ or tissue of the mammalian specie.

As a special case, a parameter (E) significant for the local extraction of a substance may be determined by a method further comprising the following steps:

calculating the relative flow heterogeneity (w(f)) as a function of the relative flow (f) from the distribution of transit times, estimating a value (P) for the local capillary permeability, estimating a value (S) for the local capillary surface area, calculating said parameter (E) as the integral value of the relative flow heterogeneity (w(f)) multiplied by one minus the natural exponential function of the negative ratio between i) the product of the local capillary permeability (P) and the local capillary surface area (S), and ii) the product of the relative flow (f) and the absolute tissue flow ($F_t$) with respect to the relative flow (f)

The substance in question may, e.g., be oxygen, glucose or another important cellular metabolic substance or it may, e.g., be a drug or another substance having a therapeutic effect.

Estimated values of the local capillary permeability (P) and the local capillary surface area (S) are well-known and may be found from standard works within the subject area.

Preferably, the normalised relative tissue flow, respectively the blood volume, is also normalised with the injected tracer dose being the ratio between tracer amount and body weight of the individual mammal.

The tomography data for the method according to the invention are preferably obtained by means of magnetic resonance imaging, and the method is furthermore preferably applied to cerebral tissue. For cerebral tissue, it has been found to be advantageous to obtain the tomographic data by means of susceptibility contrast magnetic resonance imaging.

The tissue may be renal tissue, in particular renal parenchyma tissue.

The tissue may further include tumour tissue, in particular in case the tissue is cerebral tissue.

The tracer may be a Gd-chelate, such as Gd-DTPA. It may alternatively be an ultra small iron oxide particle (USPIO) intravascular contrast agent. This is particularly preferred since an USPIO intravascular contrast agent is only transferred to the surrounding tissue to a very limited extend. Thus, the contrast agent is mainly maintained in the blood, whereby the contrast of the resulting MR image is greatly enhanced. This is of particular interest in non-cerebral tissue, such as renal tissue.

The predetermined conversion factor may be a constant factor applicable for the present method for any organ or any part of tissue of the mammalian specie. Preferably, the predetermined conversion factor is a constant factor applicable for all of cerebral tissue of the mammalian specie, which is strongly indicated from empirical evidence.

The tomographic data discussed above and used in the present method will normally comprise information pertaining to subregions of sections of the organ or part of tissue and the haemodynamic indices are determined for at least a substantial part of said subregions. The data of the subregions may be represented graphically as pixel values (as a gray-scale image or colour image of the section), and the quantitative haemodynamic parameter determined from the tomograpic data may also be represented as images subdivided into a plurality of pixels each representing a quantitative haemodynamic parameter pertaining to one of said subregions.

The present invention furthermore relates to a system for processing of time series of tomographic data pertaining to an organ or a part of tissue according to one or more of the above described methods according to the invention, said system residing on a computer having means for producing an output representative of at least some of the determined haemodynamic indices.

The present invention further relates to a method for evaluating the efficacy of a drug or a substance on an organ or on a part of tissue of a mammal by means of haemodynamic indices of said organ or of said part of tissue obtained by one or more of the methods according to the invention as described above. For this use, a system residing on a computer as described in the previous paragraph may advantageously be applied.

The present invention further relates to a method for obtaining information of the likelihood of recovery of an organ or part of tissue in a living mammal upon or during a period of insufficient vascular supply of said organ or of said part of tissue in the mammal comprising determining haemodynamic indices by one or more of the methods according to the invention as described above.

The present invention further relates to a method for obtaining information of the likelihood of progression of a chronic or neoplastic disease process of an organ or part of tissue in a living mammal affecting said organ or said part of tissue in the mammal comprising determining haemodynamic indices by one or more of the methods according to the invention as described above.

The present invention further relates to a method for obtaining information relevant for discrimination between relevant therapy of an organ or part of tissue in a living mammal upon or a period of insufficient vascular supply of said organ or of said part of tissue in the mammal comprising determining haemodynamic indices by one or more of the methods according to the invention as described above.

The present invention further relates to a method for obtaining information relevant for discriminating between relevant therapy of an organ or part of tissue in a living mammal upon the discovery of a chronic or neoplastic disease of said organ or of said part of tissue in the mammal comprising determining haemodynamic indices by one or more of the methods according to the invention as described above.

Furthermore, the present invention relates to the use of information obtained by use of one or more of the methods according to the invention as described above for preparing a reference table for use in discrimination of a treatment schedule for an individual mammal or group of mammals for which information have been obtained in a manner similar to said information.

The equipment for performing the tomographic data for use in the method according to the present invention is general standard equipment available to such an extent that the method can be applied in routine patient management. In addition, the determination may be performed easily and rapidly for healthy as well severely ill patients such as patients in coma. The method may be used for diagnosis and evaluation of possible further progress of disease whereby a suitable treatment schedule may be applied.

The present method is useful in connection with detection of heterogeneity of transit times, velocities or flows by means of external detection of tracers in general, whether in biological or technical systems. The technique is applicable to the diagnosis and study of a number of diseases, as well as in the development and subsequent monitoring of therapies in these diseases. Examples include:

(i) Diagnosis and treatment of diseases where, due to altered blood supply, tissue flow dynamics and thereby flow heterogeneity of an organ is altered, e.g. myocardial infarction, acute stroke, head trauma, subarachnoidal haemorrhage, migraine, carotid stenosis, dementia.

In particular the method may be used in connection with prediction/assessment of subsequent tissue damage based on heterogeneity measurements in the acute phase of myocardial or cerebral infarction, evaluation of drug efficacy in these diseases based on predictions as to the subsequent progression of the disease by heterogeneity measurements, and planning treatment based on prior knowledge of flow or transit time heterogeneity and the associated risk of amelioration of disease.

(ii) Diagnosis, study and treatment of diseases that alter or interfere with vascular architecture in any organ or pathological tissue, such that normal flow or transit time heterogeneity is disturbed, e.g.: (a) Angiogenesis (the formation of new vessels) by tumors, where the random formation of irregular vessels causes increased heterogeneity of flows and transit times due to the passage through irregular vascular paths. (b) Vasculopathies, i.e. diseases where normal vascular wall architecture is disrupted, altering the passage and thereby flow heterogeneity of blood or tracer molecules, such as collagen vascular diseases (Systemic lupus erythematosus, rheumatoid arthritis, other connective tissue disorders), vasculitis (giant cell arteriritis, polymylagia rheumatica), micro- and macroangiopathies in diabetes, angiopathy due to hypertension. (c) Changes in vascular architecture due to chronic or degenerative processes of organs (liver, kidneys, heart, brain) in general.

In particular the method may be used in connection with assessment of disease stage (e.g. tumor grade, extent of abnormal tone in renal afferent arterioles in hypertension or acute renal failure, extent of change in glomerular capillary structure in degenerative renal diseases) based on heterogeneity measurements, evaluation of drug efficacy in these diseases based on quantification of heterogeneity measurements (e.g. anti-angiogenic treatment), and planning treatment based on prior knowledge of flow or transit time heterogeneity and the associated risk of amelioration of disease.

In connection with organ transplantations it is generally of great value to know the vascular supply and the capacity of the vascular system of the organ.

(iii) The study of extraction of solutes in normal or diseased tissue as part of diagnosis or treatment. The technique can—given the capillary permeability of a particular solute—be applied to a given organ, providing the regional extraction of the solute. Examples include the study of oxygen, glucose or pharmaceutical uptake in the normal or diseased brain, e.g. acute or chronic ischemia, dementia, Parkinsons disease.

Accordingly, the invention relates to a method for identifying a condition relating to haemodynamic changes in an organ or tissue of a mammal, diagnosis of disease, treatment or prevention of disease, monitoring of disease, and for screening of a pharmaceutically active drug. The method involves use of the determination the tissue flow as described herein.

BRIEF DESCRIPTION OF THE DRAWINGS

The present invention will become more fully understood from the detailed description given hereinbelow and the accompanying drawings which are given by way of illustration only, and thus are not limitative of the present invention and wherein.

DETAILED DESCRIPTION OF PREFERRED METHODS ACCORDING TO THE INVENTION

Figure 1:
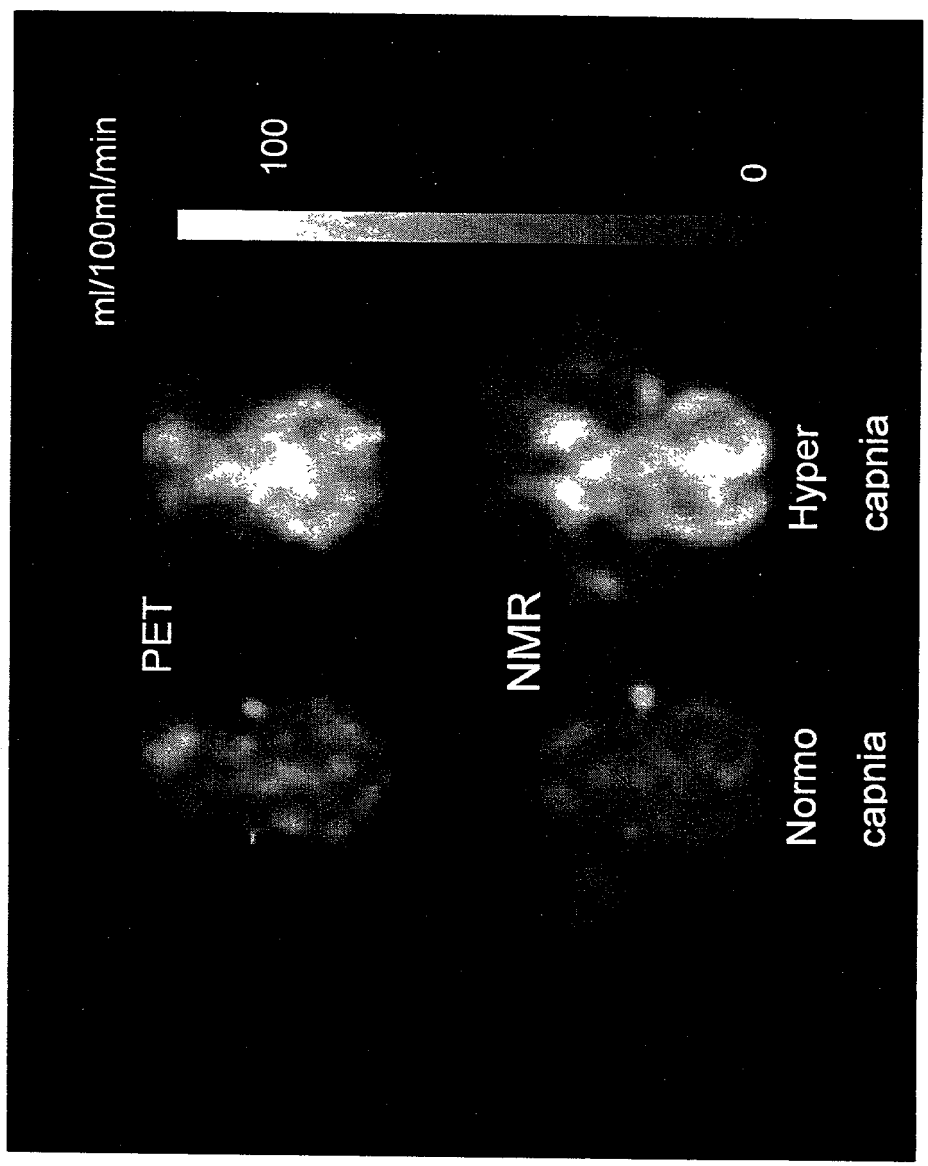
FIG. 1 shows parametric maps of CBF for pig no. 4.

The present method produces maps of normalised relative or absolute tissue blood flow, blood volume and absolute blood mean transit time from dynamic, tomographic images acquired during rapid bolus injection of a contrast agent or tracer that stays mainly intravascular in the organ.

By 'blood volume' is understood tracer or contrast agent distribution volume per tissue volume. If the distribution volume is less than that of total blood (e.g. only plasma), it is understood that conversion to absolute blood volume can be achieved by knowledge of regional distribution volume characteristics, e.g. haematocrit, or other normalisation by an independent techniques (e.g. positron emission tomography) as presented in this description. Likewise, 'blood flow' refers to flow of tracer or contrast agent distribution volume per tissue volume per unit time, with the aforementioned method of conversion to blood flow. Finally, 'transit time' refers to the time taken for tracer or contrast agent to traverse the image element, the arrival at which is defined from the arterial input measurement.

Furthermore, the method determines the distribution of flow and mean transit time, either in absolute values or relative to the mean value. The methods further allows the (i) comparison of relative flow distributions to that of normal tissue (here brain) or (ii) quantification of absolute flow distributions in terms of the associated extraction of a substance with known capillary permeability.

With the resolution of some tomographic imaging techniques, the dimensions of vessels are too small to accurately determine arterial tracer concentration levels non-invasively.

Instead, image elements containing partly tissue, partly blood vessels, must be used in order to characterise the mere shape of the arterial input curve to the tissue. In such cases, absolute values of flow and volume cannot be found, and therefore a normalisation routine allowing (a) comparison of serial measurements in a single subject, (b) comparison among subjects and (c) absolute quantification the case of susceptibility MRI of the brain is described below.

Overview

The techniques consist of the following steps:

A. Conversion of tomographic images into images representing concentrations of contrast agent as a function of time.
B. Identification of relative or absolute (i.e. in units identical to those of the tomographic images after the above mentioned conversion) arterial tracer concentrations from the image data.
C. In the case of relative arterial tracer concentrations, normalisation of the arterial input area to the injected dose of contrast agent per kg body weight.
D. Optional correction of tissue tracer curves for delays.
E. Determination of
   (i) absolute or relative tissue blood flow
   (ii) tissue impulse response function
      by deconvolution of tissue concentration time curves by the arterial tracer concentration in each image element.
F. Determination of tissue blood volume by determining the area under the tissue first-pass concentration curve.
G. Determination of tissue mean transit time by the tissue blood volume—blood flow ratio.
H. In the case of MR susceptibility contrast imaging using Gd-chelates in brain tissue, conversion to absolute blood flow and blood volume by a pre-determined constant.
I. Determination of the distribution of flow or transit times in each image element from the residue function (normalised impulse response function) determined in E.
J. Comparison of distributions of relative flows to a predetermined distribution found for a normal organ, here brain.
K Quantification of the distribution of flows in terms of the extraction fraction of a given solute with specified capillary permeability, in cases where imaging is performed with MR imaging with microvascular weighting, or microvascular volume can otherwise be inferred from total blood volumes.

1. Conversion of Tomographic Data into Tracer Concentration Images

The method and associated software handles various modalities, depending on whether tracer injection changes signal intensity from baseline in a linear or logarithmic fashion upon tracer arrival. With a specified option, acquired tomographic images during tracer bolus injection are converted into concentrations as a function of time, with measurement time points spaced equally in time.

1.1. In the case of MR images, weighted towards the transverse relaxation times ($T_2$ or $T_2'$), (typically acquired in brain), the tissue concentration as a function of time, $C_t(t)$, is typically obtained by the formula $$C_t(t) = -k \cdot \log\left(\frac{S(t)}{S(t_o)}\right) / TE \qquad \text{Eq. 1}$$

where $S(t_o)$ is the signal intensity before contrast injection (formed as the average of signal intensities up to tracer arrival), $S(t)$ is the signal intensity at time t, and TE is the echo time used in the sequence. Here, k is a constant characteristic of the tissue and contrast agent.

1.2. In the case of MR images weighted towards the longitudinal relaxation time ($T_1$) images (typically acquired for intravascular tracers in the heart), concentrations are assessed directly by the change in longitudinal relaxation rate, $\Delta R_1$, as derived from signal intensity changes $$C_t(t) = \Re \cdot \Delta R_1 \qquad \text{Eq. 2}$$

where $\Re$ is the relaxivity of the applied contrast agent.

1.3. In the case of Computed Tomography (CT) images, concentrations are assessed by the change in image intensity, measured in Hounsfield units, $\Delta H$ $$C_t(t) = \kappa \cdot \Delta H \qquad \text{Eq. 3}$$

where $\kappa$ is the characteristic X-ray absorption of the contrast agent.

2. Identification of Arterial Vessels

For identification of arterial vessels in the image, the algorithm provides the choice of first producing an image that guides this process (2.a.), or proceeding directly to calculation of tissue flow (2.b.)

2.a. If so specified by an option, the concentration time curve of each image element is fitted to a gamma variate function by nonlinear least-squared regression (by means of a fletcher-algorithm) over the time interval until visible tracer re-circulation occurs (the re-circulation is specified by the user, determining
   (a) Tracer arrival time
   (b) Area under first pass (this quantity is proportional to the local blood volume).

These two quantities are stored as floating point binary image file, allowing visualisation as an image where each image pixel corresponds to quantities (a) and (b), respectively. An artery is then visually identified in these images by
   (a) Anatomical location.
   (b) Early tracer arrival relative to the arrival in tissue.
   (c) Large area under first pass (corresponding to a large blood volume and thereby a large portion of the vascular volume being contained in a voxel).

2.b. By observing images of tracer concentration as a function of time in a tool that allows visualisation of the time-course of single pixels, arterial levels can be identified.

Upon identification of the arterial input function, the corresponding signal intensity time curve is fed to the program below in the form of an ASCII file.

3. Normalisation of Arterial Input to Allow Comparison of Serial Measurements

In cases where arterial concentrations are not known in the units of tissue concentrations the algorithm includes a method to allow comparison of relative tissue blood flow and tissue blood volume in serial examinations in the same subject or animal. In order to achieve this, the area of the arterial input function (as determined by gamma variate fitting above) is set equal to the injected dose (in millimoles) normalised per body weight prior to the deconvolution below. Likewise, subsequent blood volume measurements are divided by the aforementioned, dose-corrected arterial input area.

4. Determination of Blood Volume

Using known tracer kinetic principles, relative blood volume is determined as the area under the tissue concentration time curve corresponding to the first-pass of the injected tracer or contrast agent (See e.g. FIG. 2 in Example 1), normalised to the arterial input area determined in 3. The area is determined both by direct, numerical integration, and by gamma variate fitting (See section 2).

5. Determination of Blood Flow and Mean Transit Time

Tissue flow, $F_t$, is determined as the solution to the equation $$C_t(t) = F_t \cdot C_a(t) R(t) \qquad \text{Eq. 4}$$

where ⊗ denotes convolution, $C_a(t)$ is the arterial concentration as a function of time, and $R(t)$ is the residue function, describing the fraction of particles still present in the vasculature at time t after a unit impulse input.

Mean Transit time (MTT) is given from the blood volume (V) and $F_t$ the central volume theorem $$MTT = \frac{V}{F_t} \qquad \text{Eq. 5}$$

With tissue and arterial concentrations measured at equidistant time points $t_1$, $t_2 = t_1 + \Delta t$, ..., $t_N$, Equation 4 can be reformulated as a matrix equation $$\begin{pmatrix} C_t(t_1) \\ C_t(t_2) \\ \ldots \\ C_t(t_N) \end{pmatrix} = F_t \cdot \Delta t \begin{pmatrix} C_a(t_1) & 0 & \ldots & 0 \\ C_a(t_2) & C_a(t_1) & \ldots & 0 \\ \ldots & \ldots & \ldots & \ldots \\ C_a(t_N) & C_a(t_{N-1}) & \ldots & C_a(t_1) \end{pmatrix} \cdot \begin{pmatrix} R(t_1) \\ R(t_2) \\ \ldots \\ R(t_N) \end{pmatrix} \qquad \text{Eq. 6}$$

The equation is (after applying Simpsons rule to the matrix elements (Østergaard 1996b)) solved for $F_t \cdot R(t)$ in each pixel by Singular Value Decomposition (SVD), with a cut-off in diagonal eigenvalues at 20% of the maximum value in order to suppress experimental noise typical of tomographic images (signal to noise ratio of the order of 10). The noise cut-off of 20% is user specified. In the case of higher signal-to-noise ratio (SNR) or specific SNR characteristics, a Monte Carlo simulation scheme is provided to optimise the cut-off (Østergaard 1996b).

The algorithm allows independent correction for tracer arrival delays prior to deconvolution by shifting the tissue curve in a given pixel by the delay fitted in 2.a., thereby reducing bias in flow rates due to simple delays of the tissue curve relative to the arterial input curve (Østergaard 1996a).

The algorithm calculates the following quantities, and stores them as digital, floating point images:
 (a) Tissue blood volume (As determined section 2.a. and 4).
 (b) Tissue blood volume (As determined by simple, numerical integration up to tracer re-circulation—section 4).
 (c) Blood mean transit time determined as the area under the residue function response R(t).
 (d) Relative or absolute tissue flow as determined by the maximum value of the impulse response function (Ft-R(t))—Section 5.
  Here, relative flow, $F_r$, means a value proportional to (by the same factor throughout the digitised images of relative flows) absolute flow in cases where absolute arterial flow values cannot be determined. Again, absolute flow refers to cases where arterial concentrations are known in the units of the tissue concentration data.
 (e) Relative or absolute tissue flow as determined by Equation 5, using the blood volume determined in (b) divided by the MTT determined in (c).
  Here, relative flow means a value proportional to (by the same factor throughout the digitised images of relative flows) absolute flow in cases where absolute arterial flow values cannot be determined. As above, an absolute flow refers to the cases where arterial concentrations are known in the units of the tissue data.
 (f) MTT determined as tissue blood volume (b) divided by tissue flow (d) (Equation 5)
 (g) The tissue residue function, R(t).
 (h) The goodness of fit, $\chi^2$, of Equation 4 to the tissue concentration time curve.

6. Absolute Quantification

To allow absolute quantification of cerebral blood flow (CBF; ml/100 ml/min) or cerebral blood volume (CBV, ml/100 ml) measurements with Gd-chelates and dynamic $T_2$ weighted susceptibility contrast agents values are determined as $CBF = 0.87 \cdot B_o \cdot F_r$ (humans)
 $CBV = 0.87 \cdot B_o \cdot V_r$ (humans)
 $CBF = 1.09 \cdot B_o \cdot F_r$ (porcine data)
 $CBV = 1.09 \cdot B_o \cdot V_r$ (porcine data)

Where $B_o$ is the field strength of the magnet in Tesla, and $V_r$ and $F_r$ are the relative volumes and flows determined as described in section 4 and 5, respectively, where impulse response height and tissue curve area have been appropriately corrected for the arterial input area.

7. Determining the Distribution of Transit Times

To determine the distribution of tissue transit times, h(t), the negative slope of the tissue residue function is determined in each point as the average of slopes of straight lines connecting the previous and following point on the R(t) curve (See Equation 21 and Equation 22).

Special Cases:
 7.a. At the initial point of R(t), where only one slope can be defined, the slope of the straight line connecting the initial and second measurement of R(t) is chosen
 7.b. In cases where, due to noise, R(t) between to points deviates from being either constant or decreasing as a function of time, the slope is set to zero.

The resulting curve, with the time axis normalised to the mean transit time, is illustrated in Example 2 (Østergaard 1998a).

8. Determining the Distribution of Relative Flows.

In the remainder of the description, relative flows refer to a defined fraction of the mean flow, i.e. a dimensionless quantity, independent of any absolute quantification of flow.

Under the assumption of equal lengths of capillary paths, the distribution of transit times can be converted into a distribution w(f) of relative flows f (i.e. flows normalised such that the mean of the distribution is 1) by the relation $$f \cdot F_t = \frac{V}{t} \qquad \text{Eq. 7}$$

where V is the associated blood volume (Units of V and $F_t$ may here be arbitrary due to the normalisation in Equation 9), and thereby $$w(f) = -\frac{t}{f} \cdot h(t) \qquad \text{Eq. 8}$$

where t is a given transit time in the distribution above, h(t) the corresponding negative slope of R(t) and dt is given by the time resolution of the measurements (and thereby R(t)).

Its is finally required that the resulting curve w(f) be a probability density function (PDF), i.e. has area 1, and has mean value 1 (i.e. describes flows relative to total flow), i.e.

$$\int_0^\infty w(f)f df = \int_0^\infty w(f) df = 1 \qquad \text{Eq. 9}$$

This is achieved by iteration, numerically integrating the expressions of w(f) and f above, in each step dividing f and w(f) by the preceding integral.

9. Determining Abnormal Flow Distributions

Figure 13A:
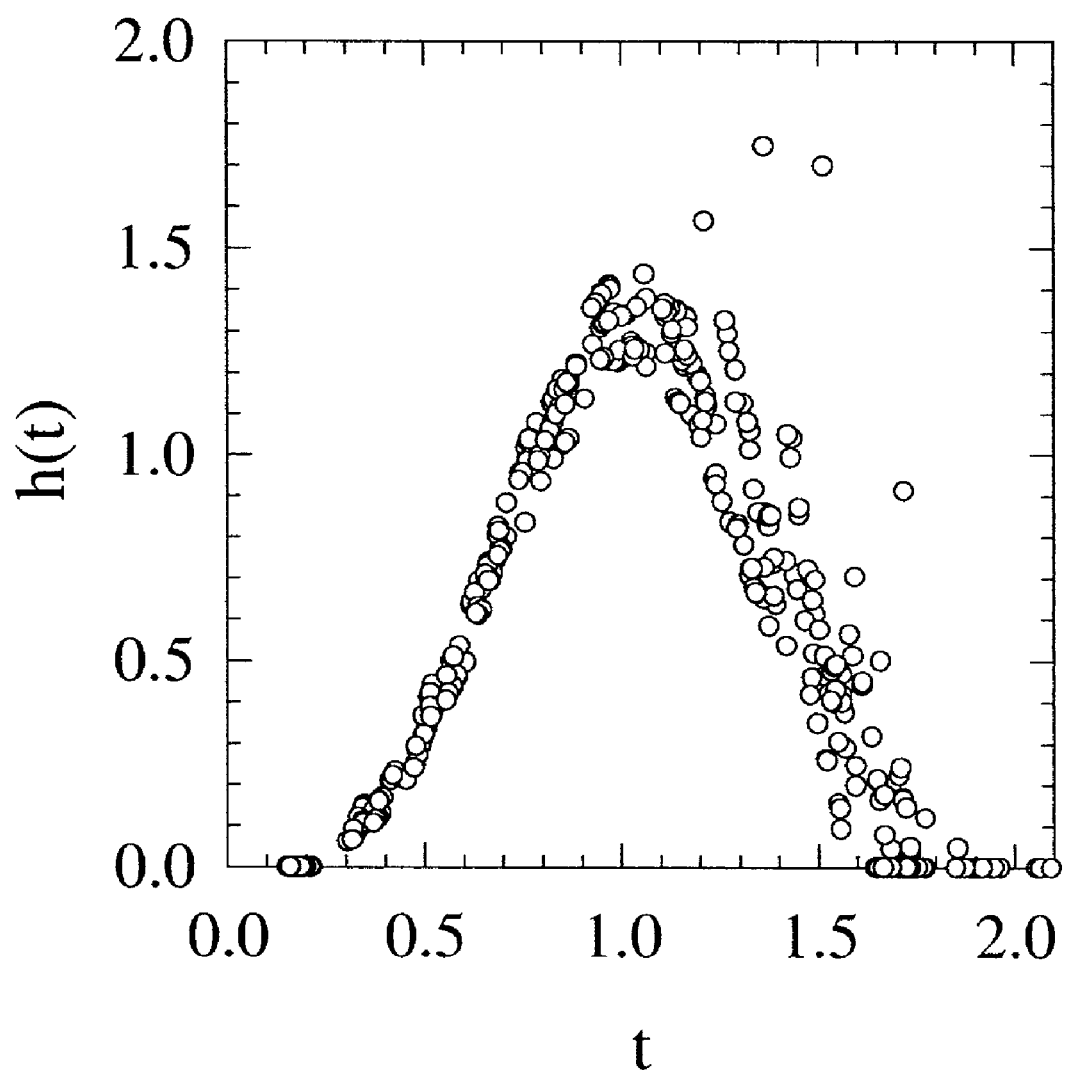
FIG. 13a shows all pairs of relative transit time t and corresponding h(t) measured for all regions in all 6 volunteers.
Figure 13B:
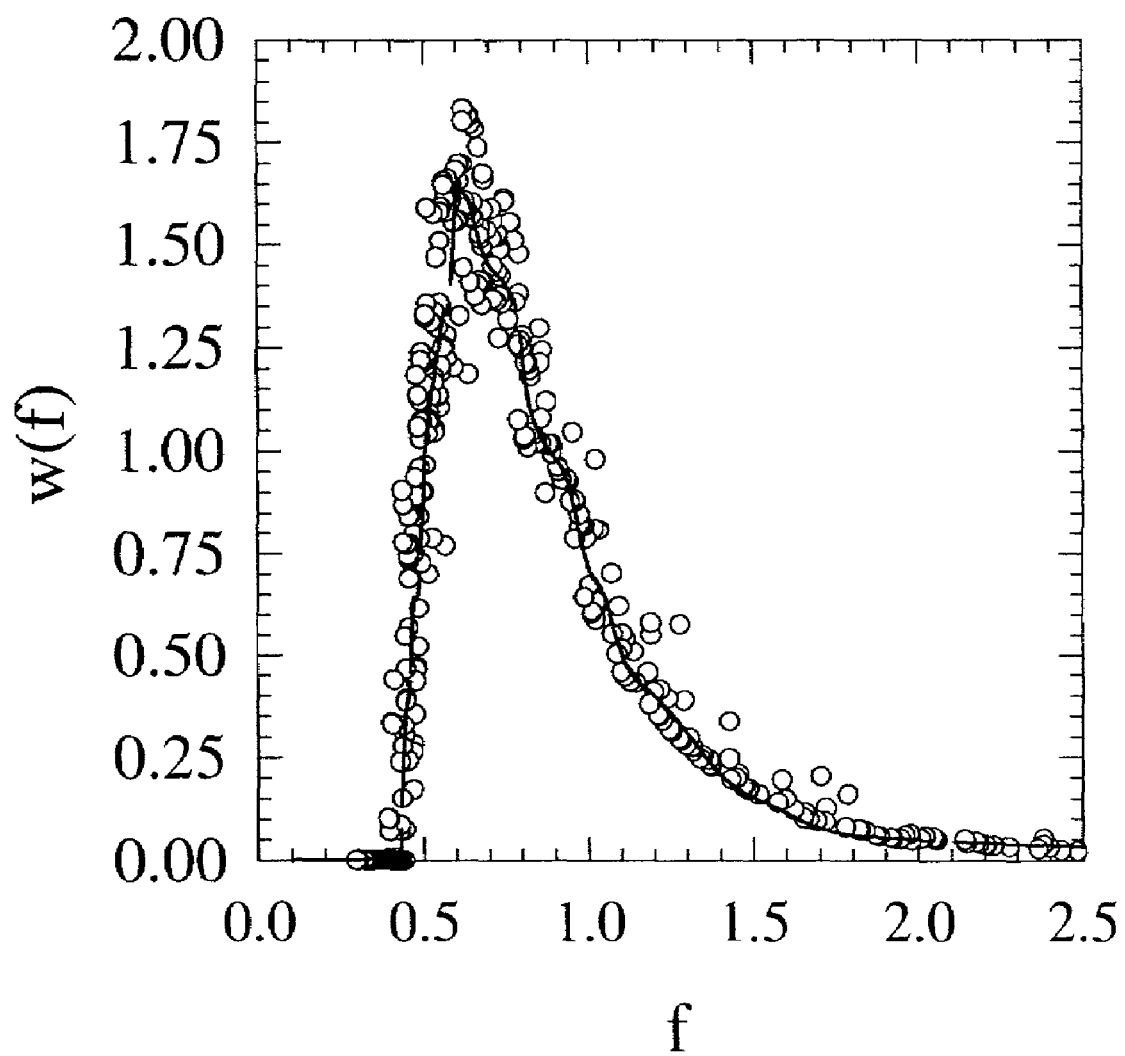
FIG. 13b shows under the assumption of equal capillary lengths the corresponding plot of relative flow f and w(f) measured for all regions and volunteers.

The resulting distribution of relative flows is recalculated by linear interpolation to determine its values at predefined relative flow values previously determined for normal tissue (FIG. 13b in Example 3).

The values read

TABLE 1

| f | w(f) | f | w(f) |
|---|---|---|---|
| 3.8053 | 1.65E-03 | 0.6941 | 1.4594 |
| 2.865 | 0.0226 | 0.647 | 1.5915 |
| 2.3306 | 0.0372 | 0.6205 | 1.6279 |
| 1.7879 | 0.0627 | 0.5969 | 1.5812 |
| 1.5881 | 0.1198 | 0.5815 | 1.351 |
| 1.4459 | 0.1751 | 0.565 | 1.3393 |
| 1.3535 | 0.2491 | 0.5448 | 1.2367 |
| 1.2785 | 0.3303 | 0.5262 | 1.1433 |
| 1.1912 | 0.4058 | 0.5133 | 1.0688 |
| 1.1106 | 0.4793 | 0.5007 | 0.928 |
| 1.0474 | 0.646 | 0.4822 | 0.6559 |
| 0.9972 | 0.7218 | 0.4689 | 0.6366 |
| 0.9438 | 0.9032 | 0.4571 | 0.4282 |
| 0.8981 | 0.986 | 0.4416 | 0.3133 |
| 0.8214 | 1.1098 | 0.4316 | 0.0244 |
| 0.7794 | 1.3562 | 0.42 | 0 |

In each image element, the distribution is compared to this standard curve by means of a nonparametric Kolmogorov Smirnov (KS) test, and the corresponding p value is calculated.

The program returns digitized images of 8.a. The KS probability p as a quantitative measure of deviation from the normal distribution.

8.b. 20 images containing the values of w(f) at the predefined values f in Table 1.

8.c. With a specified option, corresponding comparison of the distribution of relative transit times is performed (with the curve in FIG. 13a in Example 3), and the transit times or relative transit times displayed.

10. Absolute Quantification of Flow heterogeneity and Solute Extraction

With a specified option, for susceptibility contrast MR imaging, the program combines the relative flow heterogeneity w(f) with absolute flow estimates (See Section 5) to calculates distribution of absolute flows in ml/1100 ml/min. Furthermore, using the microvascular weighting (For example as demonstrated in Example 1 or in Østergaard 1998c) and table values for the microvascular dimensions of the organ in question (for brain capillaries e.g. 8 µm diameter and 120 µm length), blood volume is converted into capillary surface area, S. The local extraction E of a substance with capillary permeability P (as given by literature values), is then given by:

$$E = \int_0^\infty w(f)\left(1 - e^{-\frac{PS}{f F_t}}\right) df \qquad \text{Eq. 10}$$

This quantity is visualised as a separate image, based on the specified value of P. In cases where tomographic images do not possess a specific microvascular weighting, S can be inferred from the blood volume by literature values describing microvascular dimensions and fractions for the relevant organ.

EXAMPLE 1

Absolute Cerebral Blood Flow and Blood Volume Measured by MRI Bolus Tracking: Comparison with Pet Values Summary of the Example Cerebral blood flow (CBF) was determined with magnetic resonance imaging (MRI) of contrast agent bolus passage, and compared the results to those obtained by positron emission tomography (PET). Six pigs were examined by MRI and PET under normo- and hypercapnic conditions. After dose normalisation and introduction of an empirical constant $\Phi_{Gd}$, absolute regional CBF was calculated from MRI. The spatial resolution and the signal-to-noise-ratio of CBF measurements by MRI were better than by the $H_2^{15}O$-PET protocol.

MRI Cerebral Blood Volume (CBV) estimates obtained using this normalisation constant correlated well with $C^{15}O$-PET CBV values However, PET CBV values were about 2.5 times larger than absolute MRI CBV values, supporting the hypothesised sensitivity of MRI to small vessels.

Background

Rapid magnetic resonance imaging of the passage of a bolus of magnetic susceptibility contrast agent has become an important tool for assessing regional cerebral blood volume (CBV, 'perfusion') (Rosen et al., 1990; Rosen et al., 1991). This technique has gained widespread acceptance in the evaluation of certain types of haemodynamic changes in cerebral pathologies, especially stroke (Sorensen et al., 1996) and CNS tumors (Aronen et al. 1994).

With regard to cerebral blood flow (CBF) determined from contrast bolus passage, there has been uncertainty whether CBF can be measured reliably with MRI, due to inherent theoretical problems (Lassen, 1984; Weisskoff, 1993). Recent results indicate that MRI can be used to measure CBF, in that mean gray:white matter flow ratios measured by dynamic spin echo (SE) echo planar imaging (EPI) in normal humans were similar to PET literature ratios for CBF for age-matched subjects (Østergaard et al. 1996a; Østergaard et al 1996b). The bolus technique has only been able to yield relative CBF values within a given subject. In this report, we present a procedure for determining absolute CBF values by means of MRI. We compared the CBF values to the results of the PET [$^{15}$O] water clearance method in hypercapnic animals. We also studied the microvascular sensitivity of MRI CBV measurements, comparing quantitative CBV measured with MRI by our approach, and PET [$^{15}$O]CO estimates of vascular volume.

Theory

MRI CBF Measurements

A detailed discussion of the method of measurement of CBF by MR imaging of nondiffusible tracers is presented elsewhere (Østergaard et al., 1996b). In brief, the concentration $C_{VOI}(t)$ of an intravascular contrast agent within a given volume of interest (VOI) can be expressed as $$C_{VOI}(t) = F \cdot \int_0^t C_a(\tau) R(t-\tau) d\tau \qquad \text{Eq. 11}$$

where $C_a(t)$ is the arterial input, F is tissue blood flow and R(t) is the vascular residue function, i.e. the fraction of tracer present in the vascular bed of the VOI at time t after injection of a unit impulse of tracer in its supply vessel. By treating the residue function as an unknown variable, this approach circumvents the problems of using intravascular tracers for CBF measurements pointed out by Lassen (1984) and Weiskoff et al. (1994). Assuming that tissue and arterial concentrations are measured at equidistant time points $t_1$, $t_2 = t_1 + \Delta t$, . . . , $t_N$, this equation can be reformulated as a matrix equation $$\begin{pmatrix} C_{VOI}(t_1) \\ C_{VOI}(t_2) \\ \ldots \\ C_{VOI}(t_N) \end{pmatrix} = CBF \cdot \Delta t \begin{pmatrix} C_a(t_1) & 0 & \ldots & 0 \\ C_a(t_2) & C_a(t_1) & \ldots & 0 \\ \ldots & \ldots & \ldots & \ldots \\ C_a(t_N) & C_a(t_{N-1}) & \ldots & C_a(t_1) \end{pmatrix} \cdot \begin{pmatrix} R(t_1) \\ R(t_2) \\ \ldots \\ R(t_N) \end{pmatrix} \qquad \text{Eq. 12}$$

and solved for CBF·R(t) by algorithms from linear algebra. Østergaard et al. (1996a) demonstrated that, by using singular value decomposition (SVD), R(t) and CBF can be determined with good accuracy, independent of the underlying vascular structure and volume, and with raw image signal to noise ratios (SNR) equivalent to those obtainable in current clinical MR imaging protocols.

MRI CBV Measurement

Vascular volume was determined by numerically integrating the area under the concentration time curve during the contrast bolus $$CBV \propto \int_{bolus} C_{VOI}(\tau) d\tau \qquad \text{Eq. 13}$$

(Stewart, 1894). Absolute tracer concentrations are not readily available by means of the susceptibility contrast measurements used in this study (See below). However, as CBF and CBV are obtained from the same, arbitrary concentration units, the empirical constant that yields true, absolute CBF found below will also provide absolute CBV values.

PET CBF Measurement.

The regional uptake of a diffusible tracer is described by the equation introduced by Ohta et al. (1996):

$$C_{VOI}(t) = (1-V_0) \cdot K_1 \cdot \int_0^t C_a(\tau) e^{-k_2(t-\tau)} d\tau + V_0 \cdot C_a(t) \qquad \text{Eq. 14}$$

where, by assumption, $K_1$=CBF for freely diffusible tracers and $$k_2 = \frac{K_1}{V_e},$$

where $V_e$ is the partition volume of the tracer. $V_0$ is the vascular distribution volume for the tracer in the tissue.

Material and Methods

Animal Preparation and Experimental Protocol

Six female country-bred Yorkshire pigs weighing 38–45 kg were used in the experiments. Prior to the experiment, the pigs were housed singly in stalls in a thermostatically controlled (20° C.) animal colony with natural lighting conditions. The pigs had free access to water but were deprived of food for 24 hours prior to experiments. The project was approved by the Danish National Committee for Ethics in Animal Research. Pigs were initially sedated by i.m. injection of 0.25 ml/kg of a mixture of midazolam (2.5 mg/ml) and ketamine HCl (25 mg/ml). A catheter was then placed in an ear vein. After i.v. injection of additional midazolam/ketamine mixture (0.25 ml/kg), the pig was intubated and artificially ventilated (Engström, Sweden) throughout the experiment, maintaining anaesthesia by continuous infusion of 0.5 ml/kg/hr of the midazolam/ketamine mixture and 0.1 mg/kg/hr pancuronium. Indwelling femoral arterial and venous catheters (Avanti® size 4F–7F) were surgically installed. Infusions of isotonic saline (approx. 100 ml/hr) and 5% glucose (approx. 20 ml/hr) were administered i.v. throughout the experiments. Throughout the PET-experiment, body temperature, blood pressure, heart rate and expired air $CO_2$ levels were monitored continuously (Kivex, Ballerup, Denmark), and arterial blood samples withdrawn and analysed (ABL 300, Radiometer, Copenhagen) at regular intervals to monitor blood gases and whole blood acid-base parameters. In the MR-scanner, expired air $CO_2$ was monitored continuously (Datex Capintec 2000). Hypercapnia was induced by decreasing respiratory rate and tidal volume. The animal was allowed one hour to equilibrate to a steady $P_aCO_2$ level. At the end of experiments, the anaesthetised pigs were killed in accordance with the regulations of the Danish National Ethics Committee for Animal Experiments.

MRI Imaging Protocol

Imaging was performed using a GE Signa Horizon 1.0 Tesla imager (GE Medical Systems, Europe). Following a sagittal scout, a $T_1$-weighted 3D gradient echo sequence (time of repetition–TR=8 ms, time of echo–TE=1.5 ms, 20° flip angle) was acquired for later co-registration of MR and PET data. For dynamic imaging of bolus passages, spin echo (TR=1000 ms TE=75 ms) single shot echo planar imaging (EPI) was performed, starting 30 seconds prior to injection. A 64×64 acquisition matrix was used with a 14×14 cm coronal field of view (FOV), leading to an in-plane resolution of 2.2×2.2 mm². The slice thickness was 6 mm.

In all experiments, bolus injection of 0.2 mmol/kg Gadodiamide (OMNISCAN®, Nycomed Imaging, Oslo, Norway) was performed manually at a rate of 15–20 mils. Prior to the first dose, a pre-dose of 0.05 mmol/kg was given to avoid systematic effects from changes in blood $T_1$.

MRI Image Analysis

We used susceptibility contrast arising from compartmentalisation of the paramagnetic contrast agent (Villringer et al., 1988) to determine tissue and arterial tracer levels. We assumed a linear relationship (Weisskoff et al., 1994) between paramagnetic contrast agent concentration and the change in transverse relaxation rate $\Delta R_2$, so as to determine tissue and arterial tracer time concentration curves C(t) according to the equation $$C(t) \propto \Delta R_2(t) = -\log\left(\frac{S(t)}{S(0)}\right) / TE \qquad \text{Eq. 15}$$

where S(O) and S(t) are the signal intensities at the baseline and time t, respectively. Notice that we assumed $T_1$ to be unaltered during the bolus injection. Notice that this equation does not provide absolute concentrations. In our approach, we fixed the relation between susceptibility contrast and tracer concentration by requiring MR flow rates in susceptibility contrast units to equal absolute flow rates measured by PET. The resulting constant of proportionality, $\Phi_{Gd}$, is the used to calibrate MR measurements of both CBF and CBV to absolute values.

The arterial concentration was determined in each animal from pixels containing large, feeding vessels (typically the middle cerebral artery) showing an early and large (3–10 times that of gray and white matter) increase in $\Delta R_2$ following contrast injection. This method has previously been demonstrated to closely reflect actual, arterial levels for the susceptibility contrast agents used in this study when imaged using spin echo EPI techniques (Porkka et al., 1991). The integrated area of the arterial input curve was in each measurement normalised to the injected contrast dose (in mM per kg body weight) in order to compare within and among animals.

To determine CBF from equation 12, the deconvolution was performed over the range of measurements where the arterial input values exceeded the noise level (usually about 15 seconds). Deconvolution followed smoothing of raw image data by a 3×3 uniform smoothing kernel to the. The maximum of the deconvolved response curve was assumed proportional to CBF. CBV was determined by numerically integrating the concentration time curve from bolus arrival to tracer re-circulation.

PET Radiochemistry $^{15}O_2$ was produced by the $^{14}N(d,n)^{15}O$ nuclear reaction by the bombardment of nitrogen gas with 8.4 MeV deuterons using a GE PETtrace 200 cyclotron. $^{15}O_2$ was mixed with hydrogen and passed in a stream of nitrogen gas over a palladium catalyst at 150° C. to produce $^{15}O$-water vapour, which was trapped in 10 ml sterile saline. $^{15}O$—CO was prepared by passing $^{15}O_2$ in a stream of nitrogen gas over activated carbon at 900° C. The $^{15}O$—CO was piped directly to a 500 ml vial in a dose calibrator situated close to the PET scanner. Upon decay to the required radioactivity, the $^{15}O$—CO was administered to the pig as described below. $^{15}O$-Butanol was prepared by the reduction of $^{15}O_2$ with tri-n-butyl borane immobilised on an aluminum solid phase matrix. The product was purified by transfer of the resulting radioactivity with 10 ml $H_2O$ onto a C18 solid phase extraction column. The $^{15}O$-butanol was subsequently eluted into a sterile vial with 10 ml 20% ethanol.

PET Imaging Protocol

The pigs were studied lying supine in the scanner (Siemens ECAT EXACT HR) with the head in a custom-made head-holder. The position of the head was checked throughout the experiment with laser markers. To measure CBF, i.v. injection 800 MBq $H_2^{15}O$ was performed, followed immediately by an i.v. injection of 3–4 ml of heparin solution (20 IU/1 l isotonic saline) to flush the catheter. We acquired a sequence of 21 (One sample every fifth second for 60 s, one sample every tenth second for one minute and one sample every $20^{th}$ second for 1 minute) arterial blood samples (1–2 ml) and 12 PET brain images (One image every tenth second for one minute, one image every $15^{th}$ s for one minute and one image every $30^{th}$ s for the remaining 60 s). To measure CBV, we administered 800 MBq $^{15}O$ labeled CO mixed with oxygen to a 1 l volume by syringe. Following ten seconds breath-hold, normal ventilation resumed. To assess the variability of repeated CBF results, an additional injection of $^{15}O$-butanol was performed in one pig, using the imaging and blood sampling scheme described above. For all experiments, total radioactivity in blood samples was measured, and image as well as arterial data were corrected for the half-life of $^{15}O$ (123 s). PET image data were reconstructed using a Hann filter with a cutoff frequency of 0.5 pixel$^{-1}$, resulting in a spatial resolution (FWHM) of 4.6 mm. Correction for attenuation was made on the basis of the transmission scan.

PET Image Analysis

High SNR PET data were used to co-register PET and MR data using REGISTER (courtesy David McDonald and Peter Neelin, Montreal Neurological Institute, McGill University, Montreal, Canada). Raw PET image data were then transformed and re-sampled to the same spatial location and resolution as the MR data to allow direct comparison of the two techniques. Following the application of the 3×3 uniform smoothing kernel to the raw PET images, the $^{15}O$ water data was fitted to equation 14 using non-linear, least squared regression analysis of each image voxel. CBV was determined by the ratio of cerebral and arterial whole blood $^{15}O$ CO levels after initial distribution (30 seconds) of the tracer. We assumed that the mean brain-to-systemic haematocrit ratio is 0.68 (Lammertsma et al., 1984). To correct for slightly different $P_aCO_2$ levels in the MRI and PET normo- and hypercapnic conditions, respectively, the PET CBF and CBV maps were corrected to the $P_aCO_2$ of the MRI measurements. We assumed a linear relationship between $P_aCO_2$, and CBV and CBF, respectively (Grubb et al., 1974), i.e.

$$CBF = a \cdot P_aCO_2 + b$$

The two constants a and b were determined for each pixel, and CBV and CBF were corrected.

Comparison of PET and MR Parameter Images

MRI CBF maps were filtered using a 4.5 mm FWHM gaussian filter to make the spatial resolution of PET and MR maps approximately identical. Pixel maps of CBF (at similar anatomical locations and pixel size) generated with PET and MRI were then compared on a regional basis for the normo- and hypercapnic condition. In each image, 10–12 regions of interest (ROI) of similar size were chosen. Average regional CBF values and their standard deviations (derived from the pixels within the ROI) for the normo- and hypercapnic conditions were then plotted versus the corresponding PET CBF values to examine the appropriateness of a linear relationship between the two estimates. Linear least squared regression analysis was performed to determine the slope and y intercept of the linear fit Finally, to test whether a common conversion factor yields absolute CBF by MRI, 2-way ANOVA was performed, comparing the slope and its standard deviation for each pig to the remaining pigs.

Results

By averaging regional MRI CBF values (As determined by equation 12 and 15) and $^{15}O$ water PET CBF values (in ml/100 ml/min) for all pigs (for both normo- and hypercapnic conditions), a conversion factor of $\Phi_{Gd}=1.09$ was found. In the remaining analysis, all MR flow rates were multiplied by this factor.

FIG. 1 shows parametric maps of CBF for pig no. 4. The pixel size is the same in the two images. Notice the good overall agreement between the regional values and responses to arterial $CO_2$ levels using the two methods, although the MRI CBF map appears to distinguish better between gray and white matter structures than the PET CBF maps. Notice also that the PET CBF map appears to be somewhat noisier than the MRI CBF map. We investigated possible regional differences in CBF maps obtained by the two methods. These appeared to be mainly associated with either noise artifacts or the presence of veins in the PET image slice. Noise in PET images appears as 'streaky artifacts' that sometimes propagate into the CBF maps. Veins, on the other hand, are often interpreted by the kinetic model in equation 13 as a high flow region, whereas they are rarely detected by the MR sequence.

Figure 2:
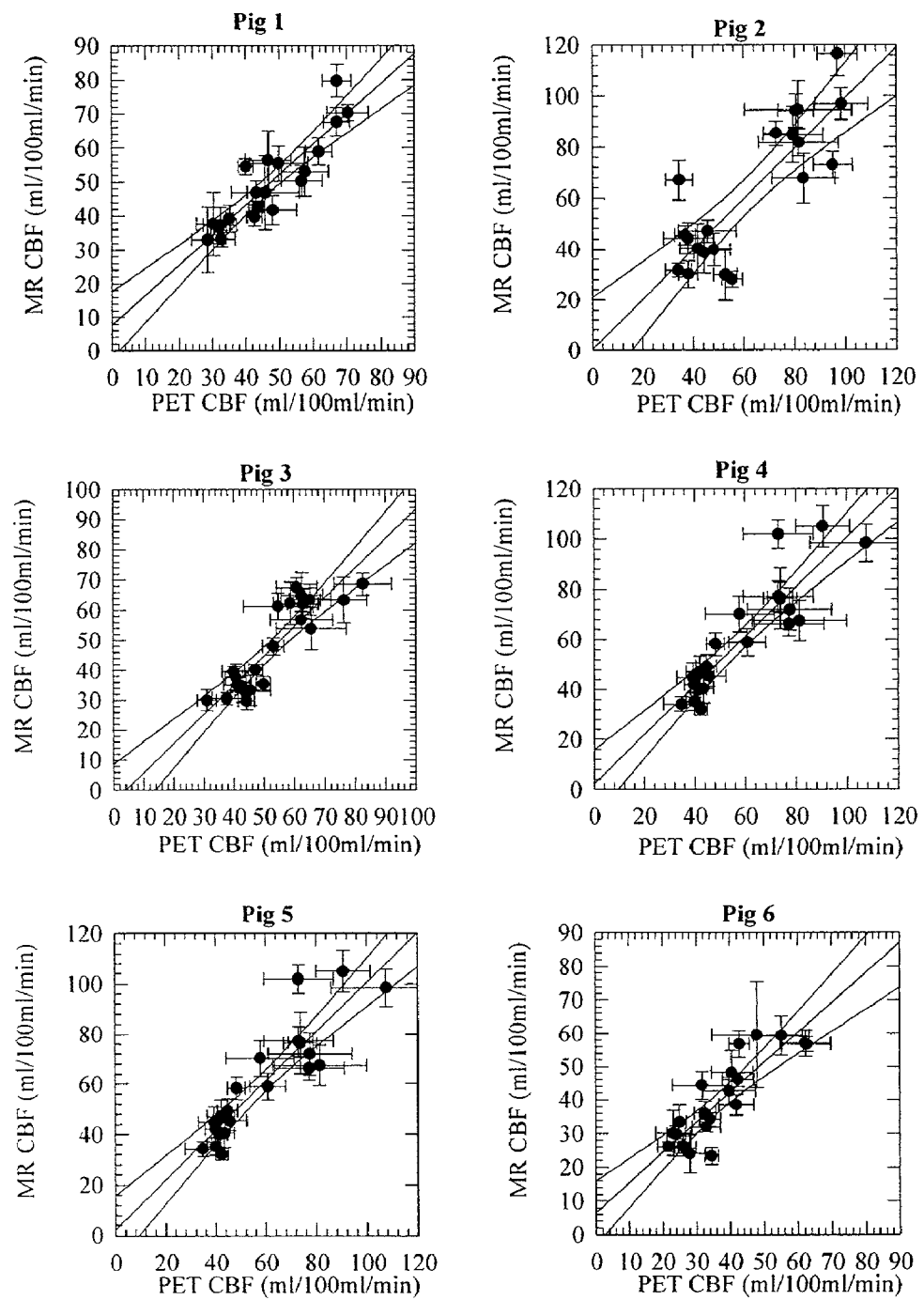
FIG. 2 shows plots of regional CBF values with their standard deviations for individual pigs.
Figure 3:
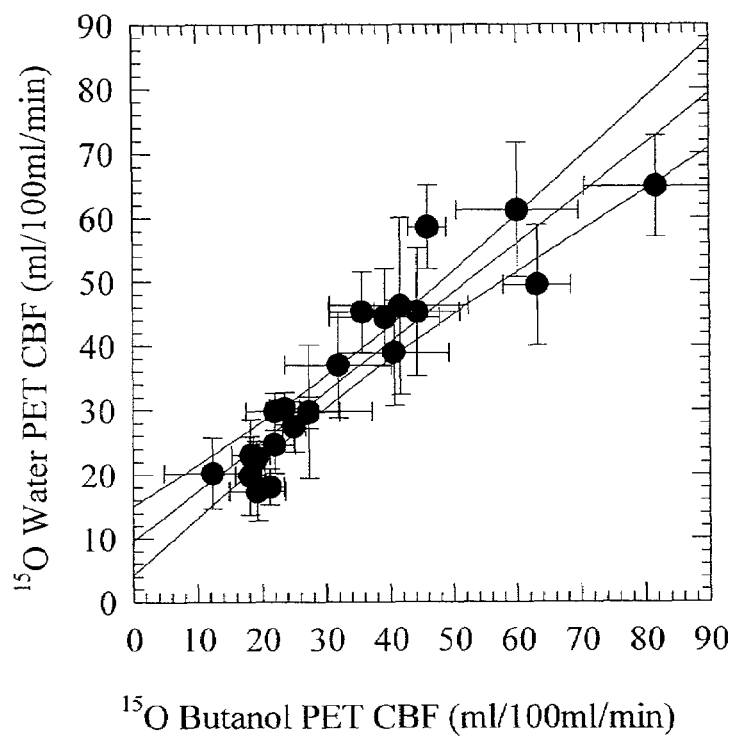
FIG. 3 shows the corresponding plot for repeated PET measurement of CBF with $^{15}O$ butanol.

FIG. 2 shows plots of regional CBF values with their standard deviations for individual pigs. Notice that normo- as well as hypercapnic data points are plotted in the same diagram to visualize overall agreement of absolute values as well as responses to $CO_2$ among PET and MRI. There was a tendency for normocapnic data points to be grouped in the lower left and hypercapnic data points in the upper right quadrant of the plots. Notice that the error bars associated with the MRI measurements appear smaller than the corresponding PET values for the same region The average standard deviation on regional flow estimates was on the average 30% smaller than the corresponding standard deviation for the same PET ROI. FIG. 3 shows the corresponding plot for repeated PET measurement of CBF with $^{15}O$ butanol. The results of the linear regression analysis are shown in Table 2. The slopes of the linear regression lines did not significantly differ among the pigs (by multiple pairwise t-tests). For most animals, the regression coefficient $r^2$ (the proportion of the variance accounted for by the regression) ranged between 0.7 and 0.8.

This was slightly lower than the value (i.e. 0.86) obtained by comparing CBF maps obtained in identical brain slices with PET. Hence, the additional inaccuracies introduced by comparing CBF determined by two different methods are therefore small compared with the variance associated with comparisons made within the same method.

TABLE 2

| Pig | a | b | $r^2$ |
|---|---|---|---|
| 1 | 0.82 ± 0.10 | 11 ± 5 | 0.79 |
| 2 | 1.00 ± 0.11 | −2 ± 6 | 0.81 |
| 3 | 0.99 ± 0.15 | 0 ± 10 | 0.70 |
| 4 | 0.97 ± 0.11 | −4 ± 6 | 0.79 |
| 5 | 0.98 ± 0.11 | 2 ± 7 | 0.81 |
| 6 | 0.90 ± 0.12 | 6 ± 5 | 0.75 |
| 6* | 0.77 ± 0.07 | 10 ± 3 | 0.86 |

Figure 4:
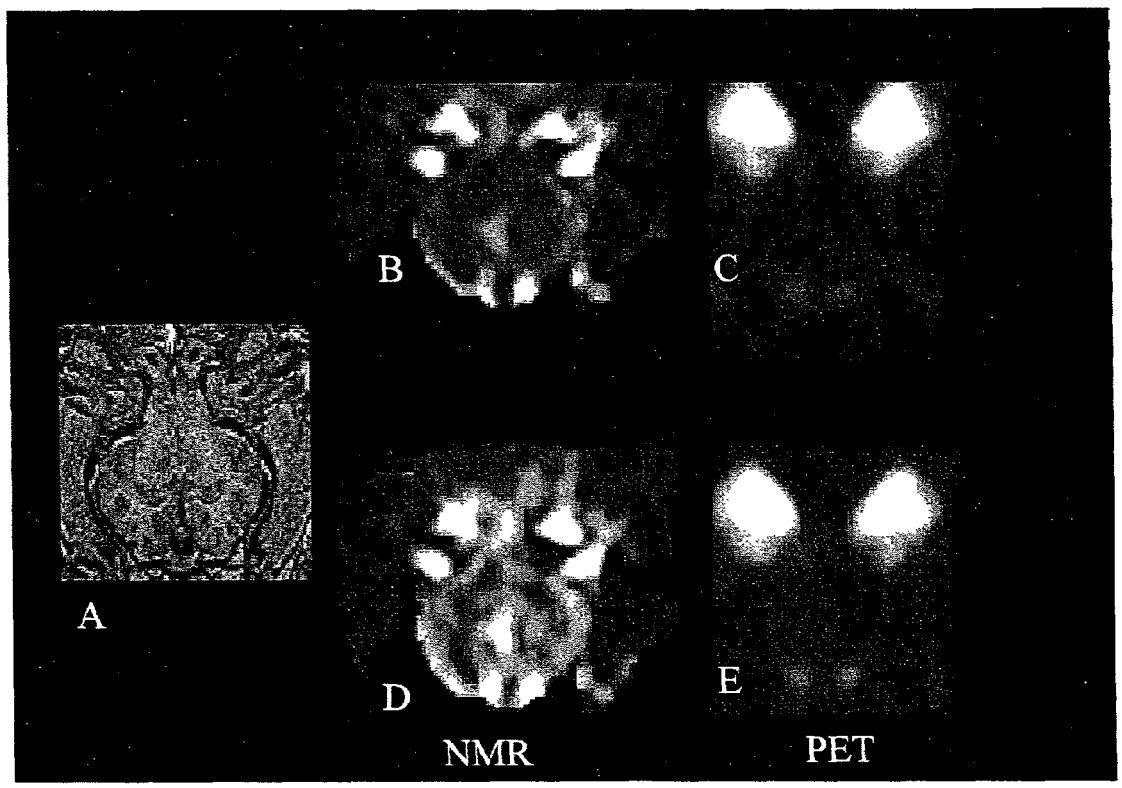
FIG. 4 shows CBV maps obtained with MR and PET, respectively.
Figure 5:
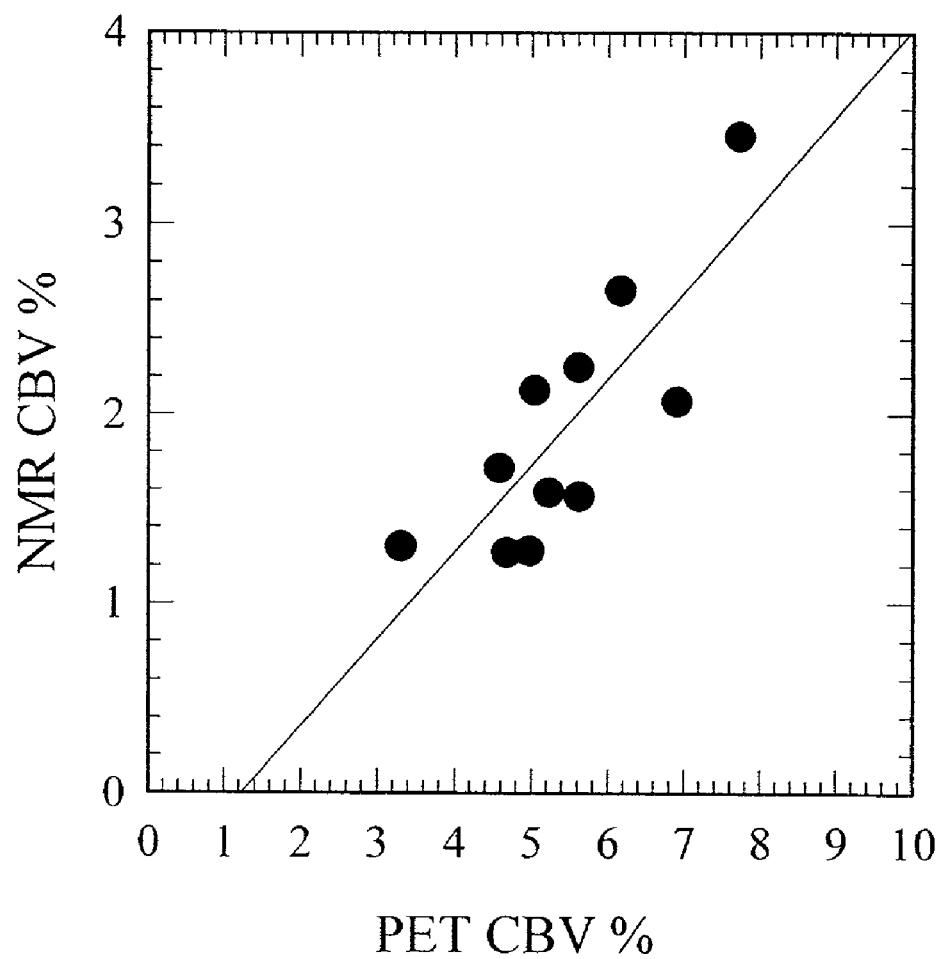
FIG. 5 plots average absolute MR versus PET values of CBV for corresponding slices under normo- and hypercapnia in 6 pigs.

FIG. 4 shows CBV maps obtained with MR and PET, respectively. As CBV and CBF are obtained in the same units, absolute CBV values were obtained by multiplying the integrated value by the normalisation factor $\Phi_{Gd}=1.09$ determined above. FIG. 5 plots average absolute MR versus PET values of CBV for corresponding slices under normo- and hypercapnia in 6 pigs. Care was taken to include brain parenchyma rather than large vessels in the image. Also shown is the linear regression line with slope 0.45±0.11 (SD) and y intercept −0.56±0.61 (SD). Notice the apparent linearity between vascular volume measurements with PET and MRI. As both MR and PET CBV values are now in absolute values, the plot shows that only 40% of the total vascular volume is detected by the spin echo EPI MR technique.

Discussion

In spite of the inherent complexity of susceptibility contrast mechanisms and its use for measurements of CBF, our rather simple approach to quantify CBF from MRI seems promising as a first approach towards measurement of absolute CBF. In five out of six animals, the common conversion factor yielded absolute CBF values in agreement with those obtained by PET. Furthermore, the MRI technique yielded CBF maps with good contrast between gray and white matter structures, just as by regional comparison, MRI CBF maps had less noise than the corresponding PET CBF maps, using similar spatial resolution. In the following, we will discuss how our assumptions and experimental approach may explain the poorer correlation between MRI and PET CBF results than among repeated PET CBF measurements.

First, assuming a common constant that relates injected MR contrast dose to the area under the image-based arterial input concentration time curve may not always hold true. The validity of this assumption is sensitive to the fraction of the injected contrast dose delivered to the brain circulation in the two experimental conditions, and more importantly, the linearity between contrast concentration and change in transverse relaxation rate assumed in equation 15. Secondly, we assumed a linear relationship between CBF and arterial $CO_2$ levels when correcting for different degrees of hypercapnia in PET and MRI experiments. Deviations from linearity may, however, cause systematic changes in the slope and intercept of the regression line, just as the $CO_2$ response of the animal may change after long-term anesthesia (MR measurements were performed approximately 4 hours after the PET measurements).

As for more methodological problems, comparing MRI with PET may have affected our regression results in several ways. Co-registration of MRI and PET data may not be completely accurate, just as MR images obtained with echo planar imaging can be somewhat distorted due to magnetic field inhomogeneities and susceptibility artifacts. The latter causes anatomical structures imaged by the EPI sequence not to be imaged in the exact location as in the 3D image sequence used for co-registration. In cases where we noticed slight in-plane differences in locations, we adjusted the location of the ROI in the MRI images to account for this fact.

A more complex problem was caused by the differences in inherent resolutions of PET and MRI. For our PET tomograph, the effective resolution with the parameters used is approximately 4.5 mm in the center of the investigated volume. By using a Gaussian filter, we sought to blur the MRI measurements to yield the same resolution as the PET CBF measurements. However, the CBF images in FIG. 1 still indicate that there may be differences in resolution that are not accounted for, causing influence from neighbouring regions to be different in the two imaging modalities, thereby causing a non-linear relationship between regional CBF values simply due to differences in resolution. We believe these factors explain the slightly better regression statistics obtained when comparing two PET CBF measurements rather than comparing MR.

Some data sets (pig 1 and 6) yielded regression lines with slopes somewhat below unity and a positive y-axis intercept, as also found when comparing $^{15}$O water and $^{15}$O butanol CBF measurements. With the latter tracer, the discrepancy is due to limited diffusibility of water across the blood-brain barrier, causing higher flows to be underestimated (Ohta et al., 1996). For MRI measurements, the earlier simulation studies also predicted that high flow rates would be underestimated, when the microvascular mean transit time is short relative to the characteristic time scales of the bolus input and the imaging rate underestimated (Østergaard et al., 1996). By very rapid bolus administration and imaging once per second, we hoped to minimise this effect. The results indicate that the MR technique may perform slightly worse than the PET method with $^{15}$O water in terms of measuring very high flow rates.

The measurements provide insight into the selectivity for the effect of small vessels of the $T_2$-weighted spin echo EPI sequence used in our experiment. By a Monte Carlo simulation approach, Weisskoff et al. (1994) previously demonstrated that the susceptibility contrast in this imaging sequence arises mainly in small, capillary size vessels. As the distribution of fractional vascular volume as a function of vascular diameter is not fully known, it is difficult to predict absolute volume values based on these simulations. Our 40–50% estimate of the vascular fraction detected by MR is therefore difficult to compare to theoretical predictions. However, studies of peripheral tissue indicate that vessels smaller than 3040 μm diameter (small arteries, arterioles, capillaries, venules and small veins) represent roughly 50% of the total vascular volume (Johnson, 1973). Assuming that the MR measurements are predominantly sensitive to the smallest vessels, our value of 40–50% therefore points towards a sensitivity to vessels smaller than 30–40 μm. of the MR technique. This in turn makes the CBF and CBV techniques sensitive to microvascular phenomenons, e.g. neovascularization in neoplasia (Aronen et al., 1994) and flow-volume mismatches in stroke due to delayed passage through oxygen exchanging vessels (Heiss et al. 1994).

EXAMPLE 2

Cerebral Blood Flow Measurements by MRI Bolus Tracking: Comparison with [$^{15}$O]H$_2$O Pet in Humans

SUMMARY OF THE EXAMPLE

In six young, healthy volunteers, a novel method to determine cerebral blood flow (CBF) using magnetic resonance (MR) bolus tracking was compared with H$_2$$^{15}$O positron emission tomography (PET). The method yielded parametric CBF images with tissue contrast in good agreement with parametric PET CBF images. Introducing a common conversion factor, MR CBF values could be converted into absolute flow rates, allowing comparison of CBF values among normal subjects.

Background

Recent results indicate that it may be possible to measure cerebral blood flow (CBF) by dynamic magnetic resonance imaging (MRI) of paramagnetic contrast agent bolus passage (Østergaard et al., 1996a). Due to the complexity of suceptibility contrast, this technique initially only allowed determination of relative flow rates. In a preliminary study in six normal volunteers, the mean gray:white flow ratio was found to be in good agreement with PET literature values for age matched subjects (Østergaard et al., 1996b). In a recent animal hypercapnia study (Østergaard et al., 1997), an approach was introduced to allow absolute quantitation by introduction of an empirical normalisation constant.

In this study we compare absolute regional NMR bolus CBF values with CBF values determined by [$^{15}$O] water uptake, detected by positron emission tomography (PET) in normal human volunteers.

Theory

MRI CBF Measurements

Estimation of cerebral blood flow from measurement of non-diffusable tracers is discussed in detail by Østergaard et al. (1996a). In brief, the concentration $C_t(t)$ of intravascular contrast agent within a given tissue element can be written $$C_t(t) = f_1 \cdot C_a(t) R(t) \qquad \text{Eq. 16}$$

where $F_t$ is tissue flow and denotes the convolution of $R(t)$, the vascular residue function (normalised impulse response function) with the arterial input function, $C_a(t)$.

It has been demonstrated that, using singular value decomposition (SVD), $R(t)$ and CBF can be determined with good accuracy, independent of the underlying vascular structure and volume (Østergaard et al., 1996a).

PET CBF Measurement

The regional uptake of water is described by the model of Ohta (Ohta et al. 1996):

$$C_{br}(t) = (1 - V_p) \cdot K_1 \cdot \int_0^t C_a(\tau) e^{-k_2(t-\tau)} d\tau + V_p \cdot C_a(t) \qquad \text{Eq. 17}$$

where we assume $K_1$=CBF for water, and $$k_2 = \frac{K_1}{V_d},$$

where $V_d$ is the distribution volume of the tracer. $V_p$ is the instantaneous vascular distribution volume of the tissue.

Material and Methods

Volunteers and Experimental Protocol

Six young, healthy volunteers (3 male, 3 female, mean age 26±6 years) were examined. Two additional volunteers were included in the study. One was excluded due to head motion during MRI measurements, while the other was excluded due to a significant change (>5%) in $P_aCO_2$ in between PET and MR scans. PET and MR scans were performed on the same day, within 2 hours of each other. Prior to the examination, arterial and venous catheters were inserted in the left radial artery and right antecubital vein, respectively. Arterial blood samples were withdrawn and analysed (ABL 300, Radiometer, Copenhagen) at regular intervals to monitor blood gases and whole blood acid-base parameters (pH, $pCO_2$, $pO_2$, $HCO_3$ and $O_2$ saturation). Prior to each CBF measurement, the volunteer was allowed to rest at least 30 minutes with closed eyes. The project was approved by the Regional Danish Committee for Ethics in Medical Research, and performed after informed, written consent from each volunteer.

PET Imaging Protocol.

The volunteers were studied in a Siemens ECAT EXACT HR PET camera using a custom-made head-holding device. To measure CBF, a fast i.v. bolus injection of 500 MBq $H_2^{15}O$ in 5 ml saline was performed, followed immediately by an i.v. injection of 10 ml of isotonic saline to flush the catheter. A sequence of nineteen (12, 6 and 3 samples during the first, second and third minute, respectively) arterial blood samples (1–2 ml) and 12 PET brain images (6, 4 and 2 images per minute, respectively) were then obtained. Brain image data were reconstructed using scatter correction, and a Hann filter with a cutoff frequency of 0.5 pixel$^{-1}$, resulting in an isotropic spatial resolution (FWHM) of 4.6 mm. Correction for tissue attenuation was based on a $^{68}Ga$ transmission scan. Radioactivity levels in image and arterial blood were corrected for the half-life of $^{15}O$ (123 s).

Pet Radiochemistry $^{15}O_2$ was produced by the $^{14}N(d,n)^{15}O$ nuclear reaction by the bombardment of nitrogen gas with 8.4 MeV deuterons using a GE PETtrace 200 cyclotron. $^{15}O_2$ was mixed with hydrogen and passed in a stream of nitrogen gas over a palladium catalyst at 150° C. to produce $^{15}O$-water vapour, which was trapped in 10 ml sterile saline.

MRI Imaging Protocol

MR imaging was performed using a GE Signa 1.0 Tesla imager (GE Medical Systems, Milwaukee, Wis.). Following a sagittal scout, a $T_1$ weighted 3D image was acquired for co-registration of MR and PET data. For dynamic imaging of the bolus passages, spin echo (SE) echo planar imaging (EPI) was performed (Repetition time TR=1000 ms, echo time TE=75 ms), using a 64 by 64 acquisition matrix was used with a 18 by 18 cm transverse FOV, leading to an in-plane resolution of 3 by 3 mm. The slice thickness was 6 mm. In all experiments, bolus injection of 0.2 mmol/kg Gadodiamide (OMNISCAN®, Nycomed Imaging, Oslo, Norway) was performed at a rate of 5 ml/sec. A pre-dose of 0.05 mmol/kg was given to reduce systematic effects from changes in blood $T_1$.

MR Image Analysis

To determine tissue and arterial tracer levels C(t), we used susceptibility contrast (Villringer et al., 1988) arising from compartmentalisation of the paramagnetic contrast agent. We assumed a linear relationship (Weisskoff et al., 1994) between paramagnetic contrast agent concentration and the change in transverse relaxation rate $\Delta R_2$:

$$C(t) \propto \Delta R_2(t) = -\log\left(\frac{S(t)}{S(0)}\right)/TE \qquad \text{Eq. 18}$$

where S(O) and S(t) are the signal intensities at the baseline and at time t, respectively, and TE the echo time. The arterial concentration was determined from pixels around the middle cerebral artery in the imaging plane (Porkka et al., 1991). The integrated area of the arterial input curve was in each measurement normalised to the injected contrast dose (in mmol per kg body weight) according to our earlier approach (Østergaard et al., 1997). Deconvolution was performed following the application of a 3×3 uniform smoothing kernel to the raw image data, and the maximum point on the deconvolved impulse response curve was chosen to be CBF.

PET Image Analysis

The 3D PET CBF images were used to automatically co-registered with the 3D MR images (Collins et al., 1994). Raw PET image data were then transformed and re-sampled to the same spatial location and resolution as the MR CBF data to allow direct comparison of the two techniques. Following the application of a 3×3 uniform smoothing kernel to our raw PET image data, these were fitted to equation 2 using non-linear, least squared regression analysis on a pixel-by-pixel basis.

Comparison of PET and MR Parametric Images

Pixel by pixel maps of CBF (at similar anatomical locations, pixel size and resolution) generated by PET and MR, respectively, were then compared on a regional basis. In each image, 20–25 regions of similar size were chosen, including gray and white matter. The means of all regional values were then averaged, to yield a common conversion factor between MRI flow units and absolute flow in ml/100 ml/min). Regional average CBF values and their standard deviations (derived from the population of pixels within the ROI) were then compared.

Results

Table 3 shows values of $P_aCO_2$ and $P_aO_2$ for all volunteers during MR and PET measurements. Volunteer 3 showed a 13% change in $P_aCO_2$ and was excluded from the analysis, while volunteer 1 had to be excluded due to head motion during the MR measurements.

TABLE 3

| Subject | $P_aCO_2$ (kPa) | | | $P_aO_2$ (kPa) | | |
|---|---|---|---|---|---|---|
| no | PET | MR | % change | PET | MR | % change |
| 1 | 5.97 | 5.63 | −5.7 | 12.11 | 13.45 | 4.8 |
| 2 | 5.49 | 5.35 | −2.5 | 15.815 | 16.395 | 3.7 |
| 3 | 6.63 | 5.79 | −12.7 | 12.05 | 12.625 | 4.8 |
| 4 | 5.31 | 5.33 | 0.4 | 15.58 | 16.165 | 3.8 |
| 5 | 5.25 | 5.325 | 1.4 | 17.175 | 15.265 | −11 |
| 6 | 4.92 | 4.93 | 0.2 | 15.165 | 14.67 | −3 |
| 7 | 4.485 | 4.675 | 4.2 | 15.925 | 16.97 | 6.6 |
| 8 | 4.965 | 4.965 | 0 | 16.16 | 15.205 | −5.9 |

By averaging all regional flow rates, a common conversion factor, $\Phi_{Gd}$=0.87 was found. In the following, all MR flow rates were multiplied by this constant.

Figure 6:
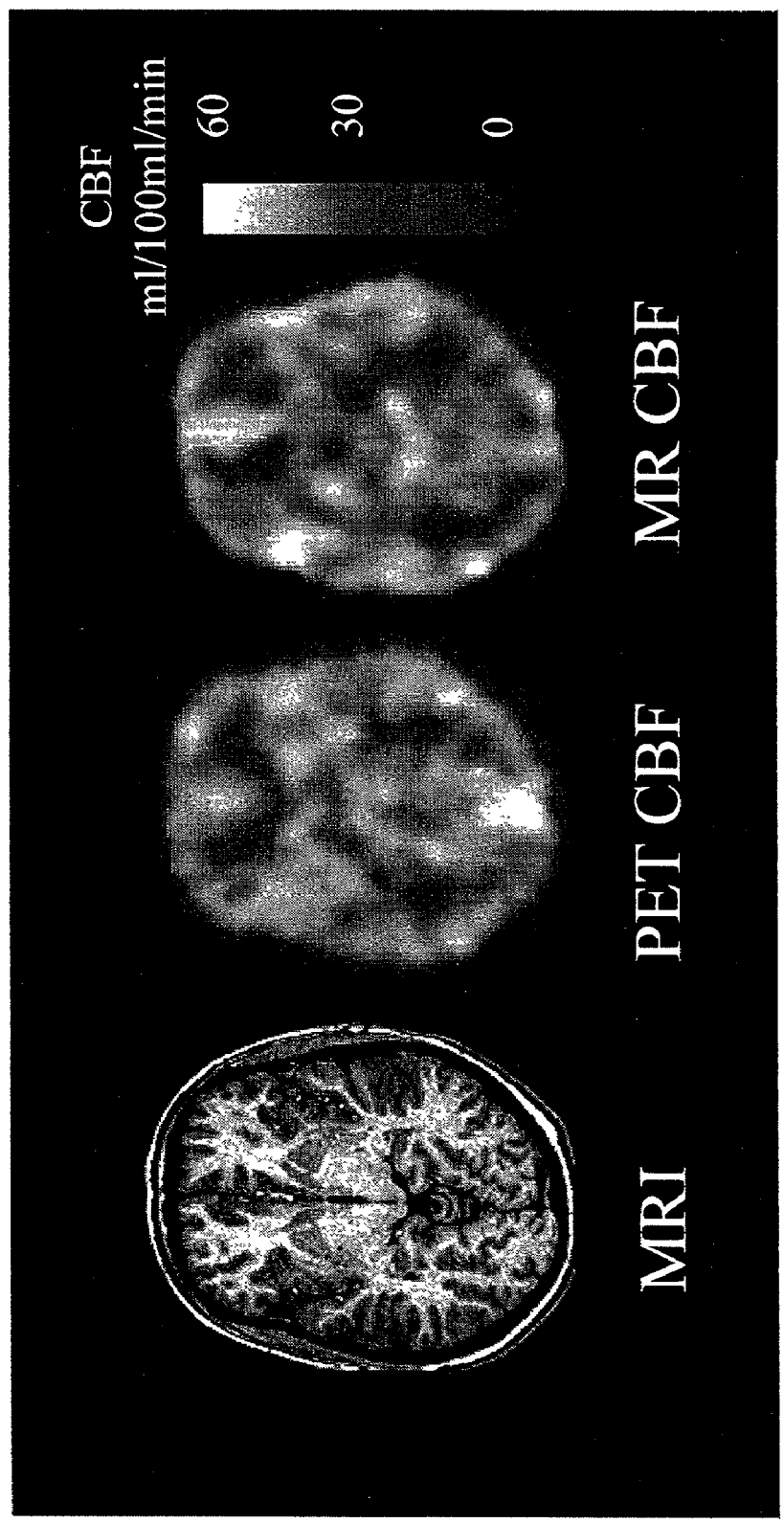
FIG. 6 shows parametric CBF maps determined by PET and NMR, respectively.
Figure 7:
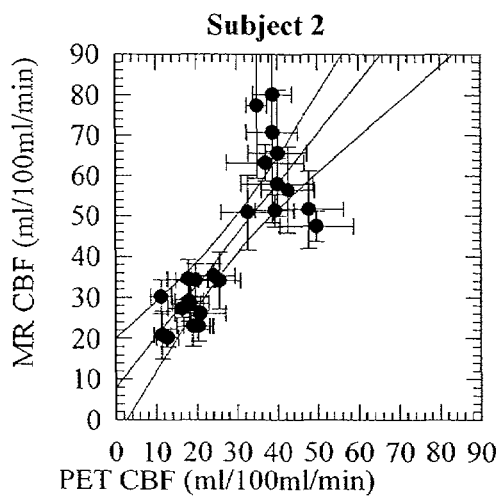
FIG. 7 shows MR versus PET plots of regional CBF values along with their standard deviations for the six volunteers.
Figure 7:
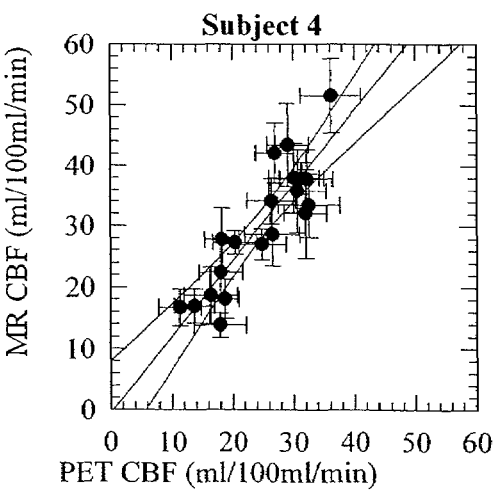
Figure 7:
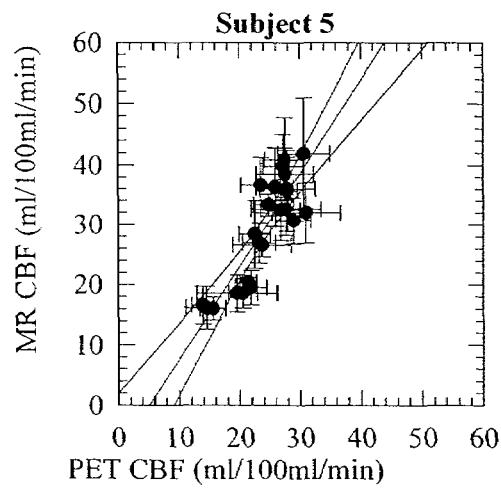
Figure 7:
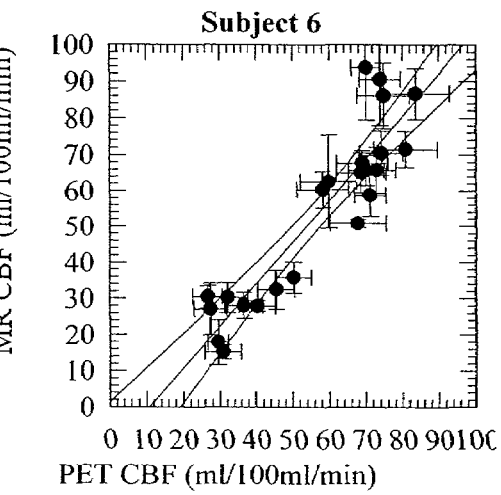
Figure 7:
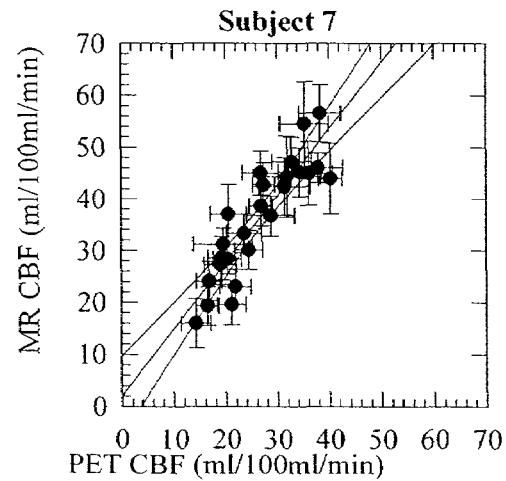
Figure 7:
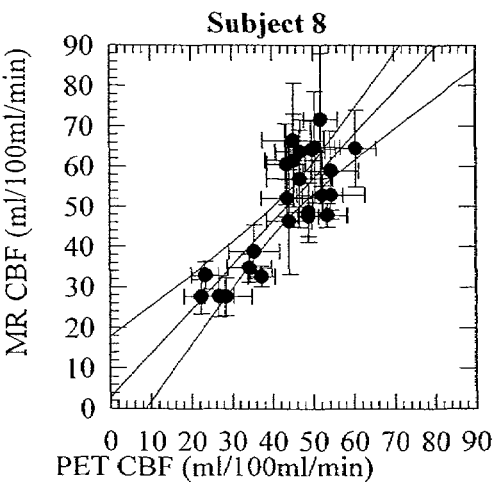
Figure 8:
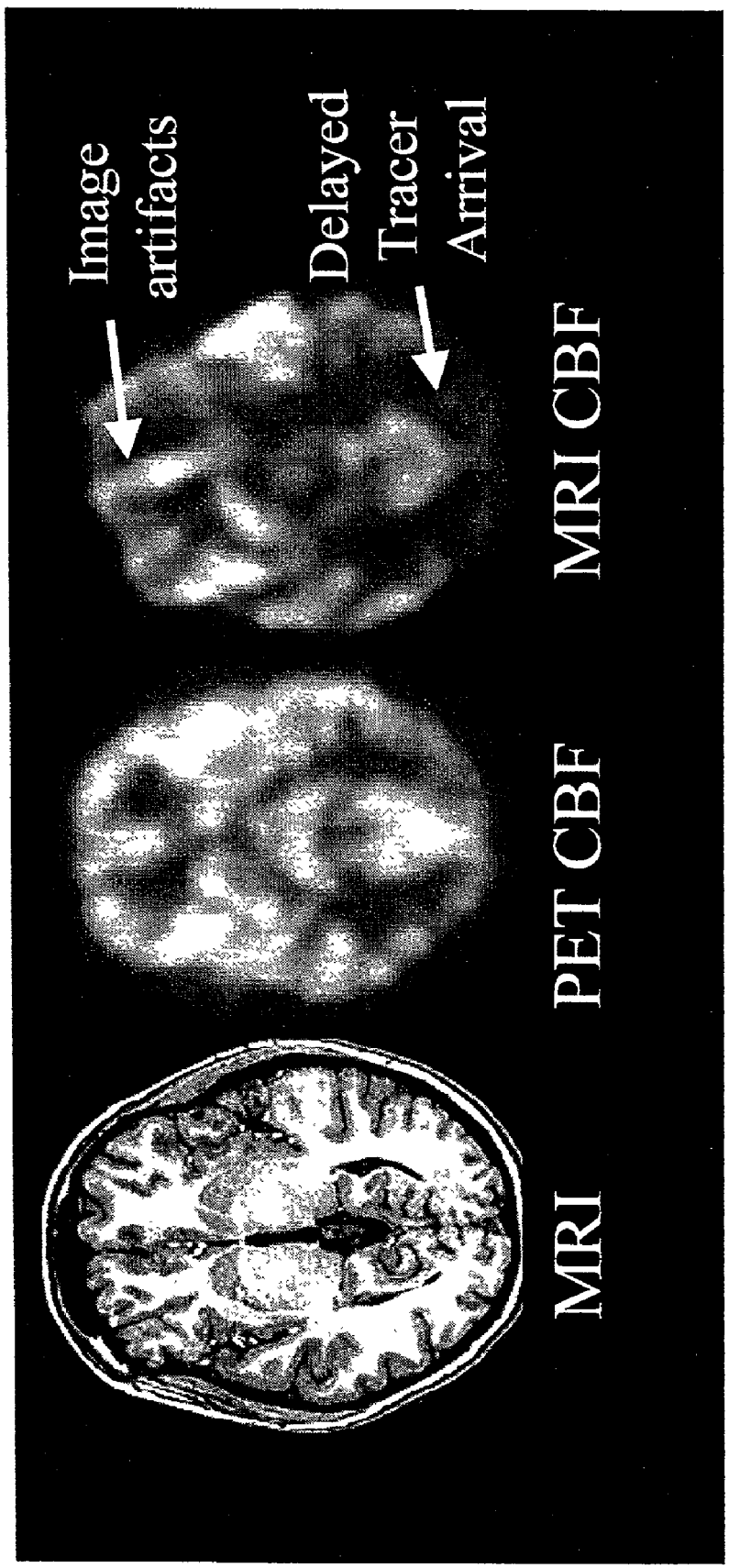
FIG. 8 shows the conventional MRI as well as the PET CBF maps from the volunteer 6 and what may reflect a methodological problem of the MR technique.

FIG. 6 shows parametric CBF maps determined by PET and NMR, respectively. To facilitate visual comparison, the MR flow image was blurred to the resolution of the PET image. Also shown is the corresponding anatomical MR image. It is noticed that vessels appear to be treated somewhat differently by the two methods: In the PET images, these appear as high flow areas, whereas in the MR images, arterial branches appear as high flow regions. FIG. 6 shows MR versus PET plots of regional CBF values along with their standard deviations for the six volunteers. Also shown are linear regression lines and their 95% confidence regions. White matter ROIs are represented in the lower left quadrant of the plots, whereas gray matter ROIs are in the upper right. There was no systematic deviation from the regression lines for gray and white matter flow rates, in agreement with the qualitative appearance of the flow maps in FIG. 6. Also, notice that error bars are of comparable size for PET and MR for identical size ROIs. Table 4 shows the regression results. The portion of the variance accounted for by the regression ($r^2$), was generally between 65 and 83 percent (see Table 4). To test whether the differences in regression slopes could be ascribed to individual uncertainties, the F statistic was calculated, showing no significant differences. Still, it was noticed that subject 5 had a somewhat larger slope than the remaining volunteers. In one volunteer (subject 8), we found an apparent hypoperfusion in the occipital lobe not visible in the PET CBF image (FIG. 8). We will discuss the implications of this below.

TABLE 4

| Subject | Slope ($m_i \pm s_i$) | Intercept | $r^2$ |
|---|---|---|---|
| 2 | 1.09 ± 0.17 | 6.88 ± 5.17 | 0.65 |
| 4 | 1.08 ± 0.14 | −0.48 ± 3.58 | 0.77 |
| 5 | 1.34 ± 0.17 | −6.84 ± 4.21 | 0.74 |
| 6 | 1.01 ± 0.10 | −10.86 ± 5.92 | 0.83 |
| 7 | 1.12 ± 0.12 | 1.73 ± 3.29 | 0.79 |
| 8 | 0.94 ± 0.14 | 2.41 ± 6.42 | 0.66 |
| Mean | 1.10 ± 0.14 | −1.19 ± 6.51 | 0.74 |

Discussion

There was generally good agreement between regional PET and MR CBF values. The fact that the ratio of gray and white matter flow rates appears identical using MR and PET confirms the earlier finding that relative CBF values can be determined within the same subject (Østergaard et al., 1996b). Furthermore, the data supports that our earlier normalisation routine (Østergaard et al., 1997) allows determination of absolute flow rates and hence comparison among subjects. The conversion factor found (0.84) was somewhat lower than that previously found for pigs (1.09) (Østergaard et al., 1997). We ascribe this to anatomical differences, especially the fact that the portion of the cardiac output distributed to the brain is probably smaller in pigs than in humans.

The variance observed relative to a simple linear relationship between the two different CBF estimates can be ascribed to several factors. First, CBF measurements were performed about 2 hours apart, and even though the arterial $CO_2$ levels were nearly identical, changes in the overall level of consciousness may have resulted in different flow rates. Also, as regional flow is unlikely to be constant over even very short time scales, the fact that the MR CBF measurements are acquired in only 15 seconds, whereas radiolabeled water levels are observed for three minutes by PET, may contribute to differences in regional values. More technical and methodological issues may have affected our measurements, as well. First, the rapid EPI sequence used in our measurements is sensitive to magnetic field inhomogeneities. This may result in misregistration of corresponding PET and MRI regions. This is illustrated in FIG. 8, displaying the conventional MRI as well as the PET CBF maps from the volunteer 6. FIG. 8 also shows what may reflect a methodological problem of the MR technique. The MR technique is sensitive to large delays in tracer arrival, causing CBF to be somewhat underestimated. In this volunteer, the tracer arrival in the posterior circulation was delayed by several seconds relative to the remaining brain. This, apart from possible differences in visual activity during the two measurements, may explain the occipital hypoperfusion in this volunteer. Finally, the assumption that the area under the arterial concentration time curve is proportional to the injected dose in all subjects may not hold true under all circumstances. Also, circulatory disturbances may cause the characteristic time scale of the arterial input to become longer than that of the vascular transit time, making CBF measurements difficult (Kent et al 1997). This underlines the importance of performing very rapid bolus inputs, and validating this approach in patient populations, especially those with either circulatory disturbances or delayed tracer arrival in the brain (see above), e.g. major artery occlusion.

There were some qualitative differences among the CBF images obtained by the two modalities. The MR technique was found to interpret small arteries as high flow regions. This is inherent to the technique, as it does not mathematically distinguish between large vessel and capillary tracer dispersion. However, as CBV is simultaneously determined by integration of the tissue concentration time curve (Rosen et al. 1991), this does not pose a problem in interpreting the CBF maps. Also, due to the inherent sensitivity of susceptibility contrast imaging to small vessels (Fisel et at. 1991, Weisskoff et al. 1994) large vessels are not seen in the images. In contrast, PET CBF images partly interpret dispersed venous blood as tissue flow, whereas arteries are suppressed by means of the $V_0$ term in equation 17.

Figure 9:
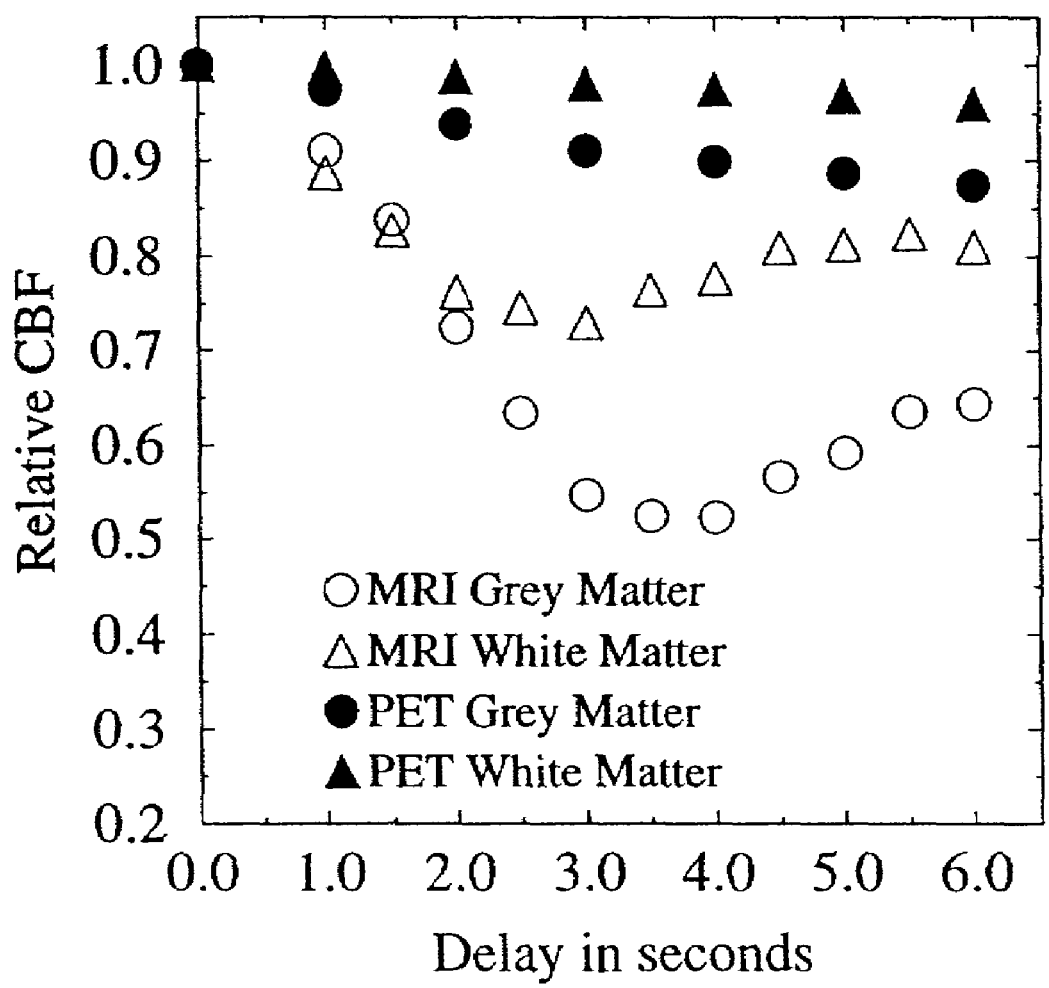
FIG. 9 shows how flow estimates become increasingly underestimated as the arrival delay of the tracer at a brain region increases, in both PET and MR CBF measurements.

In one volunteer (subject 8), we found a marked hypoperfusion in the occipital lobe possibly due to delay in the arrival of tracer in the posterior circulation. This effect was predicted in theoretical simulations of the technique (Østergaard et al. 1996a). FIG. 9 shows how flow estimates become increasingly underestimated as the arrival delay of the tracer at a brain region increases, in both PET and MR CBF measurements (Simulations were performed by simply introducing delays between the arterial and cerebral concentration time curves in volunteer 6). Notice, however, that whereas PET measurements may underestimate flow by 15%, underestimation by MRI can be as much as 50%. Even though we only noticed this effect in one volunteer, these simulations underline the importance of further evaluating this technique in patient populations with e.g. vascular diseases. Also, we are currently working on approaches to minimise the sensitivity of our CBF algorithm to tracer arrival delays.

We used rather low spatial resolution (64 by 64 matrix), single slice measurements. It is worth noticing that most current MR systems with EPI capabilities allows multi-slice acquisitions at a considerably higher spatial resolution (typically 2.5 by 2.5 mm pixels). This allows CBF measurements at twice the spatial resolution of most current PET systems.

Conclusion

The study indicates that relative as well as absolute CBF values can be determined using MRI bolus tracking in humans. Although further theoretical and experimental validation is needed in patients, the technique provides easy, rapid CBF measurement without invasive arterial measurements or radioactive exposure, at high spatial resolution.

EXAMPLE 3

Modeling Cerebral Blood Flow and Flow Heterogeneity from Magnetic Resonance Residue Data Summary of the Example Existing model-free approaches to determine cerebral blood flow by external residue detection show a marked dependence of flow estimates on tracer arrival delays and dispersion. In theory, this dependence can be circumvented by applying a specific model of vascular transport and tissue flow heterogeneity. A method is presented to determine flow heterogeneity by MR residue detection of a plasma marker. Probability density functions of relative flows measured in 6 healthy volunteers were similar among tissue types and volunteers, and were in qualitative agreement with literature measurements of capillary red blood cell and plasma velocities. Combining the measured flow distribution with a model of vascular transport yielded excellent model fits to experimental residue data. Fitted gray:white flow rate ratios were in good agreement with PET literature values, as well as a model-free singular value decomposition (SVD) method in the same subjects. The vascular model was found somewhat sensitive to data noise, but showed far less dependence upon vascular delay and dispersion than the model-free SVD approach.

Background

A technique to determine cerebral blood flow (CBF) by magnetic resonance (MR) bolus tracking of an intravascular contrast bolus has recently been presented (Østergaard 1996a). By performing non-parametric singular value decomposition (SVD) deconvolution of tissue time concentration curves by a non-invasively determined arterial input function, the algorithm (hereafter referred to as the SVD method) generates pixel-by-pixel maps of CBF (Østergaard 1996a). The SVD method has been demonstrated to yield CBF values in excellent agreement with PET in normal volunteers (Example 2 (Østergaard 1998a)), as well as in an animal hypercapnia model (Example 1 (Østergaard 1998b)). Although the model-free SVD method offers the advantage of being independent of the underlying vascular structure, the method is somewhat susceptible to dispersion and delay of the measured AIF before it reaches the imaging pixel (Østergaard 1996b). Especially in the setting of major vessel disease, dispersion in the feeding vessel may be significant relative to tissue tracer retention, causing underestimation of CBF, and therefore overestimation of the CBV:CBF ratio (Østergaard 1996b). This ratio, the plasma mean transit time (MTT), is an important parameter in evaluating cerebrovascular perfusion reserve, and therefore the inability of the SVD approach to distinguish vascular dispersion from prolonged tissue MTT may ultimately impair its clinical use.

Bassingthwaighte and co-workers have developed modelling tools to describe major vessel transport as well as microvascular tracer retention (King 1993; King 1996) A derived model of the coronary circulation has been successfully applied to MR data, allowing non-invasive measurements of coronary blood flow (Kroll 1996). This model (hereafter referred to as the vascular model), modified for the cerebral circulation, may ultimately provide estimates of CBF and MTT independent of major vessel delay and dispersion. The aim of this study was to extend this vascular model to the cerebral circulation. First, a first-order expression of flow heterogenity in the cerebral circulation was derived by a model-free analysis of tracer retention in areas of negligible major vessel dispersion. To validate the model, the vascular model was fitted with measured flow heterogeneity, to human MR residue measurements, and compare the resulting flow rates to literature values, as well as the SVD method. Finally, the sensitivity of the vascular model to tracer delays was compared in simulated data.

Theory

Vascular Model

Figure 10:
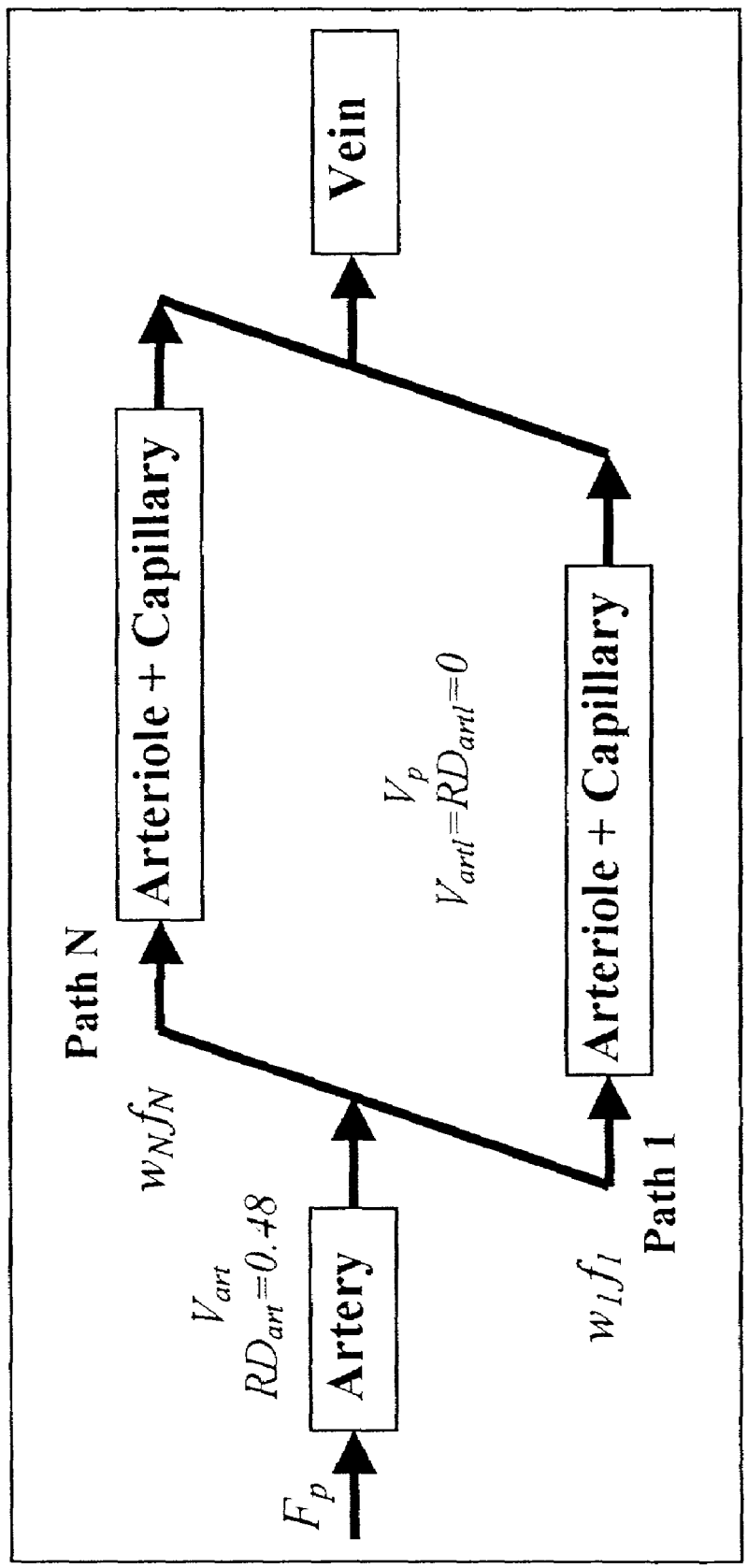
FIG. 10 shows that the vasculature was modeled a major, feeding artery in series with 20 small vessels in parallel.

A modified version of the vascular model previously described by Kroll et al (Kroll 1996) was used. The vasculature was modelled a major, feeding artery in series with 20 small vessels in parallel—See FIG. 10. In the vascular model the flow is directed along the parallel pathways, with $w_i$ representing the fraction of flows with values $f_i \cdot Fp$, where $F_p$ is total flow. The feeding artery was described by a fixed, relative dispersion in transit times (RD=0.48) and a delay, determined by its volume fraction, $V_{art}$ (King 1993). The capillaries were modelled as simple delay lines of fixed length (100 μm), with volume $V_p$. In the following, the tissue flow $F_p$, the feeding vascular volume $V_{art}$, and capillary volume $V_p$ was allowed to vary. The observed signal changes due to magnetic susceptibility contrast agent arises—when using a spin echo sequence (See Materials and Methods below)—mainly from capillaries (Fisel 1991; Boxerman 1995; Weisskoff 1994). In the model, total tissue tracer concentrations were therefore calculated based on the amount of tracer in the small, parallel vessels. The distribution of transit times in the capillary bed was incorporated by an algorithm assigning appropriate flows and weights to the parallel vascular paths, to achieve a given heterogeneity (King 1996). This flow heterogeneity is described by a probability density function (PDF), assigning a probability w(f) to a given relative flow f, i.e. flow relative to the mean flow, $F_p$. In the following, it is described how an estimate of flow heterogeneity in humans is obtained from MR residue data. For a more detailed discussion of modelling flow heterogenity, see King et al. (King 1996).

Flow Heterogeneity from Residue Data

The fact that the impulse response to a plasma tracer can be estimated by nonparametric deconvolution of the tissue residue during the tracer passage by a non-invasively determined arterial input function (AIF) is utilised. From this the distribution of plasma transit times, and—under certain assumptions regarding the distribution of capillary lengths—the distribution of flows in the region are derived.

The tissue concentration $C_t(t)$ of tracer in response to an arterial input function $C_a(t)$ is given in Equation 4. The formula is equivalent to the integral $$C_t(t) = F_t \cdot C_a(t) \otimes R(t) \equiv F_t \cdot \int_0^t C_a(\tau) R(t-\tau) d\tau \qquad \text{Eq. 19}$$

where $F_t$ is tissue flow and R is the residue function, i.e. the fraction of tracer present in the vasculature at time t after a perfect, infinitely sharp input in the feeding vessel. Assuming the arterial and cerebral concentrations are measured at equally spaced time-points $t_1, t_2, \ldots, t_N$, this equation can be discretized, assuming that over short time intervals Δt, the residue function and arterial input values are constant in time:

$$C_t(t_j) = F_t \cdot \int_0^{t_j} C_a(\tau) R(t-\tau) d\tau \approx \Delta t \cdot F_t \cdot \sum_{i=0}^{j} C_a(t_i) R(t_j - t_i) \quad \text{Eq. 20}$$

which is equal to the expression in Equation 6.

As previously described (Østergaard 1996b), this equation can be modified to residue and arterial input functions that vary linearly in time. The SVD approach provides a powerful numerical tool to solve Equation 6 in the presence of experimental noise to yield the residue function. The distribution of transit times, h(t), is then found from $$R(t) \equiv \left[1 - \int_0^t h(\tau) d\tau \right] \Rightarrow h(t) = -\frac{dR}{dt} \quad \text{Eq. 21}$$

i.e. the slope of the residue function. At a given time point $t_1$, h(t) can be estimated as $$h(t_i) = \frac{1}{2} \cdot \left( \frac{R(t_{i+1}) - R(t_{i-1})}{\Delta t} \right) \quad \text{Eq. 22}$$

The probability density function (PDF) of transit times (t) is turned into a distribution of relative flow rates f, w(f), by requiring $$w(f) df = h(t) dt \quad \text{Eq. 23}$$

and that the central volume theorem (Stewart 1894) is obeyed (Equation 7). Assuming all vascular paths have equal volume, the distribution of flow rates is obtained from Equation 8, and normalised to have unit mean flow and area (Equation 9).

Materials and Methods

Volunteer Data

Six normal volunteers (Age 29±4 yrs) were examined according to a standard perfusion protocol on a GE Signa 1.5 T imager (General Electric, Waukesha, Wis.) retrofitted for EPI capabilities (Instascan, Advanced NMR Systems, Wilmington, Mass.), using spin echo (SE), echo planar imaging (EPI) with a time of repetition (TR) of 1.0 seconds, and a time of echo (TE) of 100 ms. The slice thickness was 5 mm with an in-plane resolution of 1.6 mm by 1.6 mm in a 40 by 20 cm field-of-view (FOV). A total of 52 images were acquired, starting 15 seconds before i.v. injection of 0.3 mmol/kg contrast medium (Dysprosium-diamide, Nycomed Imaging, Oslo, Norway). Intravascular contrast agent concentrations, C(t), were estimated assuming a linear relationship between concentration and change in transverse relaxation rate, $\Delta R_2$ (Villringer 1988; Weisskoff 1994) (Equation 1).

Feeding arterial branches were identified in the image slice as pixels displaying early concentration increase after contrast injection (Porkka 1991). This approach does not determine absolute arterial tracer levels, but provides the shape of the AIF. To standardise the analysis below, the arterial input function was therefore scaled to yield a mean CBV of 3% (Example 1 (Østergaard 1998b)). In volunteers, a single arterial input function in the imaging plane was used for all tissue regions.

Determination of Flow Heterogeneity

Tissue concentration time curves were formed using Equation 1. Three gray and two white matter tissue regions consisting of 4 image pixels (0.05 cc) were then chosen, based on cerebral blood volume maps (Rosen 1990). The tissue residue function was calculated by SVD deconvolution of the tissue concentration time curve with the AIF. The resulting residue function was then converted into a probability density function (PDF) of relative flows as described in the Theory section above Model Analysis The experimentally determined flow heterogeneity PDF was then entered into the vascular model described above. For sixteen gray and white matter regions (0.25–0.4 cc), $F_p$, $V_p$, and $V_{art}$ were adjusted to obtain optimal fits to the corresponding tissue concentration time curves by nonlinear regression analysis (Chan 1993). The initial conditions were $F_p$=40 ml/100 ml/min, $V_p$=2%, and $V_{art}$=0.1%. The remaining model parameters are given in FIG. 10.

Comparison with Model-Free Approach

To compare the flow rates obtained with the vascular model with those of the model-free SVD approach (Østergaard et al., 1996a), the height of the deconvolved tissue response curve ($F_t \cdot R(t_i)$ in Equation 3), was determined for the same regions as used in the model analysis above. After determining mean white matter flow rate, 9 relative gray:white flow ratios were calculated for each volunteer, and compared with those obtained by the vascular model.

Sensitivity to Tracer Delays

In volunteer 4, each pixel tissue concentration time curve was delayed in steps of 0.25 second by linear interpolation to simulate the effects of tracer arrival delays. The simulated image data were then analysed as described above, and fitted flow rates by the SVD and vascular model approach plotted as a function of delay for comparison.

Sensitivity to Noise and Initial Conditions

To determine the overall sensitivity of parameter estimates with the vascular model to experimental noise, a set of synthetic data sets were generated using the vascular model itself, and two sets of typical values for flow, volume, and feeding artery volume ($F_p$=20 ml/100 ml/min, $V_p$=2%, $V_{art}$=0.5%, and $F_p$=50 ml/100 ml/min, $V_p$=3%, $V_{art}$=0.5%). These were converted into a MR signal intensity time curve using Equation 1, to generate a typical signal loss (25% for gray matter, equivalent to the higher flow) during a bolus passage. Random gaussian noise was then added, and 'noisy' concentration time curves ere again calculated from Equation 1. Simulated SNRs varied from 400 down to 12, the latter being typical for raw, pixel-by-pixel data obtained with perfusion protocols on a clinical MR system. The synthetic curves were analysed using the vascular model, using two different sets of initial conditions. These were chosen to represent two extremes of physiological values: $F_p$=80 ml/100 ml/min, $V_p$=6%, $V_{art}$=1%, and $F_p$=20 ml/100 ml/min, $V_p$=2%, $V_{art}$=0.1%. For each SNR, 24 simulations were performed, and the mean and standard deviations of the fitted model parameters were calculated for further evaluation. The dependency on initial conditions was evaluated by recording the number of simulations where two different initial conditions caused resulting fitted parameters to differ by more than 10% from their mean. To compare stability of the vascular model and SVD method to experimental noise, flow rates were determined from the same synthetic curves by the SVD method.

Results

Figure 11:
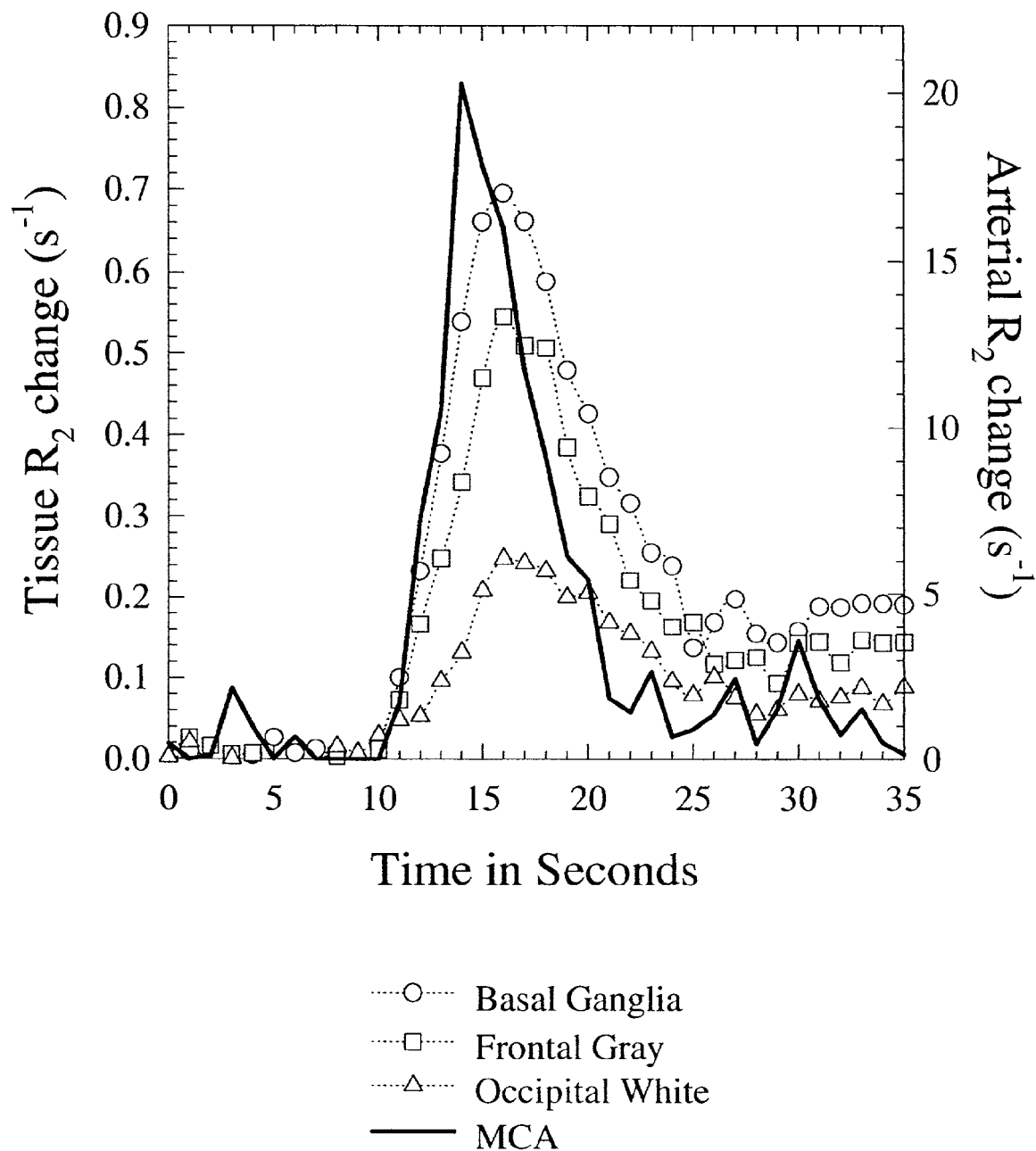
FIG. 11 shows a set of typical tissue and arterial concentration time curves obtained from volunteer 1.

FIG. 11 shows a set of typical tissue and arterial concentration time curves obtained from volunteer 1. The tissue ROIs consisted of 25–35 pixels (corresponding to 0.3–0.4 cc volumes). The average signal to noise ratio (SNR) (defined as the maximum tissue $R_2$ increase during bolus passage divided by the standard deviation of the noise relative to pre-bolus baseline image intensity) for the tissue volumes used for model validation (0.25–0.4 cc) was 30. The SNR of gray matter was a factor of 2 to 3 higher than that of white matter, due to the higher blood volume.

Flow Heterogeneity

Figure 12:
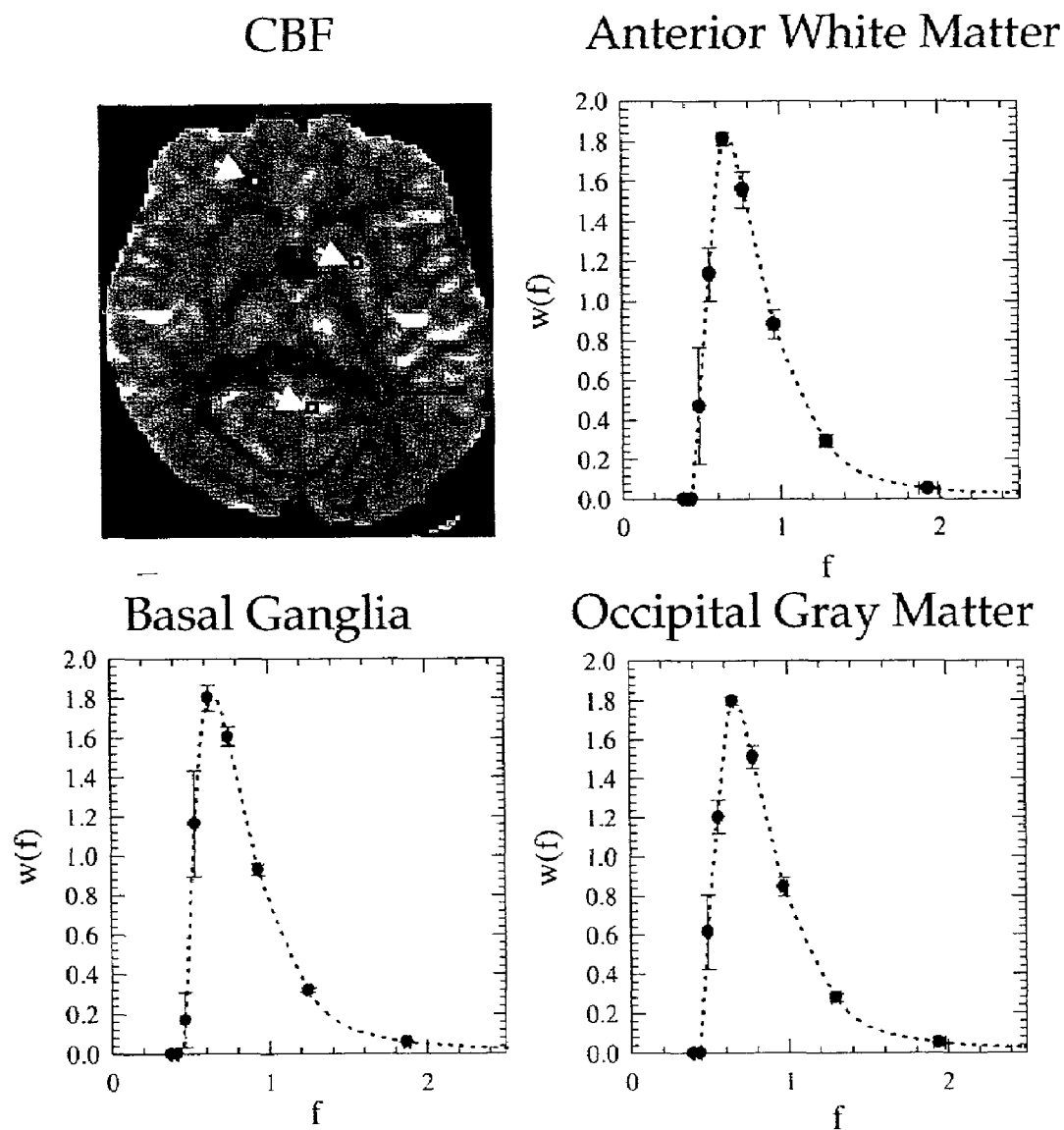
FIG. 12 shows the location and size of three regions chosen for determination of flow heterogeneity in volunteer 4.

FIG. 12 shows the location and size of three regions chosen for determination of flow heterogeneity in volunteer 4. The regions are overlaid on a CBF map calculated by the SVD-method to illustrate the contrast and spatial resolution of the techniques. Also shown are the corresponding flow heterogeneity plots derived from the three regions. The transit time and derived flow heterogeneity PDFs were found to be remarkably similar among regions and among volunteers. FIG. 13a shows all pairs of relative transit time t and corresponding h(t) measured for all regions in all 6 volunteers. FIG. 13b shows—under the assumption of equal capillary lengths—the corresponding plot of relative flow f and w(f) measured for all regions and volunteers. Due to this constancy across regions and subjects, the (f,w(f)) points were consequently averaged into 30 points (Full curve) and used as a global expression for flow heterogeneity in normal tissue in the subsequent model analysis. The parameterised w(f) is given in Table 1. The distribution of flows is markedly right-skewed, with the majority of capiliaries having flow rates less than the mean flow. The maximum probability is reached at roughly ⅔ of the mean flow.

Model Validation

Figure 14:
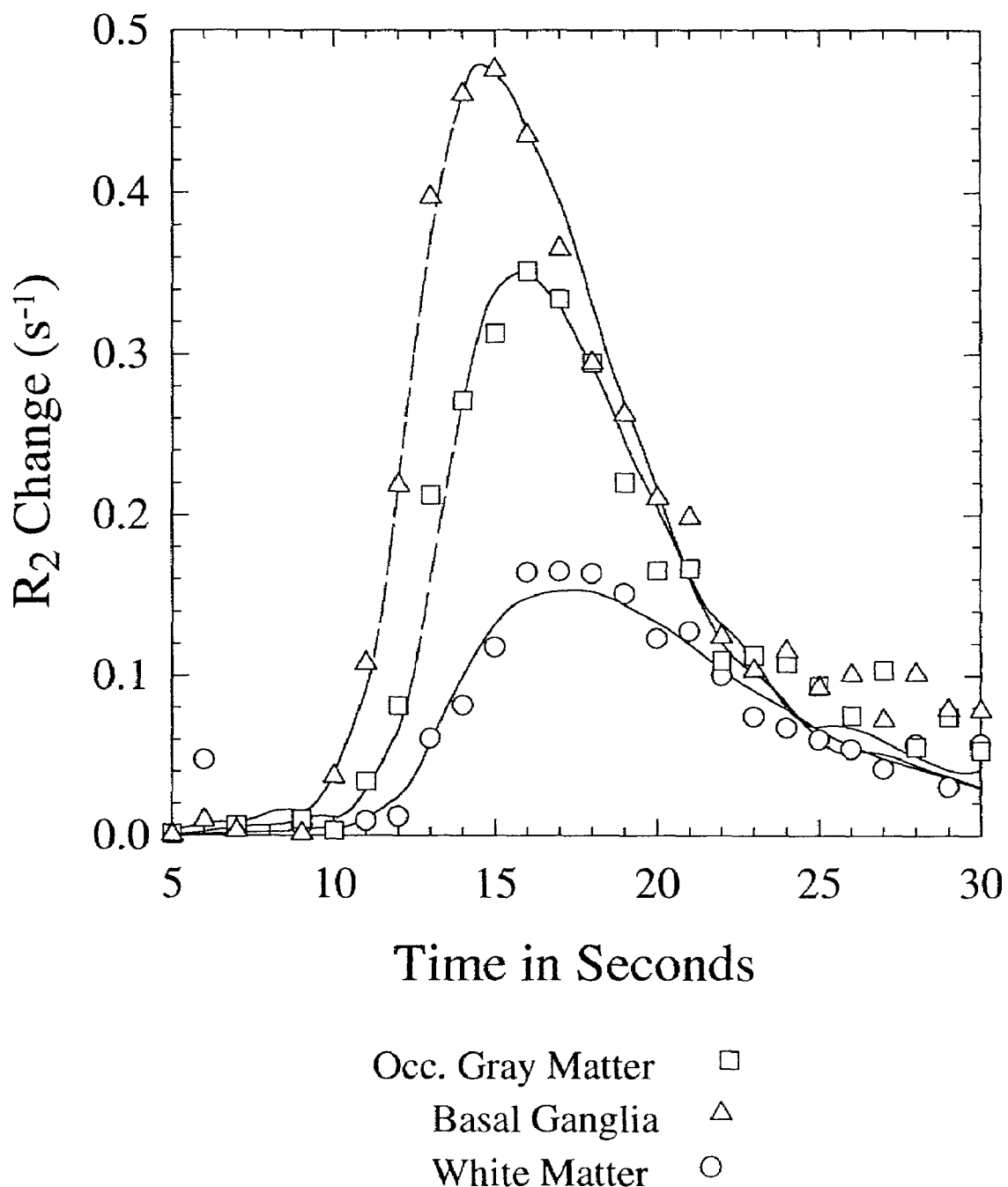
FIG. 14 shows a typical set of tissue concentration time curves as well as the fits provided by the model.

In the following, the experimentally determined flow heterogeneity PDF was applied, and the vascular transport is therefore described by only three parameters, $V_{art}$, $F_p$ and $V_p$. FIG. 14 shows a typical set of tissue concentration time curves as well as the fits provided by the model (Basal ganglia: CBF=60.3±1.0 (SE) ml/100 ml/min, Gray matter: CBF=48.5±1.2 ml/100 ml/min, white matter: CBF=19.5±0.8 ml/100 ml/min). Notice the model takes into account the observed earlier tracer arrival in tissue with higher flow rates. The quality of model fits to experimental data shown in FIG. 14 is typical for the patients examined. Table 5 shows the mean gray:white matter flow ratios for 8 regions. The mean gray:white flow ratio was 2.89±0.35 with the vascular model.

TABLE 5

Regional gray:white flow ratios in 6 volunteers

| Region | Volunteer no. | | | | | | |
|---|---|---|---|---|---|---|---|
| | 1 | 2 | 3 | 4 | 5 | 6 | Average |
| Basal ganglia | | | | | | | |
| left | 4.19 | 3.41 | 3.70 | 2.73 | 3.76 | 3.39 | 3.53 |
| right | 3.76 | 3.41 | 2.99 | 2.80 | 3.66 | 3.86 | 3.41 |
| Frontal medial | | | | | | | |
| left | 2.89 | 2.91 | 1.94 | 2.32 | 2.55 | 2.03 | 2.44 |
| right | 2.66 | 2.73 | 3.6 | 2.24 | 3.06 | 3.03 | 2.88 |
| Temporal | | | | | | | |
| left | 3.55 | 3.16 | 3.14 | 2.55 | 4.31 | 2.29 | 3.16 |
| right Occ.-temporal | 4.52 | 3.59 | 3.27 | 2.02 | 3.71 | 2.78 | 3.31 |
| left | 2.50 | 2.37 | 2.66 | 2.20 | 2.55 | 2.74 | 2.50 |
| right Occ. medial | 2.78 | 2.05 | 3.70 | 2.08 | 1.70 | 1.97 | 2.38 |
| left | 3.60 | 2.87 | 2.27 | 2.06 | 2.30 | 2.84 | 2.66 |
| right | 2.95 | 2.12 | 3.57 | 2.17 | 2.15 | 2.43 | 2.57 |
| Average | 3.34 | 2.86 | 3.08 | 2.31 | 2.97 | 2.74 | 2.89 |

Comparison with Model-Free Approach

Figure 15:
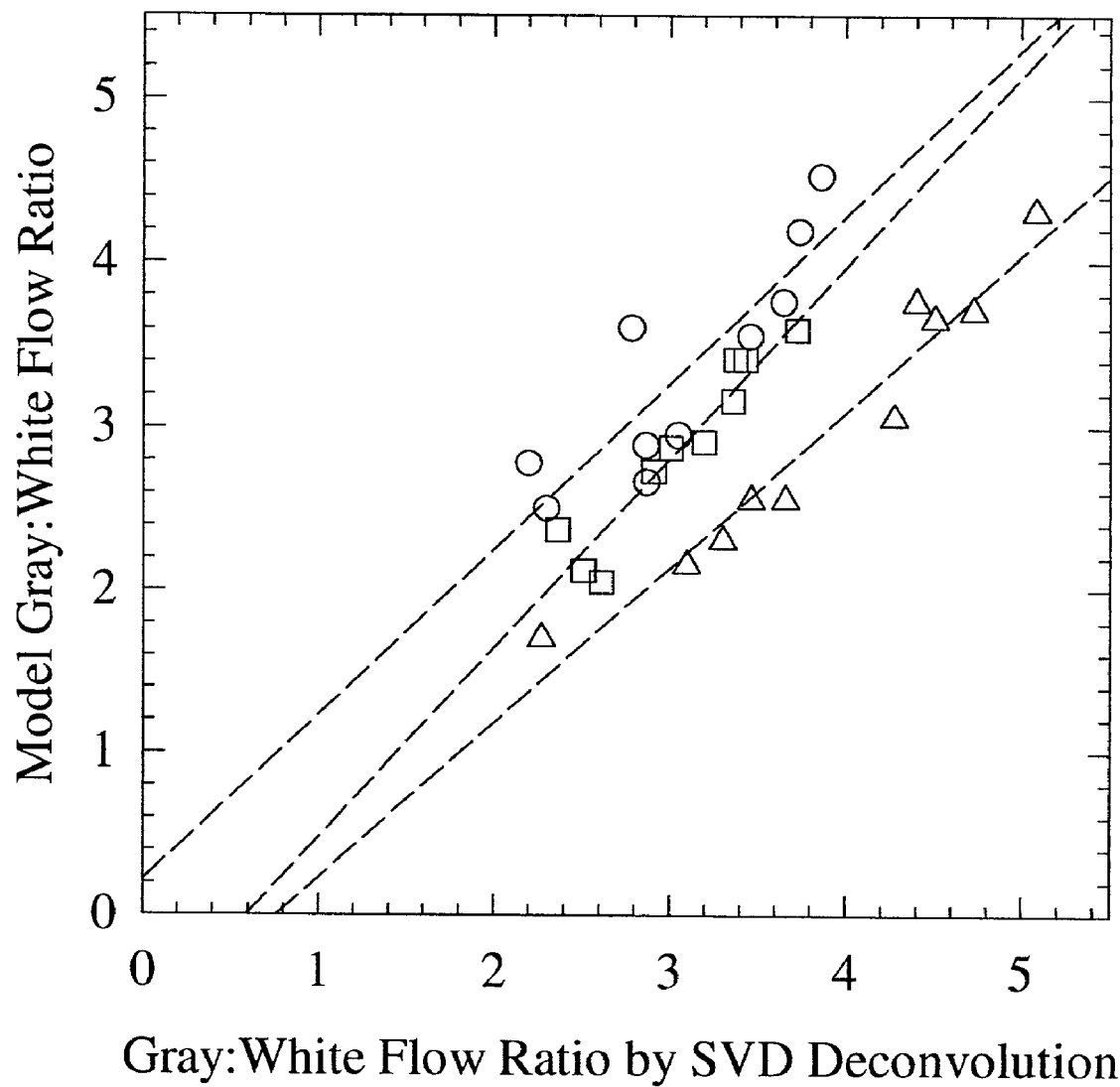
FIG. 15 shows gray:white matter flow ratios determined by the model approach plotted versus corresponding ratios in identical regions determined by the SVD approach.

FIG. 15 shows gray:white matter flow ratios determined by the model approach plotted versus corresponding ratios in identical regions determined by the SVD approach. The three volunteers were chosen based on a significant spread in individual, regional gray:white matter ratios, in order to facilitate comparison between approaches. In the figure, linear regression lines for each volunteer are shown (Volunteer 1: y=1.02+0.21 ($r^2$=0.75), Volunteer 2: y=1.16x−0.68 ($r^2$=0.91), Volunteer 5: y=0.95x−0.72 ($r^2$=0.95)). The line of identity was within the 95% confidence intervals of a common linear fit. Notice regional gray:white matter ratios using the two techniques all lie near the line of identity.

Sensitivity to Tracer Arrival Delays

Figure 16A:
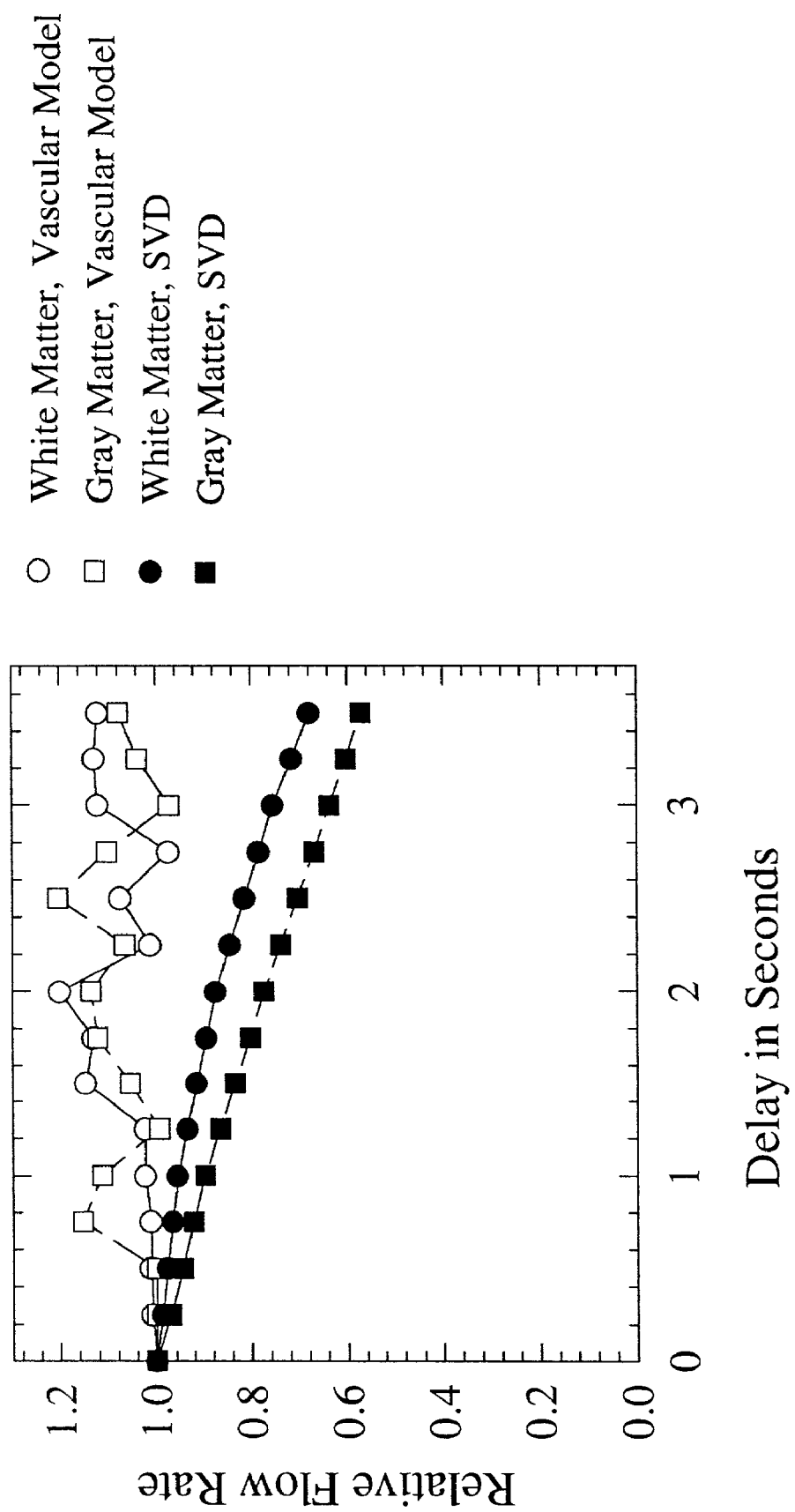
FIG. 16a shows the effect of AIF delay on fitted flow rates for the vascular model and the SVD approach, respectively.
Figure 16B:
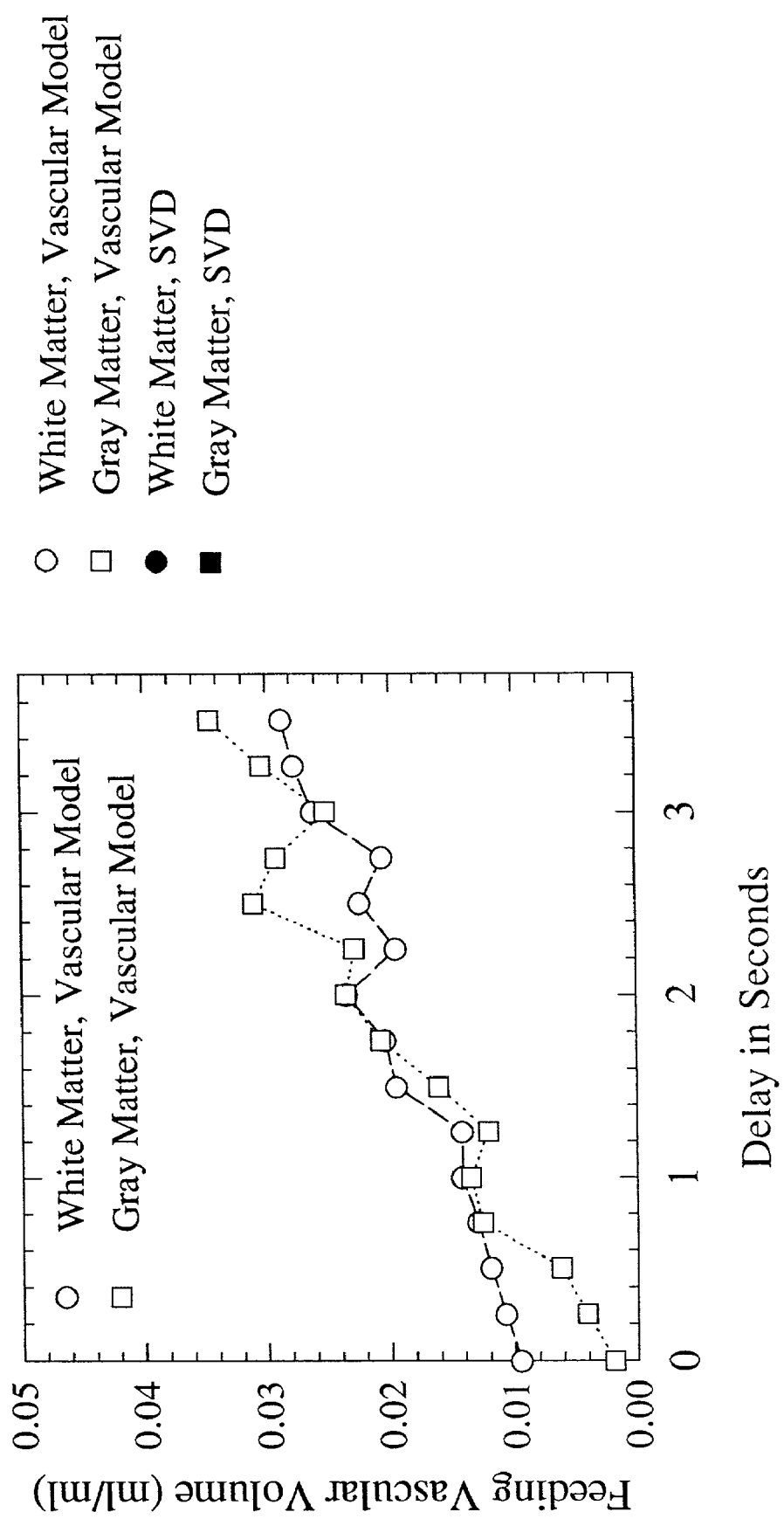
FIG. 16b shows the fitted feeding artery volume as a function of delay.

FIG. 16a shows the effect of AIF delay on fitted flow rates for the vascular model and the SVD approach, respectively. The gray and white matter tissue ROIs consisted of 90 image pixels (1.1 cc). Vascular model and SVD values were obtained from identical regions. The SVD approach progressively underestimates flow rates with tracer arrival delay. The relative underestimation is roughly proportional to the delay, reaching 25% for white matter and 35% for gray matter at a delay of 3 seconds, respectively. For the model approach, flow estimates are remarkably independent of delay FIG. 16b shows the fitted feeding artery volume as a function of delay. The vascular model interprets increasing delays as increased feeding vessel volume in accordance with the definition of the vascular operator. As vascular dispersion is a priori unknown in actual measurements, fitting was performed assuming a vascular dispersion RD=0.48, although the delay was simulated to be dispersion-less Notice fluctuations of fitted flow values around 1 is accompanied by fluctuations of the fitted vascular volumes. These fluctuations and the tendency of flow and vascular volume to co-vary are discussed further below.

Sensitivity to Noise and Initial Conditions

Figure 17A:
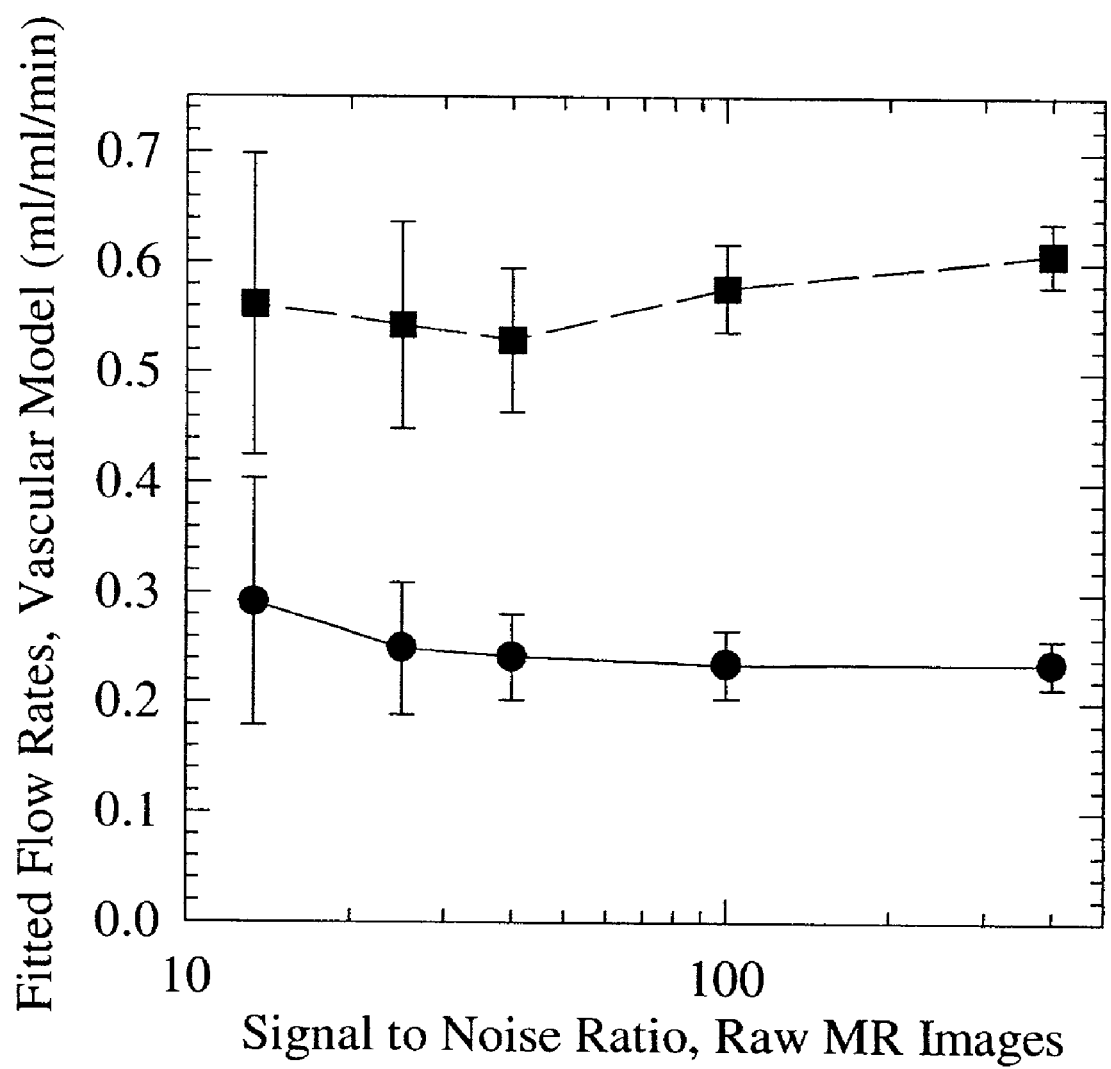
FIG. 17 shows the means and standard deviation of the fitted flow rates for two sets of simulated data ($V_{art}$–0.5, $F_p$=60 ml/100 ml/min, $V_p$=3%; $V_{art}$=0.5%, $F_p$=20 ml/100 ml/min, $V_p$=2%), using the model (FIG. 17a) and SVD (FIG. 17b) approach, respectively.
Figure 17B:
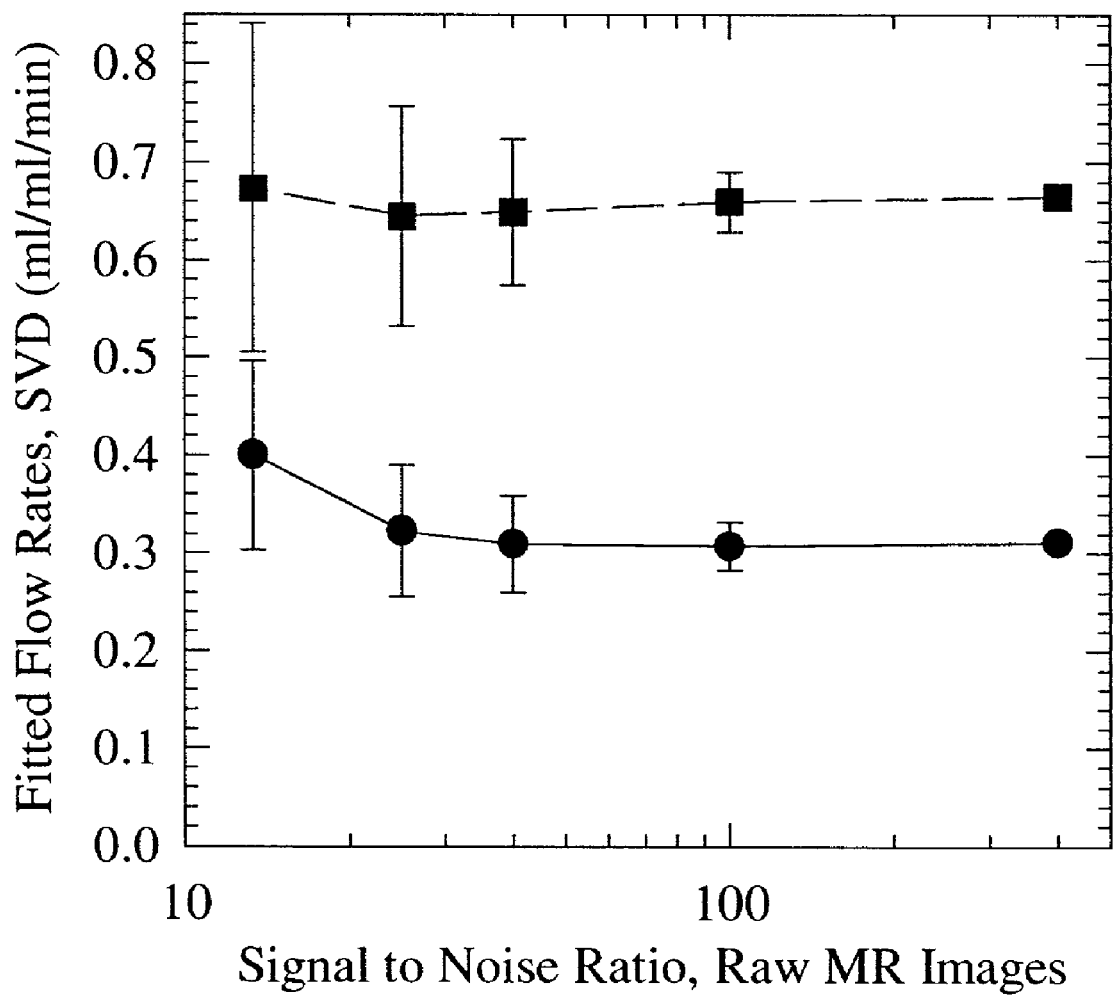

FIG. 17 shows the means and standard deviations of the fitted flow rates for two sets of simulated data ($V_{art}$=0.5%, $F_p$=60 ml/100 ml/min, $V_p$=3%; $V_{art}$=0.5%, $F_p$=20 ml/100 ml/min, $V_p$=2%), using the model (FIG. 17a) and SVD (FIG. 17b) approach, respectively. Raw image data noise was varied from that of typical, clinical data (~12) to 400. The SVD approach overestimates flow rates somewhat for this choice of model parameters, whereas the vascular model fits are roughly equal to the input parameters. The uncertainty (error bars in FIGS. 17a and 17b indicate one standard deviation, derived from the simulated data) on fitted flow rates display the expected increase as a function of increasing raw image data noise.

Figure 18:
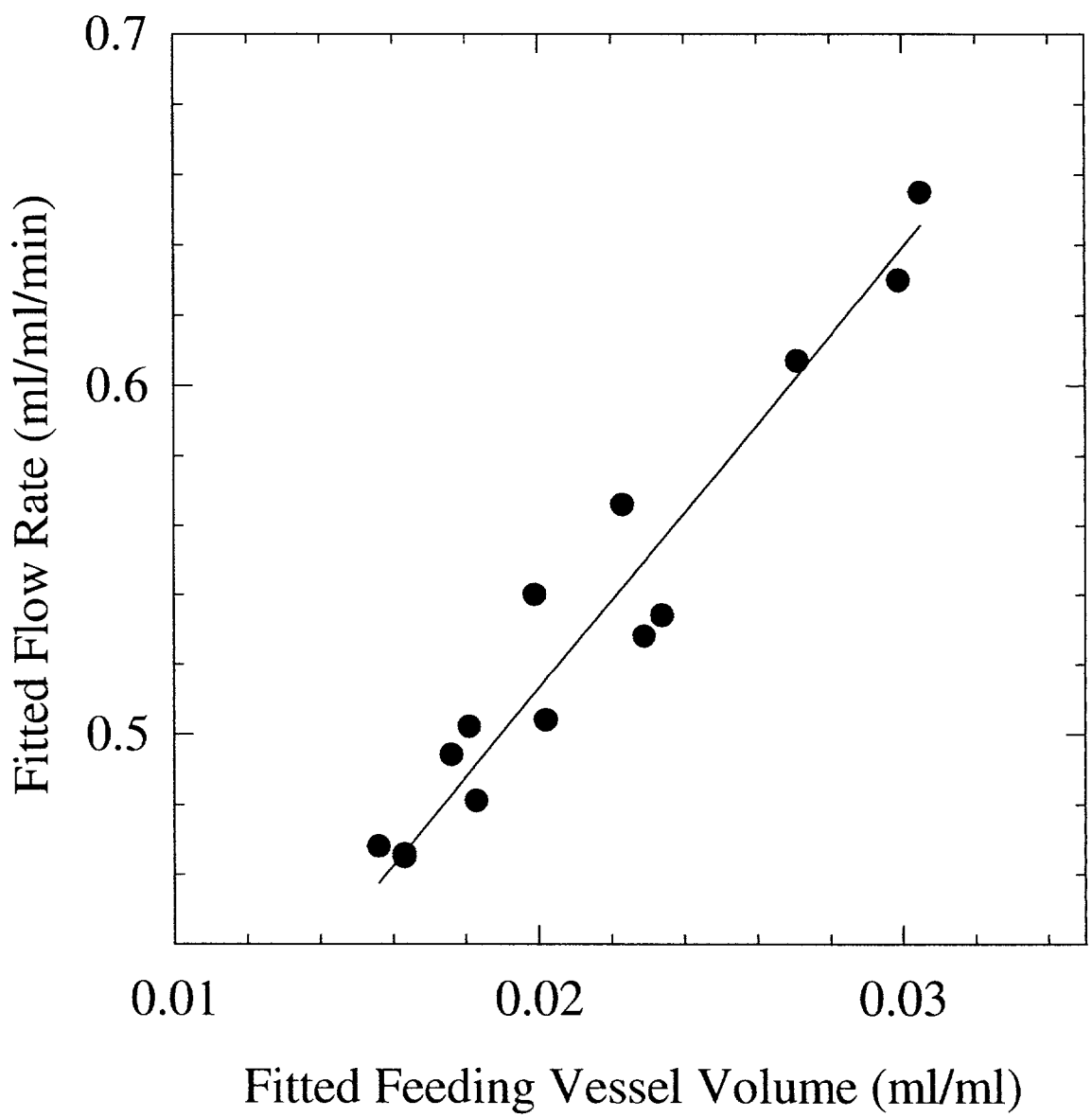
FIG. 18 shows fitted flow rates versus corresponding fitted feeding artery volumes from simulated curves with SNR-40.

For low SNR, error bars are roughly equal in size for the SVD and model approach, respectively. For high SNR, however, the uncertainty on vascular model fits did not reach zero as was the case for the SVD approach. To investigate whether factors other than noise contributed to the observed behaviour, the dependence of model fits on initial conditions and the tendency of parameters to co-vary was analysed. The fraction of fits, where initial conditions were found to significantly affect the fitted flow rates (defined as cases where two different initial conditions resulted in fitted flows that differed by more than 10% from their mean) was found to be negligible for SNR above 20. For lower SNR, 15–20% of fits gave ambiguous results. Therefore, the standard deviations for the low SNR may be somewhat underestimated due to bias by the choice of initial conditions. During simulations, fitted feeding artery volumes and fitted tissue flows were found to co-vary: high, fitted flow rates were hence often accompanied by high arterial volumes. FIG. 18 shows fitted flow rates versus corresponding fitted feeding artery volumes from simulated curves with SNR=40. This pattern of co-varying fitted flow rates and feeding artery volumes was found at all noise levels. It was found that varying flow and feeding artery volume in proportion lead to only small changes in the shape of the resulting concentration time curve. Therefore, the presence of modest experimental noise leads to relatively large uncertainties in fitted flow rates. This is thought to explain the unexpected, large standard deviation of flow estimates at high SNR for the vascular model, as well as the fluctuations around unit relative flow in FIG. 16.

Discussion

Overall Validity of Model

The vascular model, after incorporation of the experimentally determined heterogeneity PDF, provided excellent fits to the experimental data. The model fits of CBF yielded a mean gray:white flow ratio of 2 8±0.35, in agreement with the PET literature ratio of 2.65 for subjects of similar age (Leenders 1990). The ratios were also in good agreement with those found using the model-free approach. In contrast to the SVD approach, the model approach provided fits to experimental data that were essentially independent of vascular delay. The model was simplified considerably by the use of one flow heterogeneity PDF for all types of tissue. By characterising the model by only three parameters, a remarkable stability of the model was obtained, even compared to the pixel-by-pixel based SVD approach. Co-varying vascular volume and flow rate in model fits to low SNR data was found to be a major contributor to uncertainty in model fits of CBF. Below, the individual elements of the model are discussed in further detail.

Model Considerations

The model presented here differs slightly from that previously described by Kroll et al. (Kroll 1996) in the heart. Kroll et al. (Kroll 1996) described the arteriolar and capillary compartments separately, assigning fixed relative dispersion and variable volumes to the arteriolar vascular paths, and a fixed volume to the capillary bed. In the brain, capillary density varies greatly among different tissue types. For the purpose of obtaining a robust model for all types of brain tissue with the same choice of basic model parameters, the microvascular volume was kept as a free parameter. In terms of vascular transport, the models are similar, except that in the model presented here, dispersion takes place only in the large vessel, whereas small vessel dispersion is accounted for by the flow heterogeneity PDF. Despite the simplification of the model, it is likely that, by limiting the number of vascular elements and thereby the number of free parameters, the stability of the model to noise has increased significantly, as outlined in the analysis above. The robustness of the model to experimental noise is imperative to ultimately study CBF at high spatial resolution. Kroll et al. assumed that only small vessel tracer levels are observed by the residue detection (Kroll 1996). Here, this assumption is further justified by the inherent sensitivity of susceptibility contrast to microvessels (Fisel 1991; Weisskoff 1994; Boxerman 1995).

Vascular Transport and Dispersion Term

As discussed elsewhere (Østergaard 1996b), nonparametric deconvolution approaches do not allow separation of macrovascular transport and microvascular retention. Therefore, modelling vascular retention is necessary, whenever vascular transport significantly changes the input bolus shape upstream of the AIF measurement site. The vascular transport operator model used in the present model is generally accepted for modelling normal major vessel transport. The advantage of including vascular transport in the kinetic modelling is demonstrated in FIG. 14: The fact that tracer arrives earlier in tissue with high flow rate due to a faster feeding vessel transit is accounted for by the model approach, unlike the model-free SVD approach. The difficulty in introducing this operator lies mainly in the fact that the transfer functions of the major vessel and the microvascular network are very similar. This, in turn, leads to the difficulty in separating vascular volume and flow, as observed in the simulations (FIG. 18). The analysis presented here also suggest that this effect contributes significantly to the uncertainty of flow estimates, even at modest noise levels, just at it may play a role in the dependency upon initial conditions of fitted flow rates. These findings are in agreement with those previously reported by Kroll et al (Kroll 1996). In cerebrovascular diseases, blood may pass through stenoses with marked turbulence, or through irregular collateral paths upstream of the arterial sampling site. In these cases, the vascular operator may not be adequate, and the vascular transport function should ideally be measured independently. Indeed, novel MR techniques detecting the inflow of spin labelled arterial blood to a given brain region may ultimately provide this information (Wong 1997). Such independent measurements would serve to avoid the interdependence of flow and vascular volumes using vascular models, or alternatively allow application of the model-free SVD approach. In severe cases, however, vascular dispersion may dominate total tracer retention, in which case estimates of flow rate by residue detection of an intravascular tracer become uncertain (Østergaard 1996b; Kroll 1996).

Flow Heterogeneity

Figure 19:
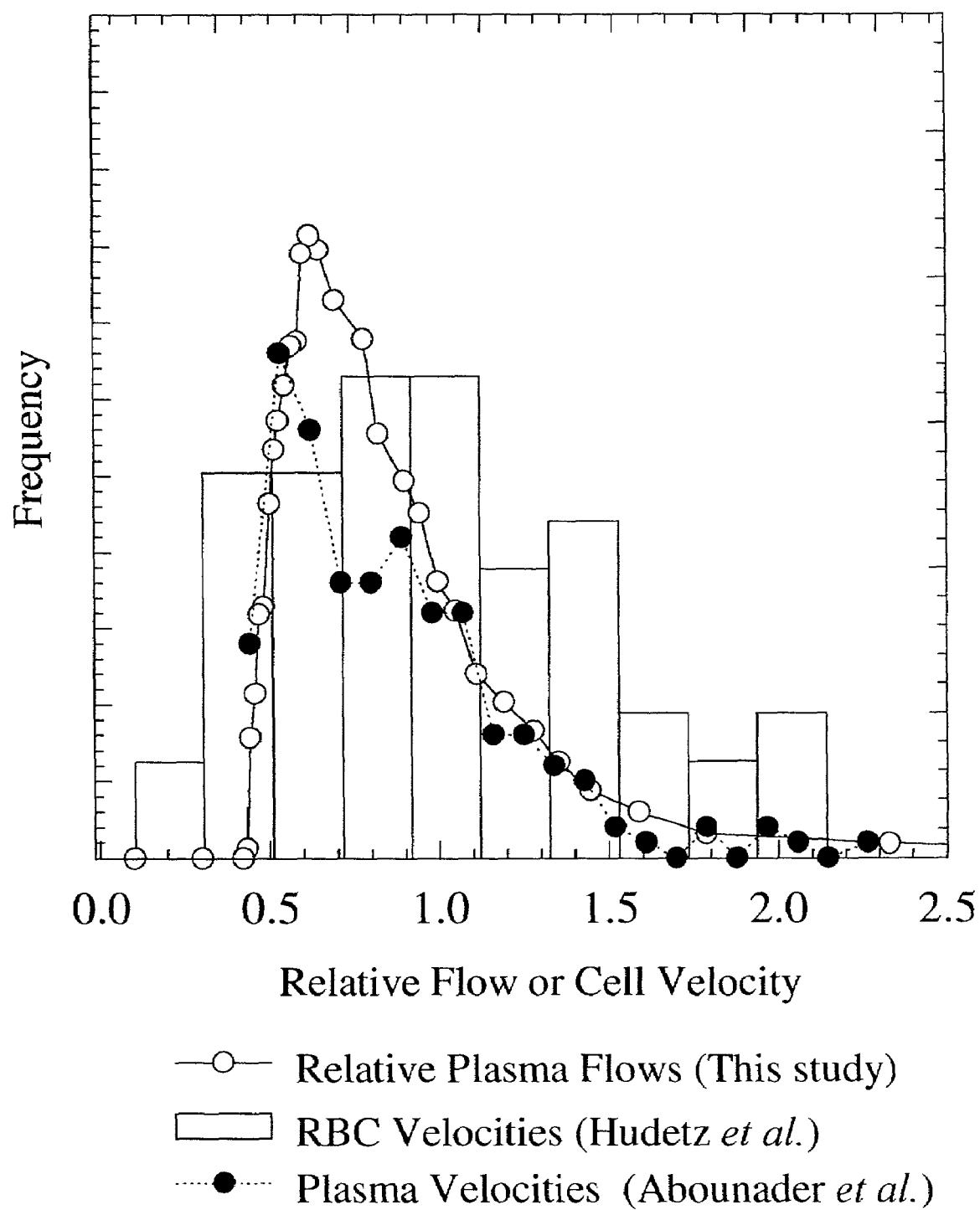
FIG. 19 shows the findings of Hudetz et al. and Abounader et al. along with the relative plasma flows.

Reports of cerebral flow heterogeneity are mainly based on invasive measurements of plasma or red blood cell velocities in rats. Abounader et al. utilized bolus injection of a plasma marker followed by decapitation, deriving plasma flow velocity from capillary filling in histology (Abounader 1995). Hudetz et al determined the frequency of red blood cell (RBC) velocities in capillaries using intravital video microscopy (Hudetz 1997). Both found the distribution of blood elements to be very heterogeneous, with a right-skewed shape. FIG. 19 shows their findings along with the PDF determined here. The data of Hudetz et al (Hudetz 1997) were normalised as the relative flow PDF (See Theory, Equation 9). From the data of Abounader et al. (Abounader 1995), a normo-capnic data set was chosen, and axes scaled to facilitate comparison with the other curves (plasma flow units did not allow direct normalisation). It should be noticed that these measurements are not directly comparable. First, plasma and RBCs follow different paths through the capillary network, so the measurements presented here should be more comparable to the plasma velocity measurements. Secondly, the flow distribution curve derived in this study assumes equal capillary lengths. Although the relationship between capillary plasma flow and flow velocity is a complex function of capillary length and architecture, a finite distribution of capillary lengths is likely to result in blood velocities being more dispersed than relative capillary flows (As seen when comparing the PDF presented here with the RBC velocity study). The similarity of the present measurements with these independent, invasive methods lends hope to the use of this approach in describing normal microvascular dynamics. In altered physiological states or disease, the flow heterogeneity may not be as constant among tissue types as found in this study. Abounader et al. (Abounader 1995) determined the heterogeneity of microvascular flow at different degrees of hypercapnia, and found that plasma flow became more homogenous at higher flows. A similar finding for red blood cell velocities was reported by Hudetz et al (Hudetz 1997). This could be the case in disease as well, and caution should therefore be exercised in choosing flow heterogeneity PDF for use with vascular models in these cases. The model-free approach to determine flow heterogeneity PDF presented here may provide insight with respect to the distribution of relative flows in these cases. Using this approach, it should be kept in mind solving Equation 1 belongs to a class of so-called inverse problem, meaning that any noise in measured tissue concentrations may lead to large changes in the resulting residue function. As suppression of noise inevitably causes loss of underlying information, the SVD deconvolution therefore may not yield the exact shape of the underlying residue function. Likewise, one may not be able to distinguish slightly different flow heterogeneity PDF based on noisy measured concentration time curves. Although the flow heterogeneity PDF and derived flow rates were found in agreement with independent findings, it is therefore important to further validate the approach presented here.

Utility of Vascular Models

Although cerebral blood flow itself is an important index of brain function, the heterogeneity of microvascular flow and transit times described here may be a more important determinant of cerebral metabolism. As discussed by Kuschinsky et al., the degree of heterogeneity among capillary paths determines the net capillary-to-tissue concentration gradients necessary to drive delivery of nutrients (Kuschinsky et al., 1992). Indeed, regulation of capillary flow heterogeneity may play a major role in the brains ability to increase e.g. oxygen delivery to meet cellular metabolic demands (Kuschinsky et al., 1992). This issue can be addresses in great detail by combining flow heterogeneity measurements with spatially distributed models of oxygen exchange (Li 1997). The analysis presented here, combined with these models, may ultimately lead to a more extensive understanding of, for example, the fundamental limitations of oxygen delivery in stroke, where the survival of tissue may partially depend on the ability to increase oxygen extraction by an increased mean transit time. Also, modelling the exact relationship between cellular oxygen consumption and vascular oxygen levels may facilitate a quantitative metabolic interpretation of deoxyhemoglobin concentration changes observed by functional magnetic resonance imaging (Kwong 1992).

EXAMPLE 4

Magnetic Resonance Imaging Measurements of Flow Heterogeneity Demonstrate High Risk of Infarction in Acute Stroke Summary of the Example The ability of brain tissue to survive ischemic episodes is believed to be related to changes in the dynamics of capillary blood flow. Using a novel magnetic resonance imaging based method to measure microvascular transit time dynamics, the flow heterogeneity and tissue mean plasma transit times was examined in 11 patients presenting with acute (<12 hours after symptom onset) stroke. In normal brain tissue, the distribution of relative flows was found to be markedly skewed towards high capillary flow velocities. Within regions of decreased cerebral blood flow, plasma mean transit times were prolonged. Furthermore, subregions were identified with significant loss of the high-flow component of the flow distribution, thereby causing increased homogeneity of flow velocities. These findings are in agreement with independent, invasive measurements of flow heterogeneity in states of decreased perfusion pressure in animal models. In parametric maps quantifying the acute deviation of flow heterogeneity from that of normal tissue, areas of extreme homogenisation of capillary flows predicted final infarct size on follow-up scans in 10 out of 11 patients. Flow heterogeneity and plasma mean transit time can be rapidly assessed as part of a routine clinical magnetic resonance examination, and may provide a tool for individual planning of stroke treatment, as well as in targeting and evaluating emerging therapeutic strategies.

Background

Acute stroke is the third leading cause of death, and the leading cause of adult disability. Emerging therapeutic strategies seek to minimise the progression of tissue damage in the acute phase of the disease. Methods to rapidly assess the severity and later progression of acute stroke in individual patients are therefore highly desirable to plan individual treatment, as well as to evaluate novel therapeutic strategies.

In acute cerebral ischemia, delivery of nutrients is severely compromised, and tissue survival therefore depends on tissue regulatory mechanisms to meet metabolic needs. Studies using positron emission tomography (PET) have shown that mean blood transit time (MTT) and, with further drop in cerebral perfusion pressure, also the oxygen extraction fraction (OEF) are increased in 'tissue at risk' of infarction (Gibbs 1984; Baron 1981). Although the relationship between prolonged blood MTT and OEF remains unclear, both phenomena are believed to reflect underlying regulatory mechanisms attempting to compensate for a decrease in perfusion pressure.

One mechanism for vasoregulatory control is believed to be the ability to alter the heterogeneity of blood transit times and thereby the mean capillary concentration of substances diffusing from blood to tissue (Kuschinsky and Paulson 1992). Animal experiments in rats have revealed decreased flow heterogeneity during whisker-barrel stimulation (Vogel and Kuschinsky 1996), indicating that this may be the mechanism underlying the normal brain's striking ability to meet increased metabolic needs during functional activation. Furthermore, Hudetz et al. demonstrated that graded decrease in perfusion pressure causes progressive loss of high-flow components, thereby decreasing total flow heterogeneity (Hudetz 1996). Decreasing-flow heterogeneity therefore seems to play a crucial role in maintaining sufficient concentration gradients to drive diffusion of nutrients such as oxygen from blood into the cells (Kuschinsky and Paulson 1992). This suggests that blood mean transit time and the degree of flow heterogeneity are important indices to assess and further understand the ability of the brain to survive ischemic episodes.

The heterogeneity of flows in normal volunteers by magnetic resonance imaging (MRI) residue detection has recently been studied (Example 3 (Østergaard 1999)). It was found that the probability density function (PDF) of relative flows was remarkably constant within and among normal volunteers. In this study, magnetic resonance residue detection was used to study plasma mean transit times as well as flow heterogeneity patterns in patients presenting with acute stroke. Furthermore, these findings were correlated with later neuronal death by comparing initial diffusion weighted imaging (DWI) with follow-up MRI or computed tomography (CT).

The present findings show that flow heterogeneity changes, previously only detectable by invasive microscopy in animal models, can be assessed by a 2-minute examination as part of routine MRI of acute stroke patients. Furthermore, the degree of heterogeneity change relative to normal tissue is a powerful predictor of later neuronal death, suggesting flow heterogeneity may provide an important diagnostic tool in stroke patient management.

Materials and Methods

Patient Data

All patients were treated with best medical management, but did not receive tPA or other thrombolytic traeatment. DWI and CBF results for these patients are reported earlier (Sorensen 1998).

Imaging was performed on a GE Signa 1.5 T imager (General Electric, Waukesha, Wis.) retrofitted for EPI capabilities (Instascan, Advanced NMR Systems, Wilmington, Mass.).

MRI Perfusion Protocol. Determination of CBV, CBF, MTT, and flow heterogeneity. Perfusion imaging was performed using spin echo (SE) or gradient echo (GE), echo planar imaging (EPI) with a time of repetition (TR) of 1.5 seconds, and a time of echo (TE) of 100 ms (50 ms for GE EPI). The slice thickness was 5 mm with an in-plane resolution of 1.56 mm by 1.56 mm in a 40 by 20 cm field-of-view (FOV). In 10 slices, a total of 52 images were acquired, starting 15 seconds before i.v. injection of 0.2 (SE-EPI) or 0.1 (GE-EPI) mmol/kg Gd-based contrast agent. Intravascular contrast agent concentrations, C(t), were quantified assuming a linear relationship between concentration and change in transverse relaxation rate, $\Delta R_2$ (Villringer 1988; Weisskoff 1994). The shape of the arterial input function (AIF) was determined from feeding arterial branches either adjacent to the area of DWI abnormality or at the contralateral middle cerebral artery (MCA), and were, identified in the image slice as pixels displaying early concentration increase after contrast injection (Porkka 1991). The tissue residue function (or impulse response function) was calculated by deconvolving the tissue concentration time curve by the AIF, using singular value decomposition (SVD) (Østergaard 1996a; Østergaard 1996b). CBF was determined as the height of the deconvolved tissue curve. CBV was determined by the area under the tissue concentration time curve, as previously described (Rosen 1990), and the plasma mean transit time (MTT) formed as the ratio CBV/CBF (Stewart 1894). Finally, the distribution of tissue transit times in each imaging voxel was determined as the slope of the residue function, and by assuming equal lengths of capillary paths, the corresponding probability density function (PDF) of relative flows was determined by means of the central volume theorem (Stewart 1894; Example 3 (Østergaard 1999)). In order to quantify and compare the deviation of the experimentally determined PDF from that found in normal brain, a Kolmogorov-Smirnov test was performed, comparing the flow PDF in a given pixel to that previously determined in normal tissue (See Results, FIGS. 20a, 20b and 20c) (Press 1992; Example 3 (Østergaard 1999)). The corresponding p-value (Null-hypothesis: flow heterogeneity distribution is equal to that of normal tissue) was considered statistically significant if p<0.01 (Without Bonferoni correction).

Initial and Final Infarct Sizes.

At the initial scan, infarct size was assessed by diffusion weighted imaging (DWI) (Moseley 1990), acquired using single-shot EPI (TR 6 s, TE 118 ms) with diffusion weighting applied in 6 directions. By combining low (b=3 s/mm$^2$) and high b-values (ranging from 892–1221 s/mm$^2$), the entire diffusion tensor was sampled. Measurements were performed in 17–20 6 mm thick slices with 1 mm interslice gap, with an in-plane resolution of 1.56 mm to cover the whole brain. The resulting isotropic (tensor trace) diffusion weighted image was used in assessing initial infarct size. Final infarct size was assessed from DWI images acquired 2–5 days after the infarct, from $T_2$ or FLAIR MR images acquired at least 5 days after the infarct, or from CT images acquired more than 5 days after the infarct if no MRI was available.

Volumetric Analysis

Using a semi-automatic image analysis software package (ALICE, Hayden Image Processing Group, Boulder, Colo.), volumes of decreased diffusion, prolonged MTT and abnormal p (p<0.01), respectively were measured by manually drawing regions of interest (ROI) around the lesions on the corresponding maps, multiplying the lesion areas by the slice thickness plus inter-slice gap. We did not attempt to co-register initial and follow-up studies.

Results

Eleven hyperacute stroke patients, 7 male and 4 female, with mean age 61 (range 33–80) years, were examined within 12 hours of symptom onset (Table 6). All patients showed diffusion abnormalities on the initial DWI (Moseley 1990), consistent with ischemic neuronal death prior to the initial scan. Furthermore, all patients showed greater volumes of decreased cerebral blood flow (CBF) and/or increased MTT in the hemisphere of infarction.

TABLE 6

| Patient | Age/sex | Hours |
|---|---|---|
| 1 | 33 M | 4.5 |
| 2 | 78 F | 3 |
| 3 | 55 M | 2 |
| 4 | 53 M | 3 |
| 5 | 72 F | 2.5 |
| 6 | 64 F | 5.5 |
| 7 | 79 M | 7.0 |
| 8 | 80 F | 11.0 |
| 9 | 45 M | 4.0 |
| 10 | 65 M | 11.5 |
| 11 | 45 M | 6.5 |

Age, sex, time of initial MRI for 11 acute stroke patients. Patient 9 showed spontaneous reperfusion of the occluded vessel on the follow-up MR angiography.

Flow Heterogeneity Findings

Figure 20A:
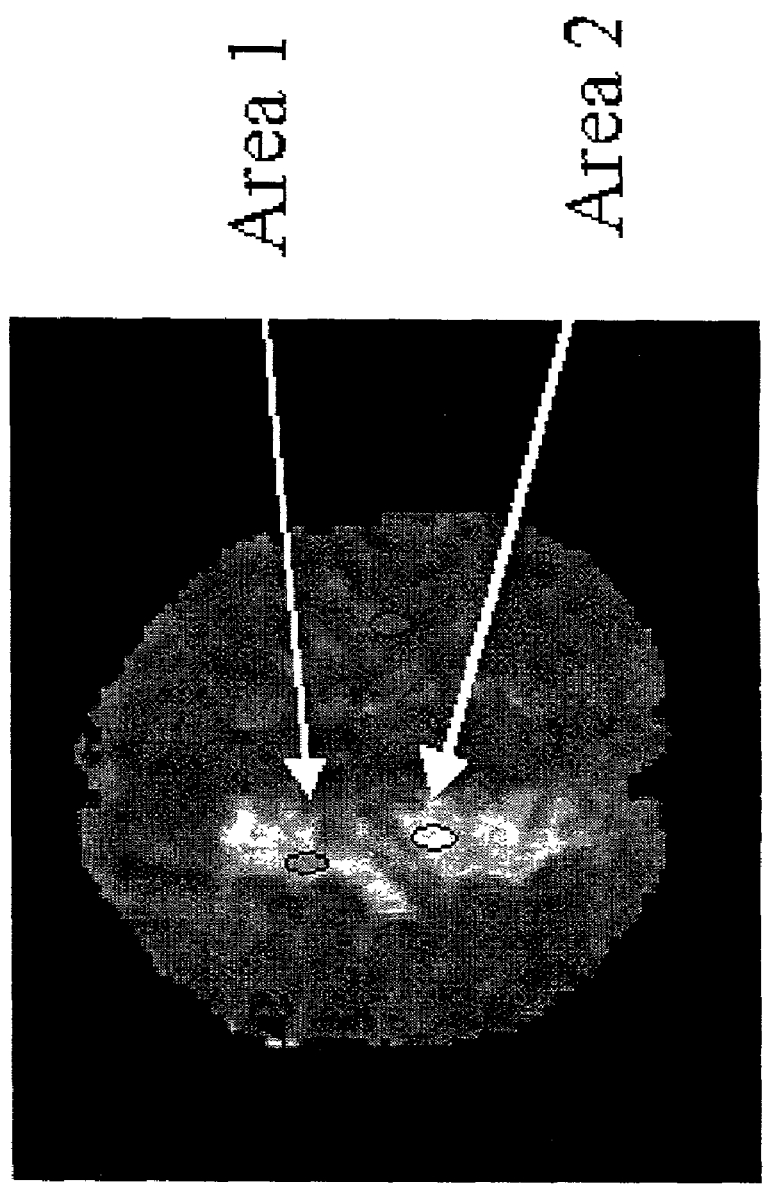
FIGS. 20a, 20b, and 20c show a typical pattern of patient 6.
Figure 20B:
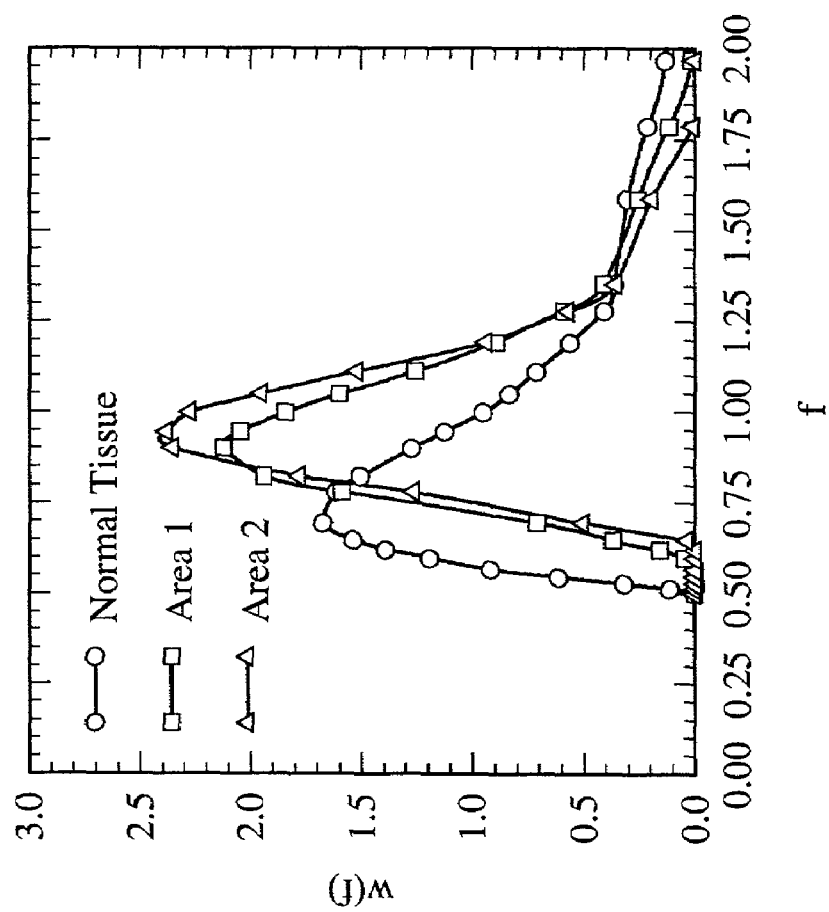
Figure 20C:
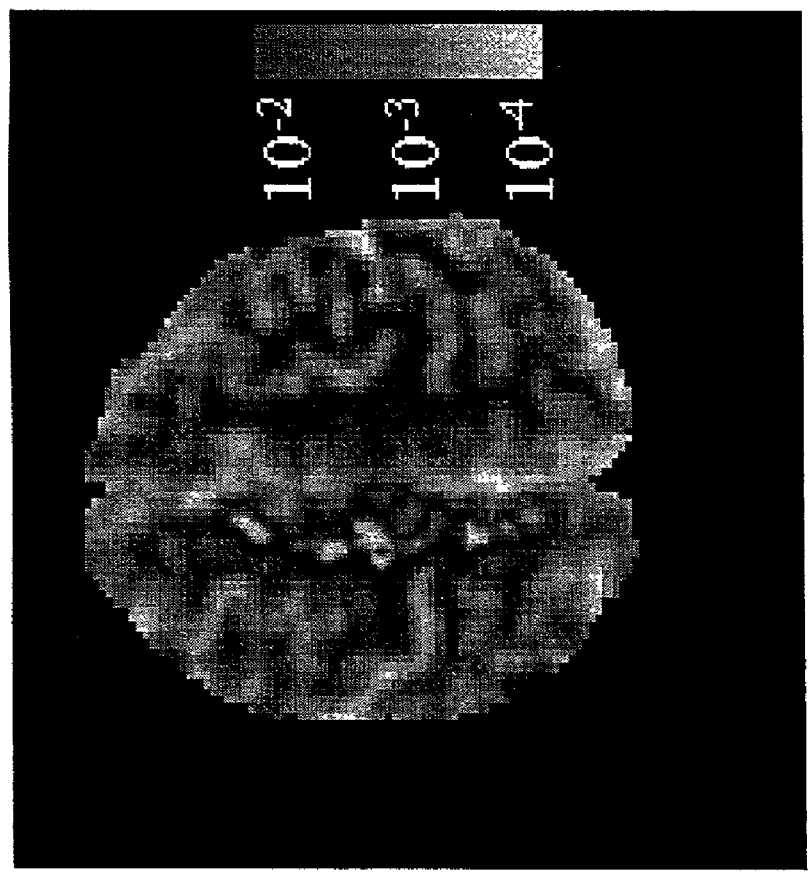

Outside volumes of prolonged MTT, the shape of the tissue flow PDF was similar to that previously found in normal volunteers, namely a right-skewed distribution with a distinct distribution of high flow rates. Inside volumes of prolonged mean transit times, the shape of the flow PDF was either like that of normal tissue, or showed distinctive loss of the high-flow portion of the PDF. To illustrate the first type, FIGS. 20a, 20b, and 20c show a typical pattern in patient 6. This patient, a 64 year old female, was examined 5.5 hours after onset of left leg weakness, and showed prolonged MTT corresponding to the anterior cerebral artery territory (FIG. 20a). FIG. 20b shows the flow heterogeneity plots for normal brain tissue as well as two regions of prolonged mean transit time (Areas are indicated on the MTT map with numbers corresponding to the PDF curves). The flow PDF in normal tissue was markedly right-skewed, and matched the shape previously found in normal volunteers (Example 3 (Østergaard 1999)). The volumes of increased MTT displayed PDFs with a more symmetric shape, with a tendency to loose the high-flow population found in normal tissue. The degree of symmetry varied within the volume of increased MTT. The deviation from the normal PDF was subsequently quantified by a Kolmogorov-Smirnov test, yielding the probability p that the curve belong to the distribution of relative flows of normal tissue (from Example 3 (Østergaard 1999)). In FIG. 20c, areas with large deviations of the PDF from that of normal tissue ($p<0.01$) are shown by a colour coded overlay of p onto the acute CBF map. Based on the previous experience (Example 3 (Østergaard 1999)) a significance level of $p<0.05$ displays few PDF abnormalities in normal tissue, except in major vessels. Therefore, $p<0.01$ was chosen to highlight highly significant deviations from normal flow heterogeneity PDF.

MTT, Flow Heterogeneity and Later Infarction

Figure 21A:
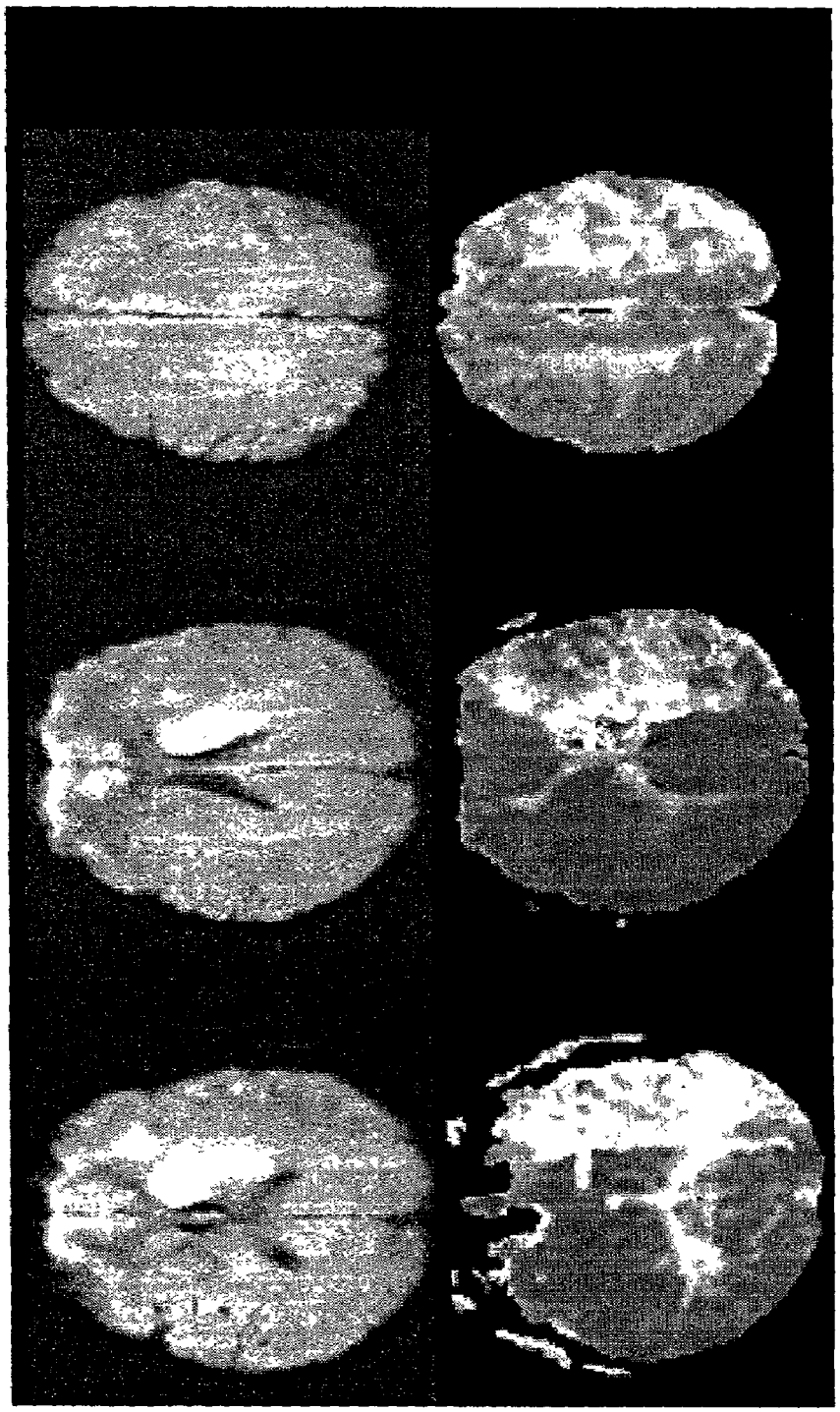
FIGS. 21a and 21b show the initial DWI, initial MIT, initial p/CBF and follow-up FLAIR images of patient 11.
Figure 21B:
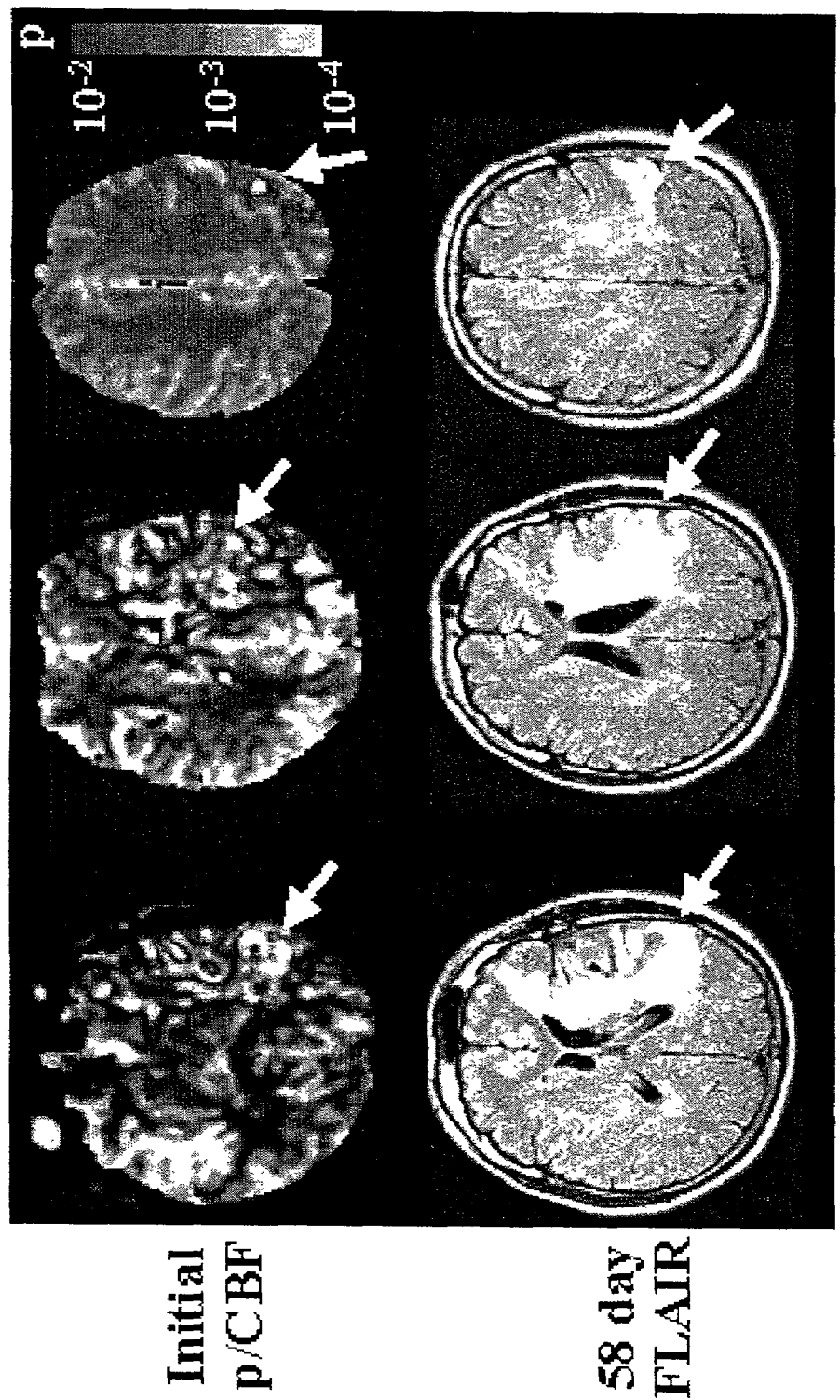
Figure 22:
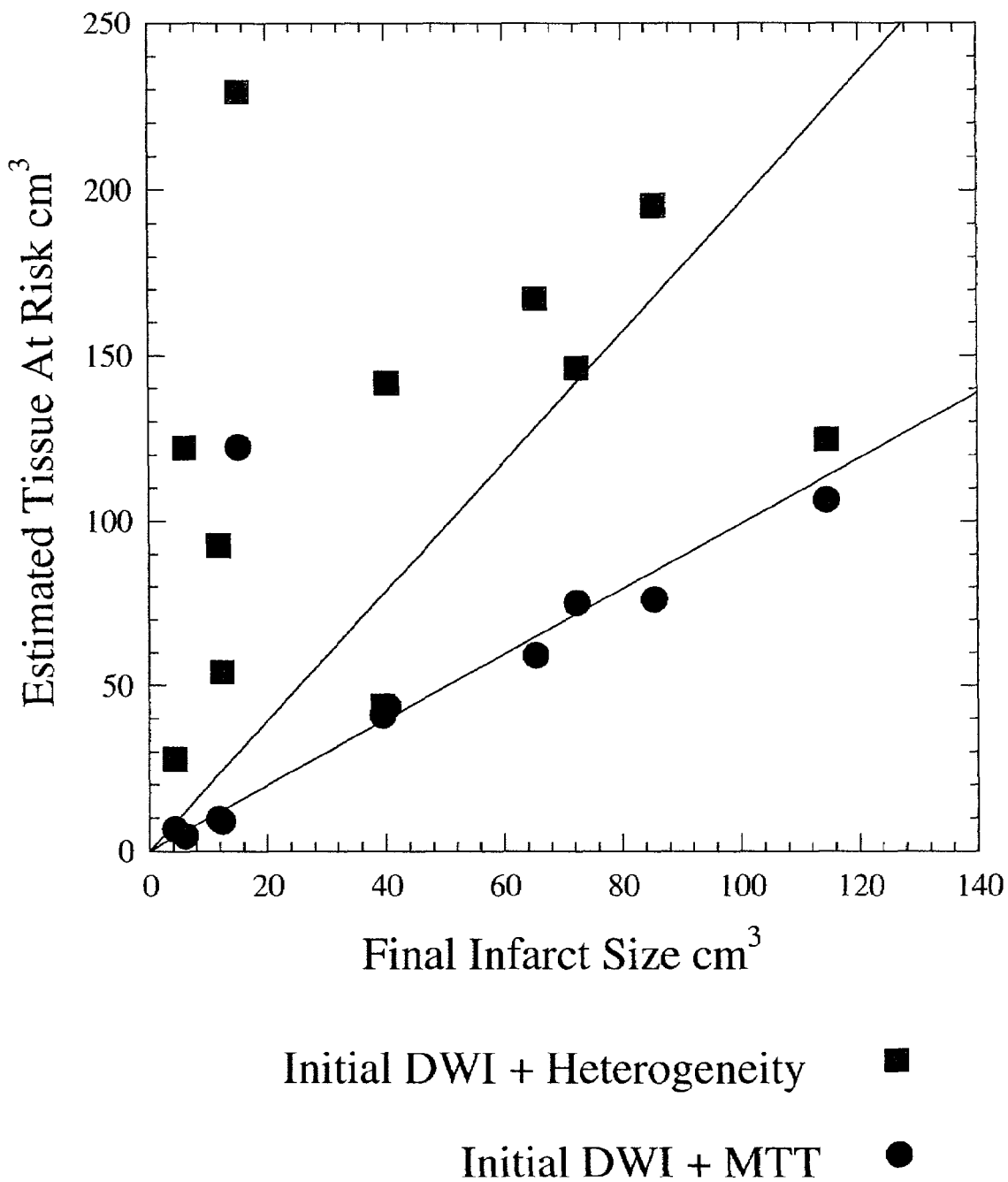
FIG. 22 shows that final infarct volumes are compared to the initial abnormalities of DWI+MTT and DWI+p maps, repectively.
Figure 23A:
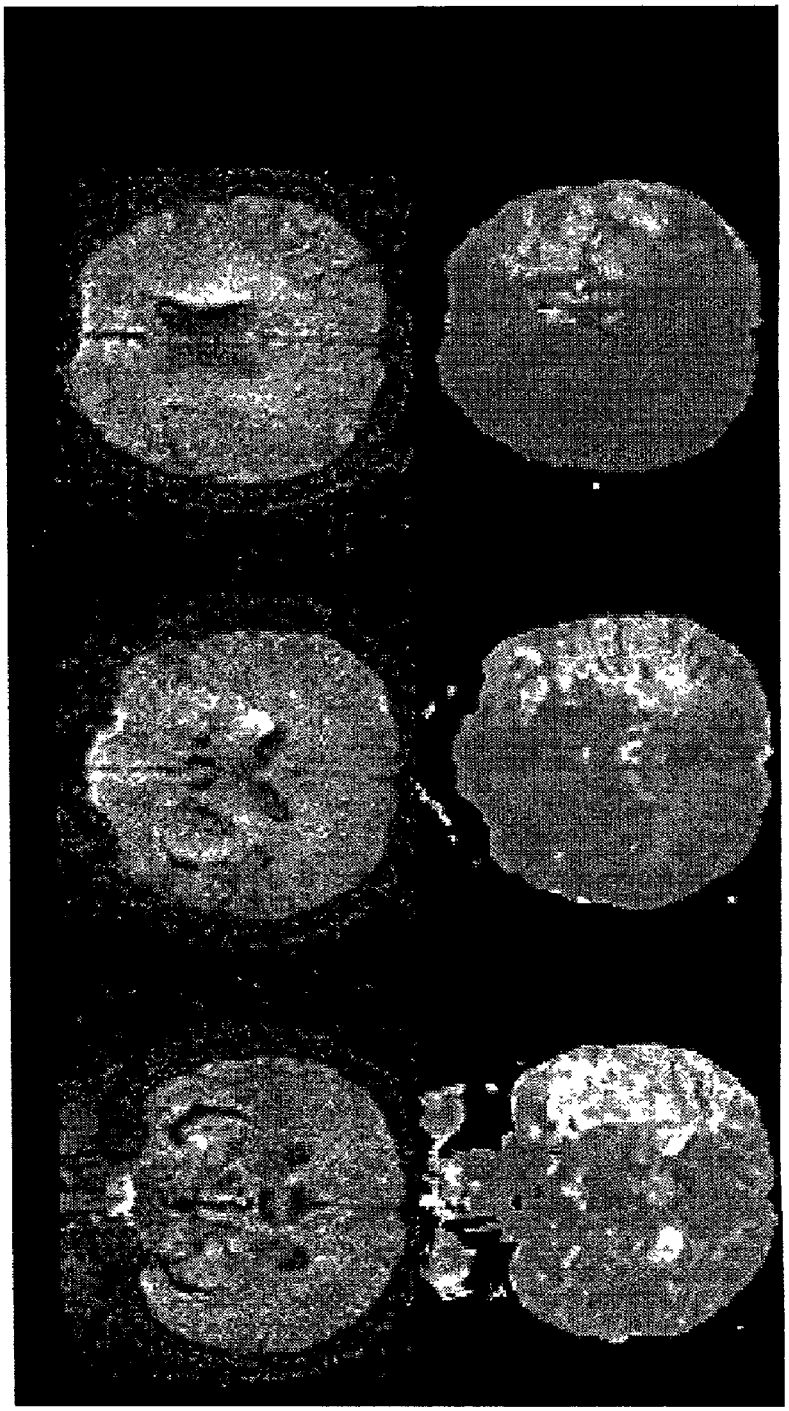
FIGS. 23a and 23b show the respective maps from patient 3.
Figure 23B:
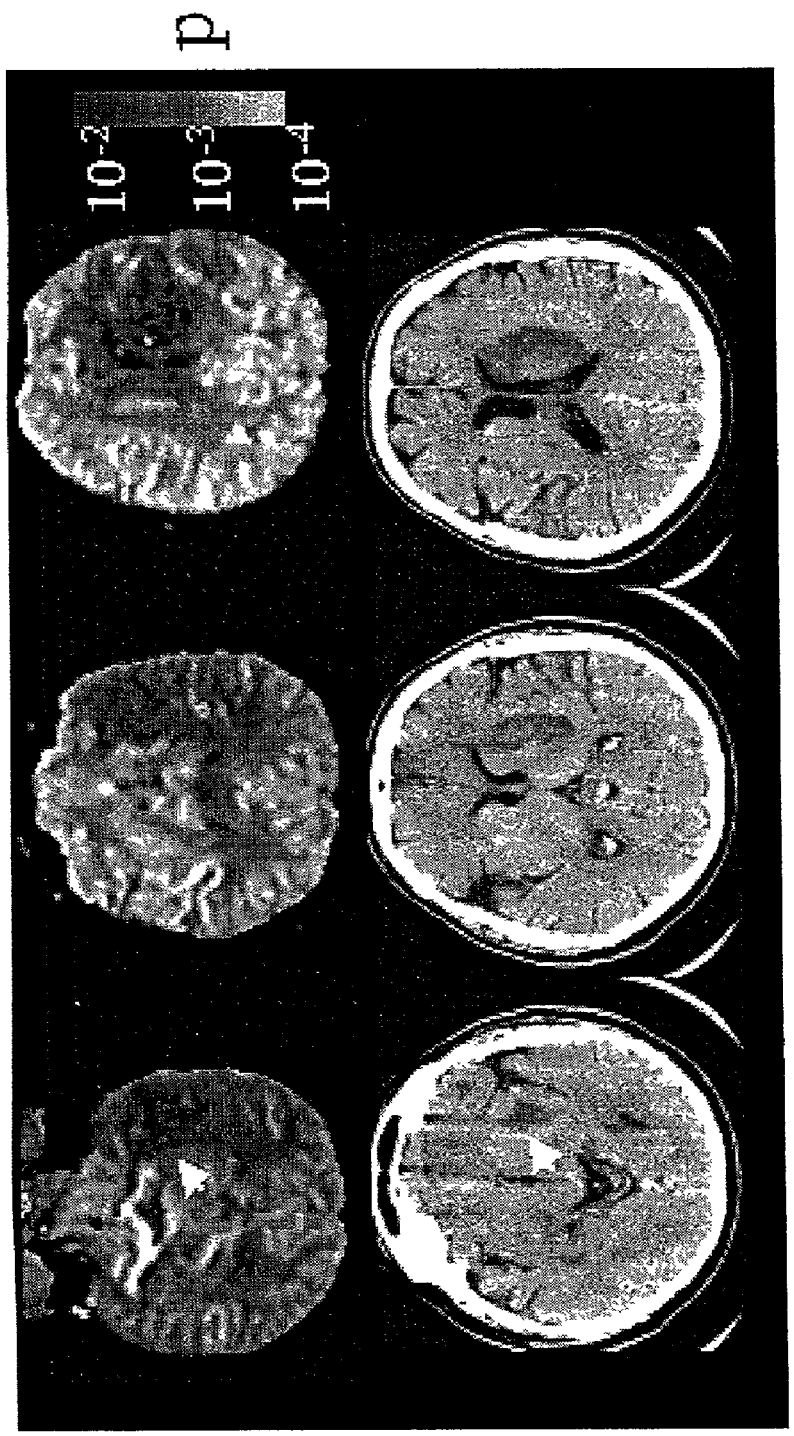

In 8 out of 11 patients, comparison of initial DWI images with the follow-up study showed that lesion size had increased in between the initial and follow-up scans. In all 8 cases, neuronal death had occurred within the region initially displaying increased MTT. FIGS. 21a and 21b show this correlation in patient 11, a 45-year-old male 6.5 hours after onset of symptoms. On the initial DWI (first row), cell death is localised to deep gray matter, whereas the acute MTT maps (second row) show prolonged MTT corresponding to the whole middle cerebral artery territory. The p-map shows highly significant deviations from the normal flow PDF in anterior and posterior sub-regions. These subregions corresponded well with tissue that later infarcted, displayed as bright regions in the 2-month follow-up FLAIR MRI images (bottom row). In FIG. 22, final infarct volumes are compared to the initial abnormalities of DWI+MTT and DWI+p maps, respectively. Notice the striking ability of combined initial DWI and p-maps to predict final infarct size. In 10 out of 11 patients, p maps (excluding vessels and volumes with preserved, high flow component, see below) corresponded well with the final infarct. FIGS. 23a and 23b show the respective maps from patient 3. Notice that the initial lesion (top row) and extent of MTT prolongation (second row) are similar to that observed in FIGS. 21a and 21b. Although the CBF was significantly decreased (Third row, gray scale image), there were only small abnormalities in the flow heterogeneities (indicated by coloured areas on overlay on the CBF map). The small spots correspond to vessels, having a high degree of flow heterogeneity. The final infarct size was similar to that observed on the initial DWI, indicating that the heterogeneity may again have served as a predictor of final outcome.

Figure 24A:
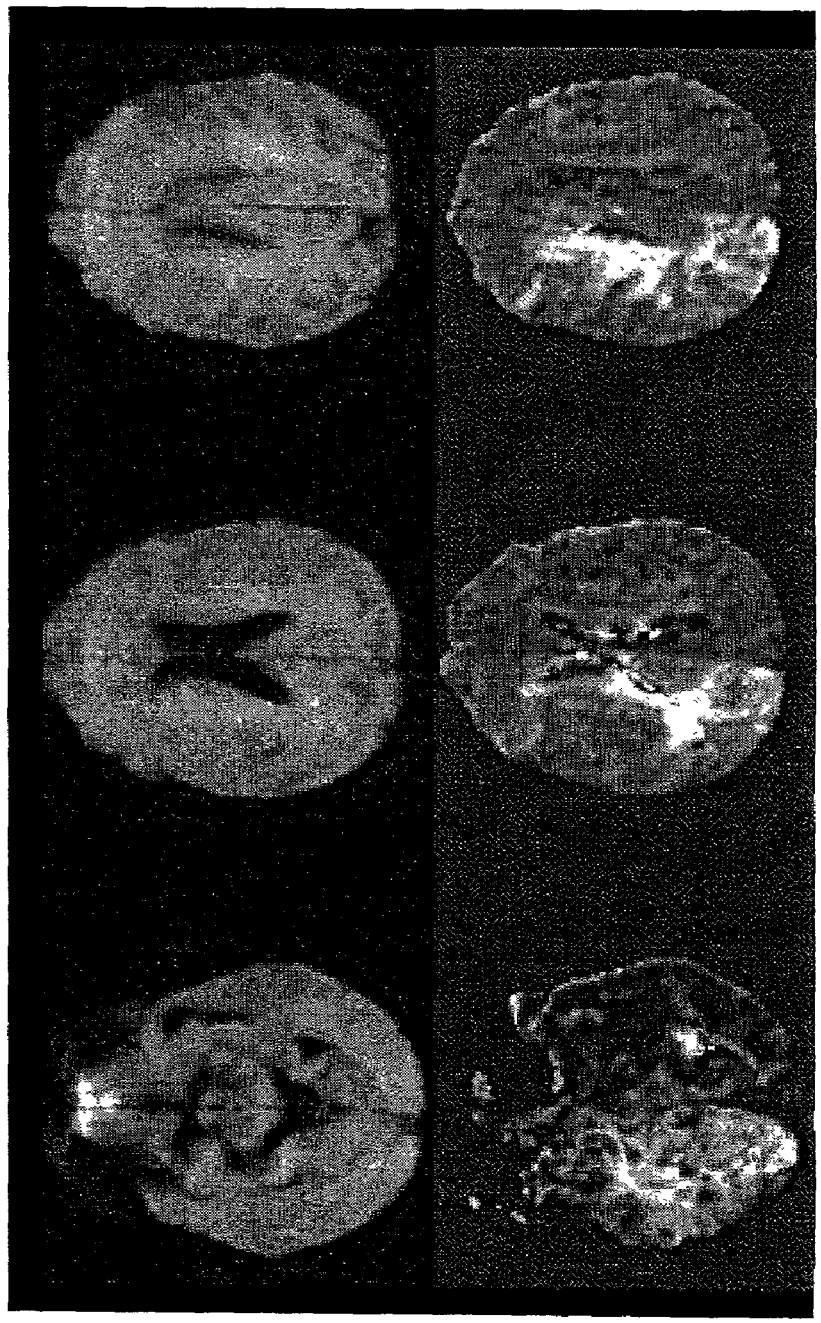
FIGS. 24a and 24b show maps from patient 9.
Figure 24B:
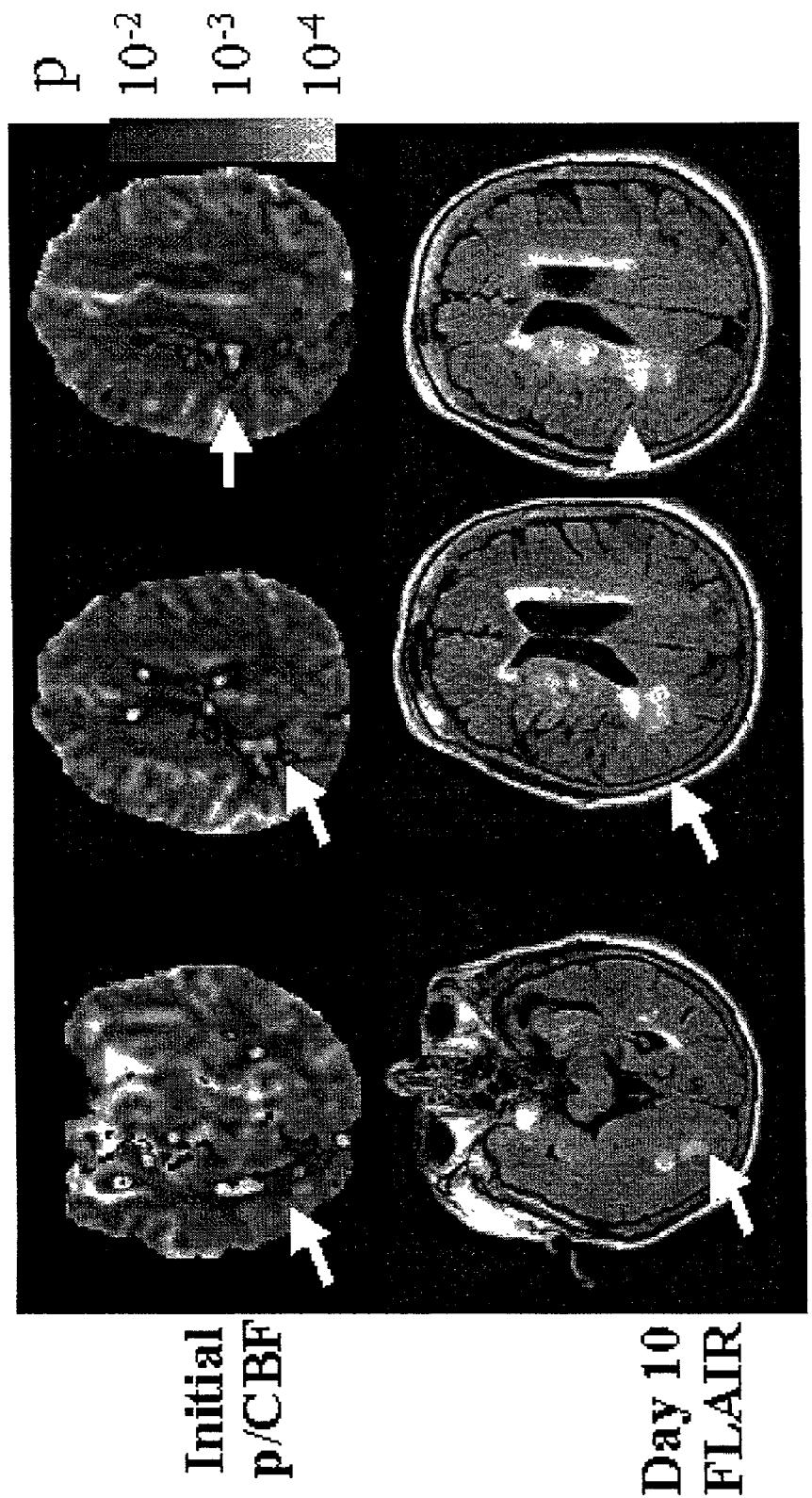

To demonstrate the predictive value of the p-maps in cases of white matter ischemia, FIGS. 24a and 24b show maps from patient 9, a 80 year old female. Small infarcted areas are seen on the initial DWI images (Top row). The MTT image shows abnormalities extending into white matter around the initial lesions. Again, flow heterogeneity changes are observed in smaller subregions, corresponding well to the regions that went on to infarction. Notice symmetrically located areas with low p values, corresponding to vessels.

Artifacts in p-Maps

Figure 25:
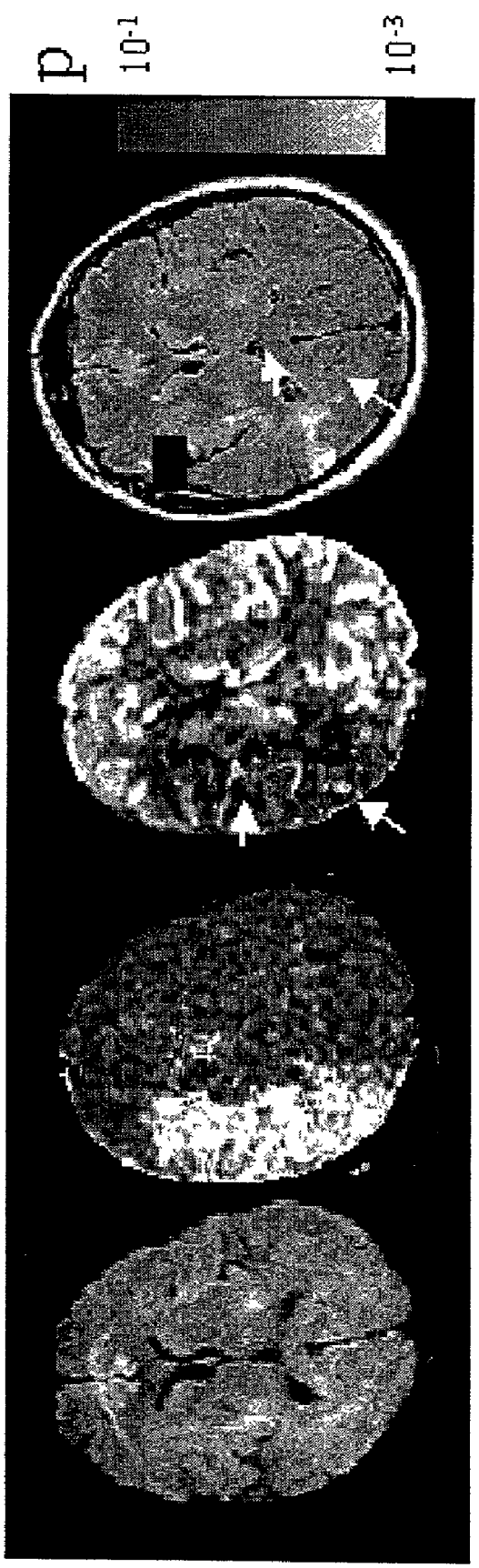
FIG. 25 shown one slice from this patient, displaying areas with p<0.1.

In one case, (patient 9), p maps underestimated the final infarct size. FIG. 25 shows one slice from this patient, displaying areas with $p<0.1$. Notice high-intensity areas correspond to areas that later infarcted, whereas a number of areas showed unspecific p increase. Separate evaluation of areas with $p<0.01$ would in this patient cause underestimation of final infarct size. Interestingly, follow-up MR angiography in this patient demonstrated spontaneous reperfusion between initial and follow-up scans. In the p-maps, small areas of low p-values were in some cases observed at the location of major vessels (See FIGS. 21b and 24b), due to the homogenous flow pattern in vessels relative to that in tissue. These areas were not included when defining areas of abnormal tissue flow heterogeneity for comparison with follow-up studies. In patients 3 and 4, areas unrelated to major vessels showed low p-values in a single slice, whereas adjacent tissue in neighbouring slices showed no abnormalities. Analysis of the flow heterogeneity PDF in these single slices revealed a high-flow distribution similar to that of normal tissue, whereas the low-flow component showed flow components down to zero (unlike the relatively sharp cut-off at 0.5 observed in normal tissue—See FIG. 20b). This is interpreted as being due to dispersion of the AIF relative to the tissue. Based on the preserved high-flow component and the normal PDF observed in adjacent tissue in neighbouring slices, these areas were not included when comparing p-maps with follow-up images. Below these phenomena are further discussed.

Discussion

The study confirms the report by Hudetz et al in animals that decreased perfusion pressure (CBF:CBV ratio) is associated with progressive loss of high-flow components (Hudetz 1996). The study extends these findings by documenting loss of flow heterogeneity in human acute stroke, and good agreement between heterogeneity changes in early ischemia and eventual tissue infarction. The findings presented hence strongly support the hypothesis by Hudetz et al that gradual loss of the high flow component of the flow heterogeneity PDF heralds local loss of functional reserve capacity, and thereby neuronal death (Hudetz 1996). The finding that p-maps predict final infarct size with high certainty in untreated patients suggest that MR heterogeneity measurements may prove useful for individual planning of patient management, as well as for evaluation of new therapeutic approaches in smaller patient populations.

Figure 26:
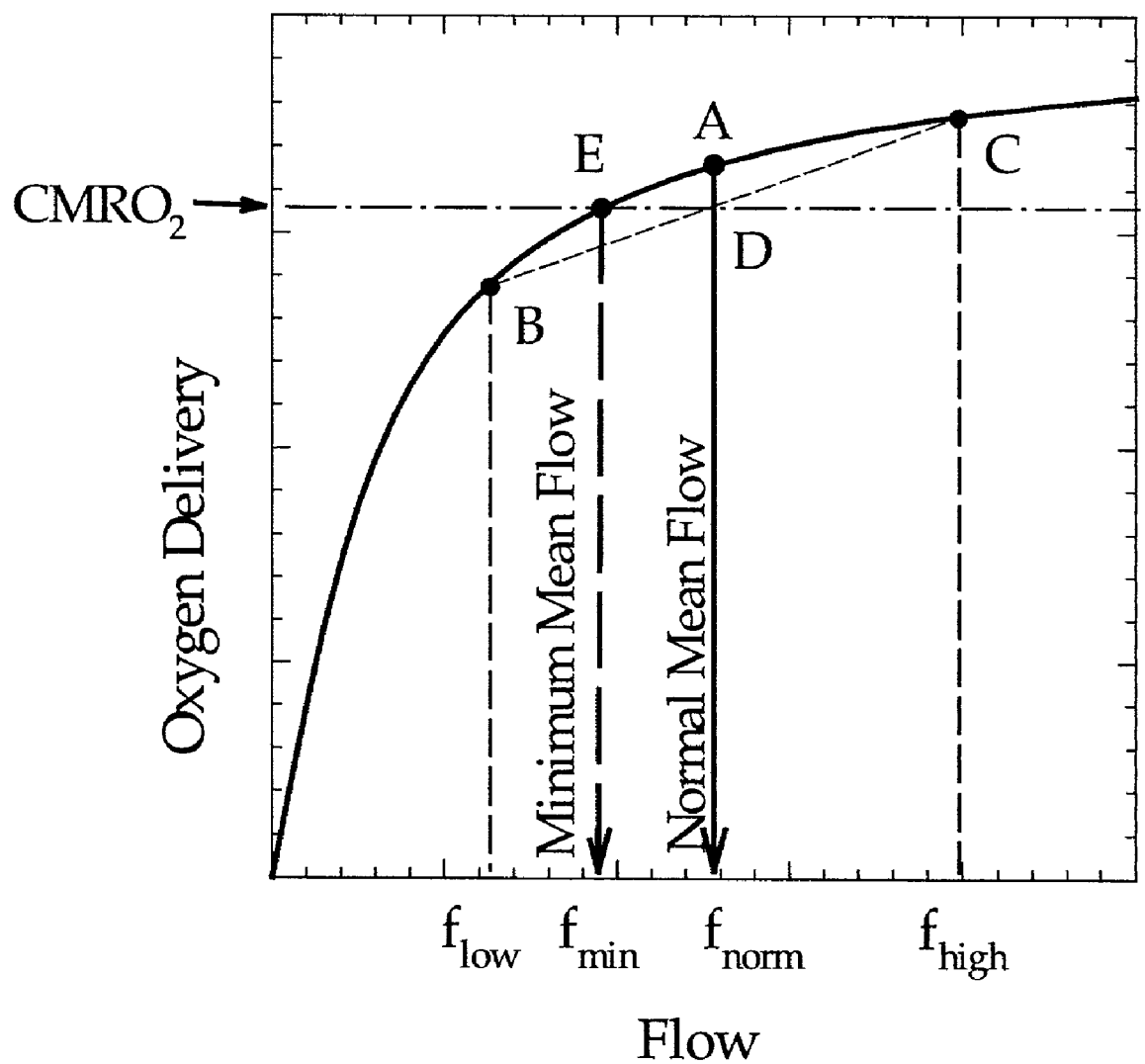
FIG. 26 shows the qualitative analysis of the kinetics of oxygen delivery.

The hypothesis of heterogeneity changes being the driving force in regulating oxygen delivery to tissue (Kuschinsky and Paulson 1992; Vogel and Kuschinsky 1996) suggest a close relationship between the findings presented here and the OEF increase observed by PET in tissue at high risk of subsequent infarction (Powers 1991; Wise 1983). Indeed, qualitative analysis of the kinetics of oxygen delivery show that one should expect reduced heterogeneity of blood flow to produce an increased flow of oxygen into the tissue in states of decreased flow, as illustrated in FIG. 26. The curve is a plot of the oxygen flow into tissue versus blood flow. From the convex shape of the curve it can be seen that oxygen flow into the tissue at a given mean blood flow is greater when blood flow is homogenous than when blood flow is more heterogeneous: Oxygen flow into tissue versus blood flow $F_t$, related through the equation $F_t \cdot (1-e^{-PS/F_t})$, where PS is the permeability to oxygen times the surface area of capillaries (Renkin 1959; Crone 1963). If all blood flow is at the normal mean flow, $f_{norm}$, the oxygen flow into tissue is given by the height of A. If part of the flow is at $f_{low}$ and the rest at $f_{high}$, with weightings to maintain the same mean flow, the oxygen flow into the tissue will be the height of D. Notice, as mean flow is reduced and $f_{high}$ and $f_{low}$ changed to maintain the same $CMRO_2$, both $f_{low}$ and $f_{high}$ approach $f_{min}$, thereby decreasing the degree of heterogeneity. Notice decreased flow heterogeneity with constant flow will increase oxygen delivery, in parallel with the findings of Vogel et al, who found decreased heterogeneity in states of functional activation and thereby increased oxygen metabolism (Vogel and Kuschinsky 1996).

The observed shifts toward a homogenous flow distribution may therefore signal increased utilisation of metabolic regulatory capacity, explaining the risk of neuronal death observed in these regions of extreme flow homogenisation. PET is today the method of choice to demonstrate metabolic reserve capacity in cerebrovascular disease. However, future studies should focus on the relationship between MR flow heterogeneity measurements and OEF measured by PET to further explore this coupling of microvascular dynamics and metabolism.

Neuronal death was localised in areas initially displaying prolonged plasma mean-transit times. This is agreement with the previous experience using this technique (Sorensen 1998), as well as studies using PET (Heiss 1994; Baron 1981) and single photon emission computed tomography (SPECT) (Buell 1988). Although the CBV:CBF ratio (i.e. 1/MTT) depends linearity on the cerebral perfusion pressure over a range of values (Schumann 1998), this dependence is likely to be lost when maximum vasodilation is reached at low pressures (Powers 1991). The MTT prolongation may therefore not be directly related to the severity of the perfusion pressure drop and hence risk of infarction. The findings support, however, that prolonged MTT is an early sign of decreased perfusion pressure, at a stage where regulatory mechanisms may still suffice to ensure tissue survival.

Although the high flow component seem crucial to tissue survival, the low flow component of the flow heterogeneity PDF may also prove useful in planning therapeutic approaches. Intravital microscopy studies suggest that maintaining capillary flow velocities above a fixed, lower limit is essential to avoid white blood cell plugging of capillaries (Hudetz 1996; Yamakawa 1987). The distributions of absolute flows in single pixels may prove useful in assessing of leukocyte adhesion prior to therapeutic attempts to reperfuse tissue.

In patients with cerebrovascular disease, the AIF may undergo dispersion and delays upstream of site of measurement, possibly causing overestimation of MTT (Østergaard 1996a; Østergaard 1996b). This bias was reduced by choosing AIFs in the vascular territory affected by the vascular occlusion. Furthermore, dispersion of the AIF will tend to broaden the flow PDF. Therefore, the effects of dispersion counteract the observed homogenisation of flow elements.

In determining the flow PDF, high p values were observed near vessels (and therefore easily identifiable on the accompanying CBV maps), as major vessel flow inherently homogenous. Probability maps should therefore be carefully inspected for vessels on CBV maps, as well as signs of vessel dispersion in the PDF shape in a given region. SE-EPI images are particularly suited for this type of analysis, as large vessels are suppressed due to the inherent microvascular weighting of these images (Fisel 1991; Boxerman 1995; Weisskoff 1994).

Given these precautions, the findings presented here indicate that magnetic resonance based assessment of flow heterogeneity provides a powerful tool to study residual metabolic reserve capacity in peri-infarct tissue. Combined conventional MRI, MR angiography, DWI, determination of flow heterogeneity and plasma mean transit time can be performed in roughly 20 minutes on most clinical MR systems. Unlike PET and SPECT, examinations can therefore be performed within the short time-window where treatment should be initiated in order to prevent the progression of neuronal death. Presence of tissue with loss of flow heterogeneity may in the future serve to guide individual patient management, and point to tissue that may serve as target for novel therapeutic approaches

EXAMPLE 5

Renal Plasma Flow, Volume and Transit Time Heterogeneity Measured By Magnetic Resonance Imaging Introduction Noninvasive methods for assessing individual renal function are essential in diagnosis of disease as well as in subsequent monitoring of disease progression, especially the deterioration of renal function in renal artery stenosis, diabetes, ureteral obstruction, neurogenic bladder, and to identify rejection or other postoperative complications in renal transplants. The questions often asked is whether function is stable or deteriorating, thereby detecting changes at early stages where treatment may still be possible, or in some cases in unilateral disease to determine whether the patient may benefit from nephrectomy.

Existing Techniques for Assessing Renal Function

Unilateral renal function is today almost exclusively determined by radionucleide measurements, using mostly $^{99m}$Tc, $^{51}$Cr or $^{131}$I/$^{123}$I bound agents and gamma camera detection. The radiotracers fall into three main groups, filtered agents that are exclusively filtered in the glomeruli, secreted agents that are totally removed from the blood into the urine during a single transit, and finally the more rare bound agents which display some degree of binding to the renal parenchyma.

Filtered agents (mainly $^{99m}$Tc-DTPA) are filtered in the glomeruli and thereby give a direct measurement of glomerular filtration rate (GFR). As only a fraction of the total plasma flow to the kidney is filtered (roughly 20%), use of these agents give no direct information on renal blood flow.

Secreted agents (e.g. $^{99m}$Tc-MAG$_3$, $^{123}$I/$^{131}$I-OIH) are almost totally removed (~90%) from the blood during a single transit, and the rate at which it disappears from the blood and appears in the urine is therefore proportional to renal plasma flow (RPF).

Bound agents (e.g. $^{99m}$Tc-DMSA, $^{99m}$Tc-GHA) often show some extent of plasma binding as well as secretion into the urine. Ideally, however, these agents would show regional uptake in the parenchyma proportional to tissue flow.

Functional Parameters

The functional indices derivable from dynamic images acquired after injection of these agents are closely related to the characteristic transport and uptake over time. The early phase (~1 minute) after the injection of either filtered or secreted agent mainly display the initial, vascular distribution of the tracer and is referred to as the vascular transit segment. This phase is to some extent related to renal blood flow, as a rapid transit presumably signal high blood flow.

The nephron transit segment (~1–5 minutes, i.e. uptake/transport through the nepron) reflects GFR for a filtrated agent and RPF for a secreted agent.

The body transit segment (10–30 minutes) detects either clearance of tracer from the whole body or the appearance of tracer in the bladder. Again, by the properties of the tracer, the rate of clearance reflects RPF for secreted agents and GFR for filtered agents The role of macroscopic and microscopic haemodynamic changes in disease Evidence suggests that along with the gradual deterioration of renal parenchyma in acute and chronic renal disease, marked changes in overall renal perfusion as well as renal microcirculation occur. These latter changes range from abnormal tone in afferent arterioles (e.g. hypertension (Iversen 1998) and acute renal failure (Bock 1997)) leading to abnormal pressure gradients and possibly loss of autoregulation (Iversen 1998), changes in the width and shape of glomerular capillaries in early stages of glomerular sclerosis (Nagata 1992) and finally extreme heterogeneity of transit time in the peritubular capillaries in experimental uremia (Shea 1984).

These states of abnormal pressure or vascular structure all lead to changes in plasma transit time characteristics (pressure gradients change transit time as this is roughly the inverse of the perfusion pressure) at a regional, glomerular or even post-glomerular capillary (Shea 1984) level. Although regional flood flow and transit time dynamics may be important in early detection of pathological changes in renal disease, the ability to characterize microscopic changes in transit time distributions may therefore enhance the ability to detect early changes in disease development.

Possible Future Role of Magnetic Resonance Imaging (MRI)

Contrast enhanced MR imaging using Gd-chelates such as Gd-DTPA provide a complete analogue to $^{99m}$Tc-DTPA renography for GFR measurements, but offering superior spatial resolution and the advantage of being free of exposure to ionizing radiation. With the development of purely intravascular contrast agent, and techniques to assess plasma flow and plasma volume from residue detection techniques (Østergaard 1996), these GFR measurements can be supplemented by high resolution haemodynamic information. Furthermore, novel developments in characterizing microscopic flow- and transit time heterogeneity (Østergaard 1999, Ex 1) may allow addressing the regional microscopic haemodynamics, thereby possibly improving diagnostic power of non-invasive tomographic techniques.

Aim of this Study

In this report, we used a recently developed method to determine regional plasma flow in the kidney after acute obstruction of one ureter. Furthermore, we applied a novel method to assess transit time distribution in single pixels, in order to demonstrate the feasibility of monitoring transit time characteristics on pixel-by-pixel level in the kidney.

Materials and Methods

Animal Preparation and Experimental Protocol

Country-bred Yorkshire pigs weighing 30 kg were used in the experiments Pigs were initially sedated by i.m. injection of 0.25 ml/kg of a mixture of midazolam (2.5 mg/ml) and ketamine HCl (25 mg/ml). A catheter was then placed in an ear vein. After i.v. injection of additional midazolam/ketamine mixture (0.25 ml/kg), the pig was intubated and artificially ventilated throughout the experiment, maintaining anesthesia by continuous infusion of 0.5 ml/kg/hr of the midazolam/ketamine mixture and 0.1 mg/kg/hr pancuronium. Indwelling femoral arterial and venous catheters were surgically installed. Unilateral ureteral obstruction (UO) was induced by ligation of one ureter through a low midline incision.

MRI Protocol

Images were acquired on Gyroscan NT 1.5 Tesla whole-body system (Philips Medical Systems, The Netherlands) running the NT5 3. software version at Uppsala University Hospital, Sweden.

Dynamic images were acqired using a Fast Field Echo (FFE) with a repetition time (TR) of 11.3 ms, echo time (TE) 8.0 ms and a flip angle of 12° Dynamic images could hence be acquired once every 1.2 second. Image Field Of View (FOV) was 280 by 280 mm with a 256 by 256 resolution, leading to an in-plane resolution of 1.09 mm 1.09 mm at a 6 mm slice thickness. A series of 60 dynamic images were acquired during the rapid bolus injection of 1 mg Fe/kg of NC100150, an ultra small iron oxide particle (USPIO) intravascular contrast agent (Nycomed-Amersham, Oslo, Norway).

Experimental data are courtesy of Lars Johannson and Atle Bjørnerud, Nycomed Imaging AS.

Renal Blood Flow and Transit Time Characteristics

We utilised the fact that the tissue impulse response to a plasma tracer can be estimated by non-parametric deconvolution of the tissue residue during the tracer passage by a non-invasively determined AIF. From this we derive the distribution of plasma transit times. The tissue concentration $C_t(t)$ of tracer in response to an arterial input function $C_a(t)$ is given by $$C_t(t) = F \cdot C_a(t) \otimes R(t) \equiv F \cdot \int_0^t C_a(\tau) R(t-\tau) d\tau \qquad \text{Eq. 24}$$

where F is tissue flow and R is the residue function, i.e. the fraction of tracer present in the vasculature at time t after a perfect, infinitely sharp input in the feeding vessel. Assuming the arterial and tissue concentrations are measured at equally spaced time-points $t_1, t_2, \ldots, t_N$, this equation can be discretised, assuming that over short time intervals $\Delta t$, the residue function and arterial input values are constant in time:

$$C_t(t_j) = F \cdot \int_0^{t_j} C_a(\tau) R(t-\tau) d\tau \approx \Delta t \cdot F \cdot \sum_{i=0}^{t} C_a(t_i) R(t_j - t_i) \qquad \text{Eq. 25}$$

or $$F_t \cdot \Delta t \cdot \begin{pmatrix} C_a(t_1) & 0 & \ldots & 0 \\ C_a(t_2) & C_a(t_1) & \ldots & 0 \\ \ldots & \ldots & \ldots & \ldots \\ C_a(t_N) & C_a(t_{N-1}) & \ldots & C_a(t_1) \end{pmatrix} \begin{pmatrix} R(t_1) \\ R(t_2) \\ \ldots \\ R(t_N) \end{pmatrix} = \begin{pmatrix} C_{br}(t_1) \\ C_{br}(t_2) \\ \ldots \\ C_{br}(t_N) \end{pmatrix} \quad \text{Eq. 26}$$

As previously described (Østergaard 1996), this equation can be modified to residue and arterial input functions varying linearly in time, and solved by Singular Value Decomposition (SVD) to yield the residue function. The distribution of transit times, h(t), is then found from $$R(t) \equiv \left[ 1 - \int_0^t h(\tau) d\tau \right] \Rightarrow h(t) = -\frac{dR}{dt} \quad \text{Eq. 27}$$

i.e. the slope of the residue function. We therefore determined h(t) at a given time point $t_1$ as $$h(t_i) = \quad \text{Eq. 28}$$
$$\frac{1}{2} \cdot \left( \left( \frac{R(t_i) - R(t_{i-1})}{\Delta t} \right) + \left( \frac{R(t_{i+1}) - R(t_i)}{\Delta t} \right) \right) = \frac{1}{2} \cdot \left( \frac{R(t_{i+1}) - R(t_{i-1})}{\Delta t} \right)$$

In order to make measured transport functions comparable, they were normalised to the mean transit time by requiring $$\int_0^\infty \tau \cdot h(\tau) d\tau = \int_0^\infty h(\tau) d\tau = 1 \quad \text{Eq. 29}$$

Tissue and Arterial Concentration Estimates

Tissue concentrations were estimated assuming the concentration at time t, $C_t(t)$, is proportional to the change in transverse relaxation rate, i.e.

$$C_t(t) = -k \cdot \log\left( \frac{S(t)}{S(t_0)} \right) / TE \quad \text{Eq. 30}$$

where $S(t_0)$ is the baseline signal intesity, S(t) the signal intensity at time t and TE the echo time (k is here a constant depending on the contrast agent and the blood characteristics). Arterial concentrations were obtained in a similar manner, from pixels located at the renal artery in the hilus region.

Results

Figure 27:
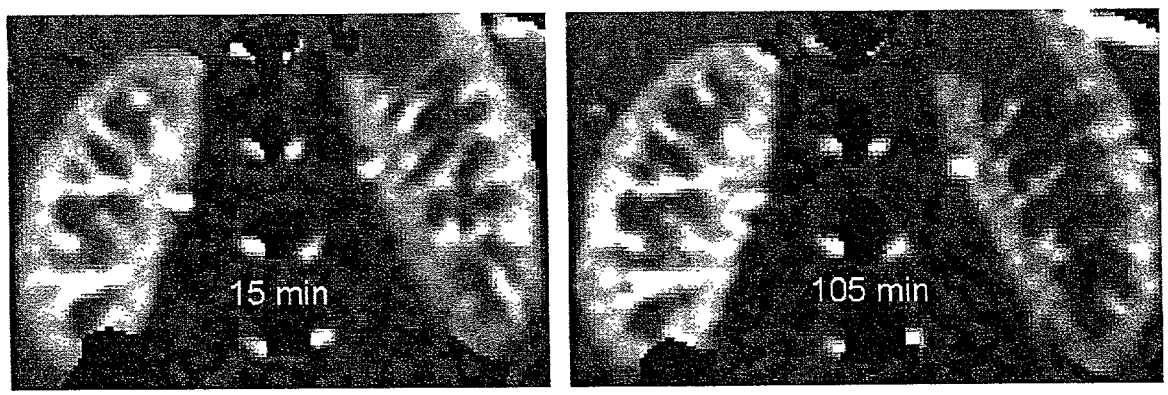
FIG. 27 shows typical parametric renal flow images acquired immediately after and 105 minutes after ureteral occlusion.
Figure 28:
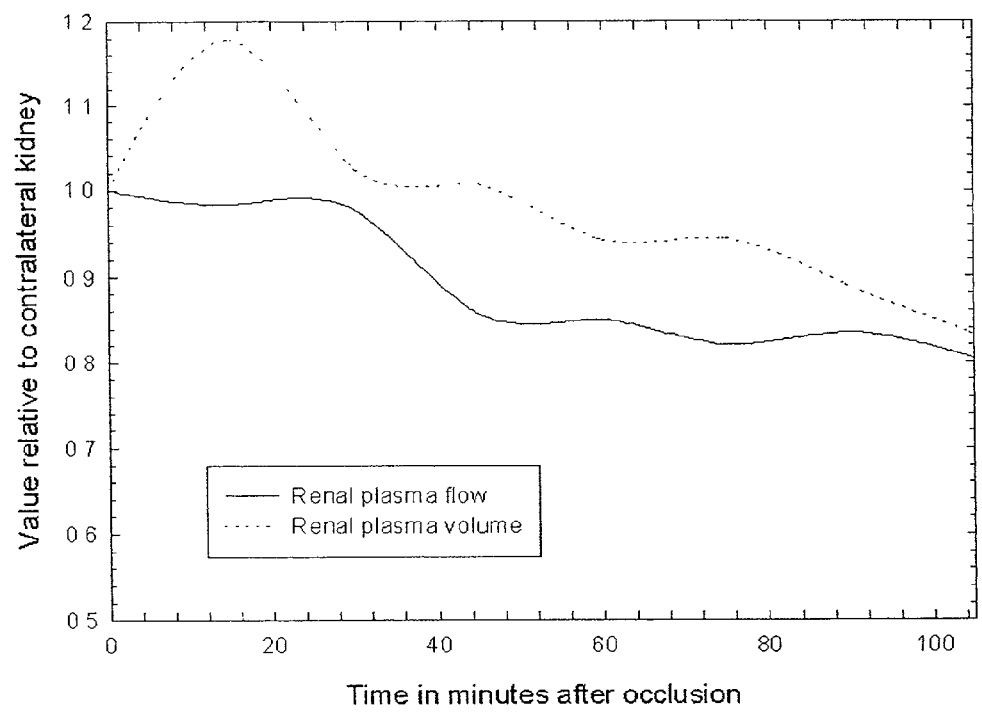
FIG. 28 shows the temporal evolution of renal plasma flow and volume after ureteral occlusion.

FIG. 27 shows typical parametric renal flow images acquired, immediately after and 105 minutes after ureteral occlusion. Note the high spatial resolution (1.09 by 1.09 mm) compared to the roughly 10 by 10 mm resolution of most radionucleide scans. Also note high contrast over surrounding muscle tissue displaying much lower plasma flow. Generally, little problems due to motion during the dynamic imaging session was experienced. In FIG. 27 is shown images showing high resolution images of relative renal plasma flow 15 minutes after (left) and 105 minutes after (right) obstruction of the left ureter (located at right hand side in the images). Notice the dilation of the left kidney and marked reduction in flow after obstruction FIG. 28 shows the temporal evolution of renal plasma flow and volume after ureteral occlusion. Notice the gradual and parallel decrease in both quantities after occlusion, reaching 20% after 100 minutes. The plasma volume displays a short increase immediately after occlusion, seemingly keeping plasma flow at constant values. In FIG. 28 is shown temporal evolution of renal plasma flow and volume after ureteral occlusion. Whole kidney parenchyma was manually segmented by an image analysis program (Cheshire, Hayden, Boulder, Colo.). For the normal kidney, a similar Region Of Interest could be used for all time points, but for the occluded side, ROI's had to be adjusted to take dilation into account. The occluded kidney values were then normalized to the contralateral side. Notice the gradual and parallel decrease in both quantities after occlusion, reaching 20% after 100 minutes. The plasma volume displays a short increase immediately after occlusion, seemingly keeping plasma flow at constant values.

Figure 29:
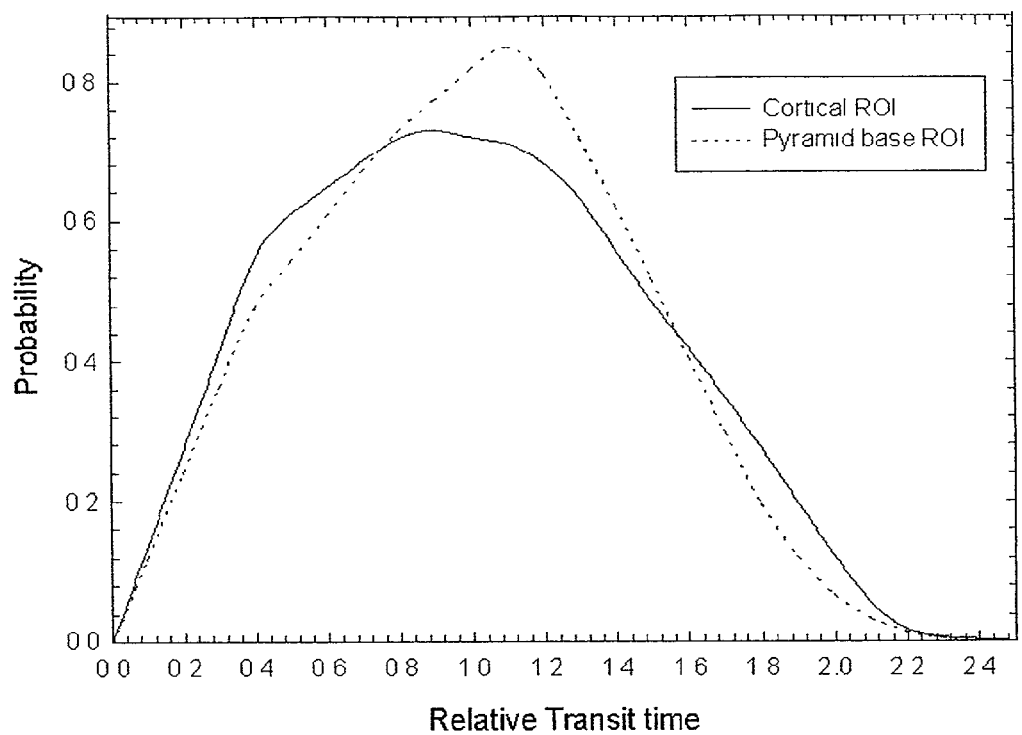
FIG. 29 shows transit time characteristics measured as the averaged transport functions in 4 pixels from to regions.

FIG. 29 shows transit time characteristics measured as the averaged transport functions in 4 pixels from to regions. In most of the renal parenchyma, normalized transport functions were of similar shape. Only the tissue at the base of the pyramids showed a slightly more homogenous transit time distribution. Transit times were of the order of 1 second, and relatively uniform across the kidneys. No differences between kidneys were observed in the transit time distributions in ureteral obstruction. In FIG. 29 is shown distribution of transit times relative to the mean transit time. The shape of the distribution was very homogenous across the paranchyma (full line): One exception was noticed in the pyramids (Dashed line) with a slightly more homogenous distribution of transit times. We speculate this may be due to a fraction of the vessels being vasa recta in this ROI. These ROIs may display a more homogenous flow distribution due to the difference in capillary organization in pyramids relative to cortical areas.

Discussion

Our results showed marked, acute decrease in RPF and RPV immediately after obstrution of the ureter. The plasma flow reduction was 20% within the first hour after occlusion. The change is somewhat smaller than the 35% decrease observed by Frøkjær et al. (1996) by electromagnetic flow probes directly in the renal artery, and 33% by Claudon et al. using Doppler ultrasound (Claudon). This difference may owe to methodological differences between arterial flow velocity measurements and tomographic, tissue level flow measurements. The parallel reduction in RPV indicates that the obstruction is associated with a vasoconstriction, in agreement with previous findings (Frøkjær 1996). Our findings suggest a transient increase in blood transit time after obstruction (the volume:flow ratio and thereby the transit time increase is seen in FIG. 28), indicating decreased perfusion pressure (The inverse of the transit time). Perfusion pressure was normalized, however, after roughly 30 minutes.

The distribution of transit times could be recorded on a pixel-by-pixel basis, suggesting that microvascular haemodynamic changes can indeed be studied, thereby characterizing microscopic changes in disease. As mentioned in the introduction, transit time are closely associated with the changes in nepron vascular ultrastructur, and high resolution transit time characteristics may therefore at some point aid in the early detection of disease. No asymmetries in transit time distributions were detected in this acute occlusion study, in agreement with the fact that microcirculation is believed to remain intact in acute phases of acute occlusion.

The use of MRI offers the advantage of high resolution images of not only blood flow and volume, but also the possibility of high resolution structural MR images, magnetic resonance angiography and—with the addition of a small Gd-chelate contrast agent—high resolution GFR images. Imaging can be performed without subjecting the patient to ionizing radiation, and with only limited time consumption beyond a traditional radionucleide renography.

We observed tissue mean transit times of the order of 1 second in this study, suggesting high image sampling rate is essential, just the arterial input reaching the tissue must be very sharp to accurately define tissue transit time characteristics. It is believed, however, that this will be within reach in a clinical setting with current methods and technology. Also, we believe that water relaxation characteristics in the kidneys may need further study with the contrast agent used. Fist, $T_1$ relaxation effects may become important, just as we speculate that the 80% reduction in glomerular filtration rate (GFR) also observed in acute obstruction (Hvistendahl 1996) may disturb normal water exchange between capillaries and tubuli, thereby affecting measurements slightly.

EXAMPLE 6

Flow Heterogeneity of Cerebral Neoplasms—a Measurement of Microvascular Tortuosity?

Tumor growth is limited by the neoplasms ability to stimulate surrounding tissue to form new vessels. Tumour angiogenesis by release of humoral factors (Vacular endothelial growth factor—VEGF) is thereby one of the hallmarks of tumour growth, and also constitutes the target of novel approaches to treat human neoplasms. Methods to non-invasively assess the size, density and integrity of tumour microvessels are therefore essential to detect malignancies, understand tumour growth, and to target and monitor new therapeutic approaches (Ferrara and Alitalo, 1999).

Dynamic susceptibility contrast imaging, measuring cerebral blood volume (CBV), has for some time been used to characterise cerebral haemodynamics (Rosen et al., 1990; Rosen et al., 1991a; Rosen et al., 1991b). Together with the specific sensitivity of spin echo (SE) Echo Planar Imaging (EPI) (Weisskoff et al., 1994; Boxerman et al., 1995) to microvessels, this approach provides a unique potential to study the proliferation of capillary sized vessels in tumour angiogenesis. As the ability to form new vessels is closely related to the growth potential and thereby aggressiveness of the tumour, the relation between histological tumour grade and regional CBV has been studied extensively. Aronen et al. studied 19 cerebral glioma patients, demonstrating that CBV correlated with tumour grade as determined by biopsy or surgery (Aronen et al., 1994). Also, a positive correlation was found between CBV and microscopic vascularity as well as mitotic activity.

While the increase in microvascular blood volume reflects vessel formation indirectly, characterising the complex tortuous microvascular structure in newly formed tumour vessels may be important in quantifying the angiogenic process. More importantly, characterising the haemodynamics of the tumour microvasculature may be essential in understanding the retention of drugs in these tumours, and thereby optimising drug targeting.

The aim of this study was to examine the feasibility of demonstrating abnormal haemodynamics in cerebral tumours showing angiogenic activity, defined as increased microvascular CBV as determined by SE dynamic susceptibility contrast imaging)

Materials and Methods

Data were acquired as part of a study designed to examine the effects of dexamethasone (Østergaard et al., 1999b) in brain tumour patients. The subjects were consecutive patients seen in the Massachusetts General Hospital neuro-oncology clinic with brain tumours or brain tumour recurrence.

Dynamic Imaging for CBV and CBF Measurements.

Images were obtained using a GE Signa 1.5 Tesla imager retrofitted for EPI capabilities (Instascan, Advanced NMR Systems, Wilmington, Mass.). All subjects received 0.2 mmol/kg of a Gd-based contrast agent (Gd-DTPA, Magnevist, Berlex) delivered by a prototype MR-compatible power-injector (Medrad Inc., Pittsburg, Pa.) at a rate of 5 ml/sec in an antecubital vein. EPI was performed using TR=1.5 sec, TE=75 msec. Images were acquired in a 256 by 128 imaging matrix with a 40 by 20 cm field of view, resulting in 1.6 by 1.6 mm pixels with a slice thickness of 6 mm and an inter-slice gap of 1 mm. Ten slices were obtained simultaneously to cover the whole tumour region.

Haemodynamic Variables

Cerebral blood flow (CBF), CBV and flow heterogeneity was determined on a pixel by pixel basis as previously described (Østergaard et al., 1999a; Østergaard et al., 2000). In each image pixel, the distribution of flows (relative flow probability density function) was compared to that of normal brain by a Kolmogorov Smirnov test to identify areas of abnormal flow distributions (Østergaard et al., 2000)

Results

Figure 30:
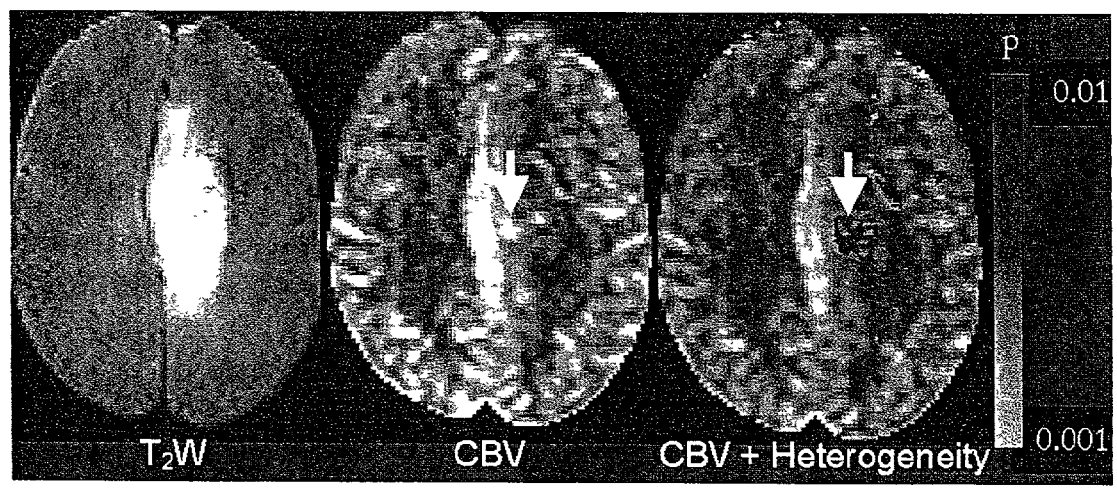
FIG. 30 shows structural $T_2$-weighted image (left) of a female with a grade II astrocytoma, showing edema in the medial part of the left parietal lobe.

FIG. 30 shows structural $T_2$-weighted image (left) of a female with a grade II astrocytoma, showing edema in the medial part of the left parietal lobe. The image of relative CBV (middle) shows areas of high CBV (arrow) in the centre of the tumour process, indicating angiogenic activity. The image at the right shows areas of abnormal distribution of flows compared with normal brain tissue (Østergaard et al., 1999a) as coloured areas overlayed onto the CBV map. Notice that within the tumour process, areas showing highly heterogeneous flow distributions are found, likely due to the increased tortuosity of the newly formed vessels.

Discussion

Our results indicate that in areas of increased microvascular density, areas of altered flow heterogeneity can be detected, possibly due to changes in the tortuosity of the microvasculature. This may provide a mean for further characterising the angiogenesis in tumours. The tortuosity of microvessels may be important in the pharmaceutical manipulation of the tumours: For optimal local drug effect, 'trapping' of molecules toxic to the tumour vessels in the tortuous vasculature may improve drug action by increasing the time drugs are in contact with the vascular endothelium (Endrich et al 1998). The microscopic haemodynamic information brought by flow heterogeneity measurements may therefore be important in understanding angiogenesis and optimising drug action in individual patients.

The current measurements were performed with Gd-chelates and only provide flow heterogeneity measurements in tissue where the contrast agent remains intravascular. Therefore, vascular haemodynamic changes were not detected in high grade tumours with leaky blood brain barrier, as signal changes due to the $T_1$ effects of extravascular contrast agent overwhelms the $T_2$ change due to intravascular contrast agent. With the development of blood pool agents, remaining intravascular in many tissue types, this technique may also be applicable to extraaxial tumours.

FIG. 30 shows structural $T_2$-weighted image (left) of a female with a grade II astrocytoma, showing edema in the medial part of the left parietal lobe. The image of relative CBV (middle) shows areas of high CBV (arrow) in the centre of the tumour process, indicating angiogenic activity. The image at the right shows areas of abnormal distribution of flows compared with normal brain tissue (Østergaard et al., 1999a) as coloured areas overlayed onto the CBV map Notice that within the tumour process, areas showing highly heterogeneous flow distributions are found, likely due to the increased tortuosity of the newly formed vessels.

The invention claimed is:

1. Method for determining haemodynamic indices of an organ or of a part of tissue of a mammal including
    a) determining a time series of tomographic data pertaining to the organ or part of tissue during and after a bolus injection of a tracer dose to said mammal, the tracer being substantially intravascular in said tissue,
    b) determining a time series of concentration data being indicative of the concentration of the tracer in arteries of the organ or tissue from the time series of tomographic data,
    c) determining a residue function of the organ or of the part of tissue by deconvolution of the time series of tomographic data with the time series of concentration data,
    d) determining a distribution of transit times from the negative slope of the residue function, and
    e) determining a probability density function (PDF) of a haemodynamic index from the distribution of transit times.

2. Method according to claim 1, wherein a probability density function (PDF) of a normalised haemodynamic index is determined from the distribution of transit times, the index being normalised by the value of the integral of said index.

3. Method according to claim 1, wherein at least one of the haemodynamic indices is a quantitative haemodynamic parameter obtained from the PDF.

4. Method according to claim 3, wherein at least one of the at least one parameter is obtain from comparison of the determined PDF and a previously determined reference PDF.

5. Method according to claim 4, wherein the parameter is obtained by use of the Kolmogorov Smirnov test.

6. Method according to claim 3 and comprising the steps of
    determining the impulse response function of the organ or of the part of tissue by deconvolution of the time series of tomographic data with the time series of concentration data,
    determining the relative tissue flow from the impulse response function of the organ or of the part of tissue,
    normalising said time series of concentration data with the integral of said time series of concentration data with respect to time,
    determining the normalised relative tissue flow, respectively the normalised blood volume, of the organ or part of tissue by use of the relative tissue flow and the time series of normalised concentration data, and
    converting said normalised relative tissue flow, respectively normalised blood volume, to an absolute value for the tissue flow ($F_t$), respectively the blood volume, by means of a previously determined conversion factor, the quantitative haemodynamic parameter being of metabolic significance and determined from the PDF and the absolute tissue flow ($F_t$), respectively the absolute blood volume.

7. Method according to claim 6, wherein a parameter (E) significant for the local extraction of a substance is determined, the method further comprising the following steps:
    calculating the relative flow heterogeneity (w(f)) as a function of the relative flow (f) from the distribution of transit times,
    estimating a value (P) for the local capillary permeability,
    estimating a value (S) for the local capillary surface area,
    calculating said parameter (E) as the integral value of the relative flow heterogeneity (w(f)) multiplied by one minus the natural exponential function of the negative ratio between
    i) the product of the local capillary permeability (P) and the local capillary surface area (S), and
    ii) the product of the relative flow (f) and the absolute tissue flow ($F_t$) with respect to the relative flow (f).

8. Method according to claim 6, wherein the normalised relative tissue flow, respectively the blood volume, is also normalised with the injected tracer dose being the ratio between tracer amount and body weight of the individual mammal.

9. Method according to claim 6, wherein the previously determined conversion factor is in general applicable for the present method to members of a mammalian specie.

10. Method according to claim 6, wherein the previously determined conversion factor is in general applicable for the present method to an organ or tissue of the mammalian specie.

11. Method according to claim 6, wherein the previously determined conversion factor is a constant factor applicable for the present method for any organ or any part of tissue of the mammalian specie.

12. Method according to claim 6, wherein the previously determined conversion factor is a constant factor applicable for all of cerebral tissue of the mammalian specie.

13. Method according to claim 3, wherein the tomographic data comprise information pertaining to subregions of sections of the organ or part of tissue and the haemodynamic indices are determined for at least a substantial part of said subregions, and wherein quantitative haemodynamic parameters are represented as images subdivided into a plurality of pixels each representing a quantitative haemodynamic parameter pertaining to one of said subregions.

14. Method according to claim 1, wherein the tomographic data are obtained by means of magnetic resonance imaging.

15. Method according to claim 1, wherein the tissue is cerebral tissue.

16. Method according to claim 15, wherein the tomographic data are obtained by means of susceptibility contrast magnetic resonance imaging.

17. Method according to claim 1, wherein the tissue is renal tissue.

18. Method according to claim 17, wherein the tissue is renal parenchyma tissue.

19. Method according to claim 1, wherein the tissue includes tumour tissue.

20. Method according to claim 1, wherein the tracer is a Gd-chelate, such as Gd-DTPA.

21. Method according to claim 1, wherein the tracer is an ultra small iron oxide particle (USPIO) intravascular contrast agent.

22. Method according to claim 1, wherein the tomographic data comprise information pertaining to subregions of sections of the organ or part of tissue and the haemodynamic indices are determined for at least a substantial part of said subregions.

23. Method according to claim 1, further comprising using a system for processing of the time series of tomographic data pertaining to the organ or the part of tissue, said system residing on a computer having means for producing an output representative of at least some of the determined haemodynamic indices.

24. Method for evaluating the efficacy of a drug or a substance on an organ or on a part of tissue of a mammal by means of haemodynamic indices of said organ or of said part of tissue obtained by a method according to claim 1.

25. Method according to claim 24, further comprising using a system for processing of the time series of tomographic data pertaining to the organ or the part of a tissue, said system residing on a computer having means for producing an output representative of at least some of the determined haemodynamic indices.

26. Use of information obtained by use of the method according to claim 24 for preparing a reference table for use in discrimination of a treatment schedule for an individual mammal or group of mammals for which information have been obtained in a manner similar to said information.

27. Method for obtaining information of the likelihood of recovery of an organ or part of tissue in a living mammal upon or during a period of insufficient vascular supply of said organ or of said part of tissue in the mammal comprising determining haemodynamic indices according to claim 1.

28. Method for obtaining information of the likelihood of progression of a chronic or neoplastic disease process of an organ or part of tissue in a living mammal affecting said organ or said part of tissue in the mammal comprising determining haemodynamic indices according to claim 1.

29. Method for obtaining information relevant for discrimination between relevant therapy of an organ or part of tissue in a living mammal upon or a period of insufficient vascular supply of said organ or of said part of tissue in the mammal comprising determining haemodynamic indices according to claim 1.

30. Method for obtaining information relevant for discriminating between relevant therapy of an organ or part of tissue in a living mammal upon the discovery of a chronic or neoplastic disease of said organ or of said part of tissue in the mammal comprising determining haemodynamic indices according to claim 1.

31. Use of information obtained by use of the method according to claim 1 for preparing a reference table for use in discrimination of a treatment schedule for an individual mammal or group of mammals for which information have been obtained in a manner similar to said information.

* * * * *